US011262356B2

(12) United States Patent
Okamoto et al.

(10) Patent No.: US 11,262,356 B2
(45) Date of Patent: Mar. 1, 2022

(54) SPECIMEN ANALYSIS SUBSTRATE, SPECIMEN ANALYSIS DEVICE, SPECIMEN ANALYSIS SYSTEM, AND PROGRAM FOR SPECIMEN ANALYSIS SYSTEM

(71) Applicant: PHC HOLDINGS CORPORATION, Tokyo (JP)

(72) Inventors: Fusatoshi Okamoto, Ehime (JP); Masahiro Johno, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 776 days.

(21) Appl. No.: 16/066,641

(22) PCT Filed: Dec. 22, 2016

(86) PCT No.: PCT/JP2016/088569
§ 371 (c)(1),
(2) Date: Jun. 27, 2018

(87) PCT Pub. No.: WO2017/115733
PCT Pub. Date: Jul. 6, 2017

(65) Prior Publication Data
US 2019/0018007 A1    Jan. 17, 2019

(30) Foreign Application Priority Data

Dec. 28, 2015 (JP) .............................. JP2015-256412

(51) Int. Cl.
| G01N 33/543 | (2006.01) |
| G01N 37/00 | (2006.01) |
| G01N 35/00 | (2006.01) |
| G01N 35/10 | (2006.01) |
| B01L 3/00 | (2006.01) |

(52) U.S. Cl.
CPC ........ *G01N 33/54386* (2013.01); *B01L 3/502* (2013.01); *B01L 3/50273* (2013.01); *G01N 33/543* (2013.01); *G01N 35/00* (2013.01); *G01N 35/00069* (2013.01); *G01N 35/0098* (2013.01); *G01N 35/10* (2013.01); *G01N 35/1016* (2013.01); *G01N 37/00* (2013.01); *B01L 2200/06* (2013.01); *B01L 2200/0621* (2013.01); *B01L 2200/0668* (2013.01); *B01L 2300/0803* (2013.01); *B01L 2300/0864* (2013.01); *B01L 2300/0867* (2013.01); *B01L 2400/043* (2013.01); *B01L 2400/0406* (2013.01); *B01L 2400/0409* (2013.01); *B01L 2400/0457* (2013.01); *G01N 2035/00495* (2013.01)

(58) Field of Classification Search
None
See application file for complete search history.

(56) References Cited

U.S. PATENT DOCUMENTS

| 8,703,070 | B1 * | 4/2014 | Parng ................... B01L 3/5027 422/503 |
| 10,539,582 | B2 * | 1/2020 | Okamoto ........... G01N 35/0098 |
| 2002/0039783 | A1 * | 4/2002 | McMillan .............. C12M 47/06 435/287.2 |
| 2008/0056949 | A1 | 3/2008 | Lee et al. |
| 2008/0102537 | A1 | 5/2008 | Harding et al. |
| 2010/0078322 | A1 | 4/2010 | Yamanishi et al. |
| 2011/0117665 | A1 | 5/2011 | Saiki et al. |
| 2013/0004964 | A1 | 1/2013 | Boehm et al. |
| 2014/0242721 | A1 | 8/2014 | Kellogg et al. |

FOREIGN PATENT DOCUMENTS

| JP | H07-500910 A | 1/1995 |
| JP | 2001-502793 A | 2/2001 |
| JP | 2007-003361 A | 1/2007 |
| JP | 2007-315879 A | 12/2007 |
| JP | 2008-064753 A | 3/2008 |
| JP | 2013-505431 A | 2/2013 |
| WO | 93/08893 A1 | 5/1993 |
| WO | 98/13684 A1 | 4/1998 |

OTHER PUBLICATIONS

Extended European Search Report issued in European Patent Application No. 16881708.8, dated Dec. 4, 2018.
International Search Report issued in International Application No. PCT/JP2016/088569 dated Mar. 14, 2017 (with English translation).

* cited by examiner

*Primary Examiner* — Ann Montgomery
(74) *Attorney, Agent, or Firm* — McDermott Will and Emery LLP

(57) ABSTRACT

A sample analysis substrate includes a substrate; a first holding chamber; a reaction chamber; a first flow path having a first opening and a second opening respectively connected with the first holding chamber and reaction chamber; a main chamber; a second flow path having a third opening and a fourth opening respectively connected with the reaction chamber and the main chamber; and a magnet accommodation chamber capable of accommodating a magnet. The first opening is located closer to a rotation shaft than the second opening. The second opening is located closer to the rotation shaft than the third opening. The magnet accommodation chamber is located at a position at which, in the case where the magnet is accommodated in the magnet accommodation chamber, the magnet captures magnetic particles in the main chamber. The sample analysis substrate is rotatable to transfer a liquid.

17 Claims, 40 Drawing Sheets

FIG.19
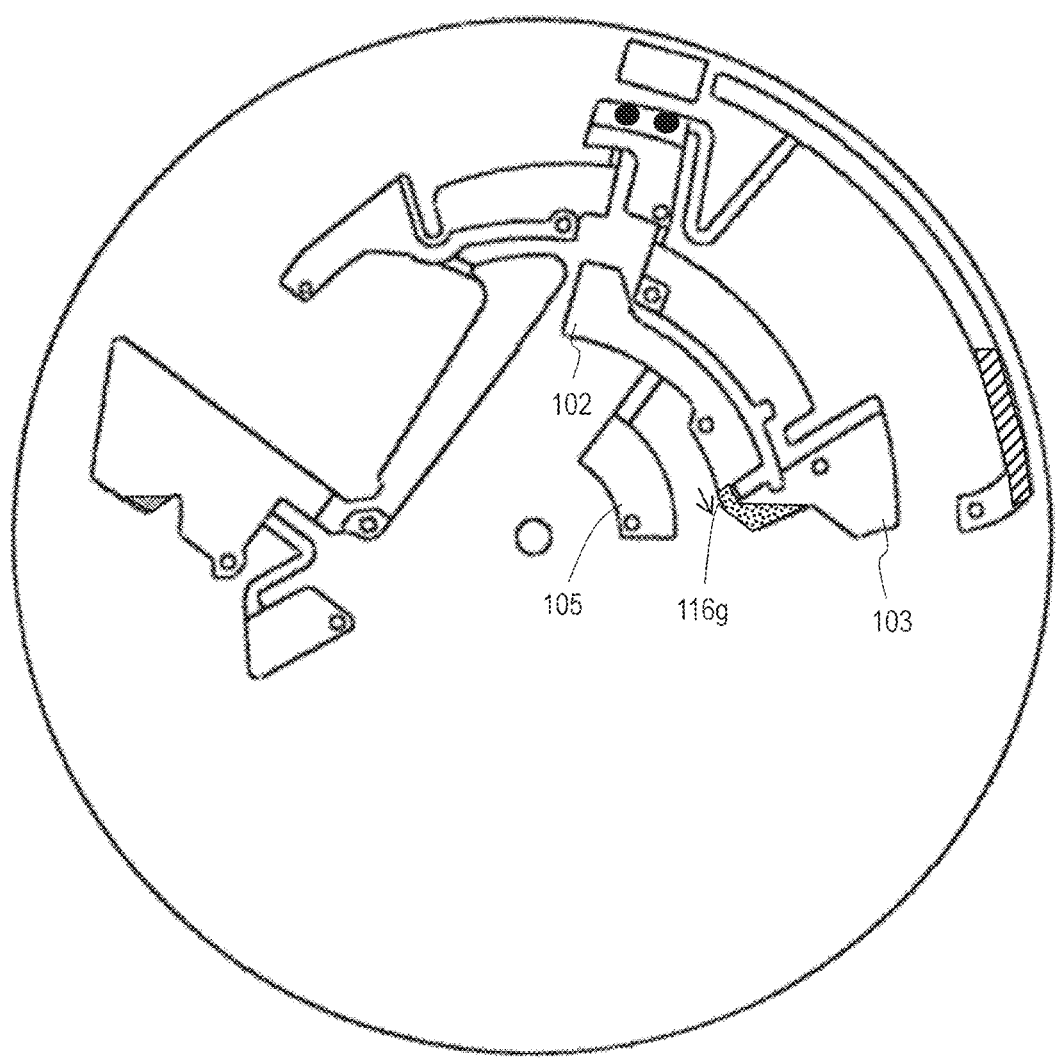
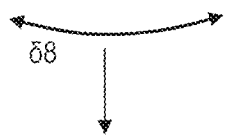

SPECIMEN ANALYSIS SUBSTRATE, SPECIMEN ANALYSIS DEVICE, SPECIMEN ANALYSIS SYSTEM, AND PROGRAM FOR SPECIMEN ANALYSIS SYSTEM

CROSS REFERENCE

This application is the U.S. National Phase under 35 U.S.C. § 371 of International Application No. PCT/JP2016/088569 filed on Dec. 22, 2016, which claims the benefit of Japanese Application No. 2015-256412 filed on Dec. 28, 2015, the entire contents of each are hereby incorporated by reference.

TECHNICAL FIELD

The present application relates to a sample analysis substrate, a sample analysis device, a sample analysis system, and a program for the sample analysis system.

BACKGROUND ART

Conventionally, a technology of using a sample analysis substrate in order to analyze a specific component in a specimen of urine, blood or the like is known. For example, Patent Literature 1 discloses a technology of using a discus-shaped sample analysis substrate including flow paths, chambers and the like formed therein and, for example, rotating the sample analysis substrate to, for example, transfer, distribute or mix a solution or analyze a component in the specimen solution.

CITATION LIST

Patent Literature

Patent Document No. 1: Japanese Laid-Open Patent Publication No. Hei 7-500910

SUMMARY OF INVENTION

Technical Problem

A method for analyzing a specific component in a specimen includes a complicated reaction step performed by use of an enzyme reaction, an immune reaction or the like. A technology allowing an analysis method including such a complicated reaction step to be performed in a sample analysis substrate has been desired.

An non-limiting and illustrative embodiment of the present application provides a sample analysis substrate, a sample analysis device, a sample analysis system and a program for the sample analysis system usable for an analysis method including a more complicated reaction step to analyze a component in a specimen.

Solution to Problem

A sample analysis substrate rotatable to transfer a liquid according to this disclosure includes a substrate including a rotation shaft; a first holding chamber located in the substrate, the first holding chamber having a first space usable to hold a first liquid; a reaction chamber located in the substrate, the reaction chamber having a second space usable to hold a specimen-containing liquid sample; a first flow path located in the substrate, the first flow path having a first opening and a second opening respectively connected with the first holding chamber and reaction chamber; a main chamber located in the substrate, the main chamber having a space usable to hold the specimen-containing liquid sample and magnetic particles having a ligand immobilized to a surface thereof; a second flow path located in the substrate, the second flow path having a third opening and a fourth opening respectively connected with the reaction chamber and the main chamber; and a magnet accommodation chamber located in the substrate, the magnet accommodation chamber being capable of accommodating a magnet. The first opening is located closer to the rotation shaft than the second opening; the second opening is located closer to the rotation shaft than the third opening; and the magnet accommodation chamber is located at a position at which, in the case where the magnet is accommodated in the magnet accommodation chamber, the magnet captures the magnetic particles in the main chamber.

Advantageous Effects of Invention

A sample analysis substrate, a sample analysis device, a sample analysis system and a program for the sample analysis system in an embodiment according to the present application is usable for an analysis method including a more complicated reaction step to analyze a component in a specimen.

BRIEF DESCRIPTION OF DRAWINGS

FIG. 19 schematically shows an example of angle at which the sample analysis substrate is stopped and an example of position of the liquid during the operation of the sample analysis system.

DESCRIPTION OF EMBODIMENTS

A method for analyzing a component in a specimen of urine, blood or the like may use a binding reaction of an analyte, which is a target of analysis, and a ligand specifically bindable with the analyte. Examples of such an analysis method include an immunological measurement method and a gene diagnosis method.

Examples of the immunological measurement method include a competitive immunoassay and a sandwich immunoassay. An example of the gene diagnosis method is a gene detection method by use of hybridization. The immunological measurement method and the gene detection method use, for example, magnetic particles (may also be referred to as "magnetic beads", "magnet particles", "magnet beads" or the like). As an example of such an analysis method, a sandwich immunoassay using magnetic particles will be described specifically.

Figure 1:
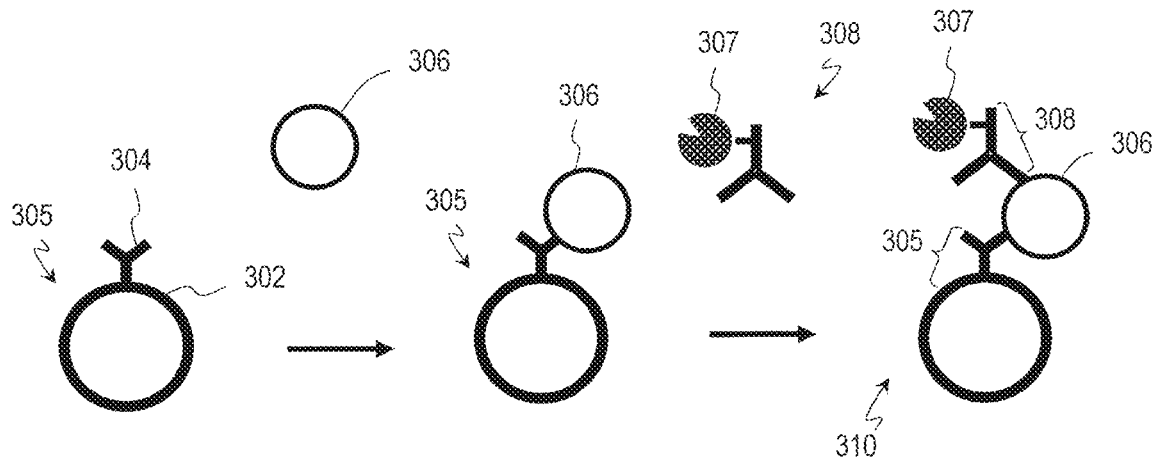
FIG. 1 shows an example of schematic view showing a sandwich immunoassay using a magnetic particle.

As shown in FIG. 1, first, a primary antibody 304 immobilized on a surface of a magnetic particle 302 (hereinafter, referred to as a "magnetic particle-immobilized antibody 305") and an antigen 306, which is a target of measurement, are bound to each other by an antigen-antibody reaction. Next, a secondary antibody having a labeling substance 307 bound thereto (hereinafter, referred to as a "labeled antibody 308") and the antigen 306 are bound to each other by an antigen-antibody reaction. As a result, a complex body 310 including the antigen 306, and the magnetic particle-immobilized antibody 305 and the labeled antibody 308 bound to the antigen 306, is obtained.

A signal based on the labeling substance 307 of the labeled antibody 308 bound to the complex body 310 is detected, and the antibody concentration is measured in accordance with the amount of the detected signal. The labeling substance 307 may be, for example, an enzyme (e.g., peroxidase, alkaline phosphatase, luciferase, etc.), a chemical light emitting substance, an electrochemical light emitting substance, a fluorescent substance or the like. A signal such as a colorant, light emission, fluorescence or the like is detected in accordance with the type of labelling substance 307.

In order to obtain the complex body 310 as a reaction product by the above-described series of reactions, it is required to separate an unreacted substance in the specimen, a substance non-specifically adsorbed to the magnetic particle or the like, and an unreacted substance, for example, the labeled antibody 308 not involved in the formation of the complex body 310. Such separation is referred to as "B/F separation" (Bound/Free Separation). The competitive immunoassay as an example of the immune measurement method, and the gene detection method by use of hybridization, also need to perform the step of B/F separation.

In the above, the sandwich immunoassay performed by use of a magnetic particle is described as an example. The B/F separation is needed in the competitive immunoassay and the sandwich immunoassay as examples of the immune measurement method and the gene detection method by use of hybridization, regardless of whether the magnetic particle is used or not. In the case where the magnetic particle is not used, a ligand as follows is used, for example: a ligand immobilized by physical adsorption to a solid phase formed of a material such as polystyrene or polycarbonate, a ligand immobilized by a chemical bond to a solid phase, a ligand immobilized to a surface of a metal substrate formed of gold or the like (e.g., immobilized by use of a Self-Assembled Monolayer (SAM)), etc.

In order to sufficiently perform the B/F separation, it is preferred to wash the magnetic particle containing the complex body 310 with a washing solution a plurality of times. Specifically, first, the complex body 310 containing the magnetic particle is captured by a magnet in a reaction solution containing the complex body 310, the unreacted antigen 306, the labeled antibody 308 and the like, and in this state, only the reaction solution is removed. Then, the washing solution is added to wash the complex body 310, and the washing solution is removed. Such washing is performed a plurality of times, and as a result, the unreacted substance and non-specifically adsorbed substance are sufficiently removed to finish the B/F separation.

Conventionally, an operation of washing the complex body 310 after such an antigen-antibody reaction is performed manually by an operating person by use of an analysis tool or realized by a large-scale analysis device including a complicated mechanism. Under such a situation, a technology of performing the washing more simply has been desired.

After the complex body 310 is washed as described above, the complex body 310 is reacted with a substrate solution to generate a signal based on labelling substance 307. In this step, a chamber that had held the reaction solution still has a portion thereof remaining therein, the remaining reaction solution may be transferred to a chamber holding the complex body 310 and reacted with the substrate solution to generate a signal by mistake. It is desired to suppress a measurement error from being caused by such a signal and to realize more accurate signal measurement.

The present inventors made detailed studies on a technology that realizes the step of causing an antigen-antibody reaction and the step of performing the washing a plurality of times after the antigen-antibody reaction by use of a sample analysis substrate as disclosed in Patent Literature 1, and conceived a novel sample analysis substrate, a novel sample analysis device, a novel sample analysis system and a novel program for the sample analysis system. The sample analysis substrate, the analysis device, the sample analysis system and the program for the sample analysis system in an embodiment of the present application are as follows.

[Item 1]

A sample analysis substrate rotatable to transfer a liquid, the sample analysis substrate comprising:

a substrate including a rotation shaft;

a first holding chamber located in the substrate, the first holding chamber having a first space usable to hold a first liquid;

a reaction chamber located in the substrate, the reaction chamber having a second space usable to hold a specimen-containing liquid sample;

a first flow path located in the substrate, the first flow path having a first opening and a second opening respectively connected with the first holding chamber and reaction chamber;

a main chamber located in the substrate, the main chamber having a space usable to hold the specimen-containing liquid sample and magnetic particles having a ligand immobilized to a surface thereof;

a second flow path located in the substrate, the second flow path having a third opening and a fourth opening respectively connected with the reaction chamber and the main chamber; and a magnet accommodation chamber located in the substrate, the magnet accommodation chamber being capable of accommodating a magnet;

wherein:

the first opening is located closer to the rotation shaft than the second opening;

the second opening is located closer to the rotation shaft than the third opening; and the magnet accommodation chamber is located at a position at which, in the case where the magnet is accommodated in the magnet accommodation chamber, the magnet captures the magnetic particles in the main chamber.

[Item 2]

The sample analysis substrate of item 1, further comprising a dried agent located in a space of the reaction chamber, wherein the dried agent contains the magnetic particles.

[Item 3]

The sample analysis substrate of item 1 or 2, wherein the reaction chamber has a non-capillary space.

[Item 4]

The sample analysis substrate of item 1 or 2, wherein the reaction chamber has a capillary space.

[Item 5]

The sample analysis substrate of item 1 or 2, wherein:

the reaction chamber has a non-capillary space and a capillary space;

the first opening is in contact with the non-capillary space; and the third opening is in contact with the capillary space.

[Item 6]

The sample analysis substrate of item 5, wherein the non-capillary space includes a portion located closer to the rotation shaft than the capillary space.

[Item 7]

The sample analysis substrate of item 5, wherein:

the reaction chamber includes a first portion and a second portion;

the substrate includes a wall portion located between the first portion and the second portion of the reaction chamber;

the wall portion includes a protruding portion protruding toward the rotation shaft; and the first portion and the second portion respectively include a part of the capillary space and a part of the non-capillary space located farther from the rotation shaft than an arc having, as a radius, a line segment connecting the rotation shaft and a point, in the wall portion, that is closest to the rotation shaft.

[Item 8]

The sample analysis substrate of item 7, wherein a part, of the capillary space, that connects the first portion and the second portion to each other is located in a part of, the wall portion, that is closer to the first portion or in the entirety of the wall portion.

[Item 9]

The sample analysis substrate of any one of items 1 through 8, further comprising:

a recovery chamber located in the substrate, the recovery chamber having a space;

a third flow path located in the substrate, the third flow path having a fifth opening and a sixth opening respectively connected with the main chamber and the recovery chamber;

wherein the fifth opening is located closer to the rotation shaft than the sixth opening.

[Item 10]

The sample analysis substrate of any one of items 1 through 9, wherein the first flow path is a non-capillary channel.

[Item 11]

The sample analysis substrate of item 10, wherein:

the first holding chamber has an outermost side surface farthest from the rotation shaft and an adjacent side surface adjacent to the outermost side surface;

the outermost side surface and the adjacent side define a recessed portion; and in the case where the sample analysis substrate is held at a predetermined angle, the first liquid is held in the recessed portion.

[Item 12]

The sample analysis substrate of any one of items 1 through 11, wherein the first flow path is a capillary channel.

[Item 13]

The sample analysis substrate of item 12, wherein the first flow path has a siphon structure.

[Item 14]

The sample analysis substrate of item 12, wherein a part of the first flow path is located closer to the rotation shaft than a part of the first holding chamber with the first opening being located between the part of the first flow path and the part of the first holding chamber.

[Item 15]

The sample analysis substrate of item 12, wherein:

the space of the first holding chamber includes a first portion, a second portion, and a coupling portion located between the first portion and the second portion, the coupling portion coupling the first portion and the second portion to each other;

the substrate includes a wall portion separating the first portion and the second portion of the space of the first holding chamber from each other;

the reaction chamber is located farther from the rotation shaft than the second portion of the first holding chamber;

the coupling portion of the space of the first holding chamber is located closer to the rotation shaft than the wall portion of the substrate; and the first flow path is connected with the second portion of the space of the first holding chamber.

[Item 16]

The sample analysis substrate of any one of items 1 through 14, further comprising:

a fourth holding chamber located in the substrate, the fourth holding chamber having a space usable to accommodate a second liquid; and an eighth flow path connecting the fourth holding chamber and the reaction chamber to each other, the eighth flow path being usable to transfer the second liquid;

wherein:

the first holding chamber has an outermost side surface located farthest from the rotation shaft, an adjacent side surface adjacent to the outermost side surface, and a recessed portion defined by the outermost side surface and the adjacent side surface;

the fourth holding chamber has an outermost side surface located farthest from the rotation shaft, an adjacent side surface adjacent to the outermost side surface, and a recessed portion defined by the outermost side surface and the adjacent side surface; and the adjacent side surface of the first holding chamber and the adjacent side surface of the fourth holding chamber are unparallel to each other as seen in a direction parallel to the rotation shaft.

[Item 17]

A sample analysis system, comprising:

the sample analysis substrate of any one of items 1 through 16; and a sample analysis device including:

a motor rotating the sample analysis substrate about the rotation shaft;

a rotation angle detection circuit detecting a rotation angle of a rotation shaft of the motor;

a driving circuit controlling the rotation of the motor and the rotation angle at which the motor stops, based on a result of the detection of the rotation angle detection circuit; and a control circuit including an operator, a memory and a program stored on the memory so as to be executable by the operator, the control circuit controlling an operation of the motor, the rotation angle detection circuit and the driving circuit based on the program;

wherein in the case where the sample analysis substrate in which the first holding chamber and the reaction chamber have the first liquid and the liquid sample introduced thereto is mounted on the sample analysis device, the program:

(a) rotates the sample analysis substrate to transfer the liquid sample in the reaction chamber to the main chamber;

(b) rotates the sample analysis substrate to, after step (a), transfer the first liquid in the first holding chamber to the reaction chamber; and (c) rotates the sample analysis substrate to transfer the first liquid in the reaction chamber to the main chamber.

[Item 18]

A sample analysis device, comprising:

a motor rotating the sample analysis substrate of any one of items 1 through 16 about the rotation shaft;

a rotation angle detection circuit detecting a rotation angle of a rotation shaft of the motor;

a driving circuit controlling the rotation of the motor and the rotation angle at which the motor stops, based on a result of the detection of the rotation angle detection circuit; and a control circuit including an operator, a memory and a program stored on the memory so as to be executable by the operator, the control circuit controlling an operation of the motor, the rotation angle detection circuit and the driving circuit based on the program;

wherein in the case where the sample analysis substrate in which the first holding chamber and the reaction chamber have the first liquid and the liquid sample introduced thereto is mounted on the sample analysis device, the program:

(a) rotates the sample analysis substrate to transfer the liquid sample in the reaction chamber to the main chamber;

(b) rotates the sample analysis substrate to, after step (a), transfer the first liquid in the first holding chamber to the reaction chamber; and (c) rotates the sample analysis substrate to transfer the first liquid in the reaction chamber to the main chamber.

[Item 19]

A program for a sample analysis system, the sample analysis system including:

the sample analysis substrate of any one of items 1 through 16; and a sample analysis device including:
a motor rotating the sample analysis substrate about the rotation shaft;
a rotation angle detection circuit detecting a rotation angle of a rotation shaft of the motor;
a driving circuit controlling the rotation of the motor and the rotation angle at which the motor stops, based on a result of the detection of the rotation angle detection circuit; and
a control circuit including an operator, a memory and a program stored on the memory so as to be executable by the operator, the control circuit controlling an operation of the motor, the rotation angle detection circuit and the driving circuit based on the program;

wherein in the case where the sample analysis substrate in which the first holding chamber and the reaction chamber have the first liquid and the liquid sample introduced thereto is mounted on the sample analysis device, the program:

(a) rotates the sample analysis substrate to transfer the liquid sample in the reaction chamber to the main chamber;

(b) rotates the sample analysis substrate to, after step (a), transfer the first liquid in the first holding chamber to the reaction chamber; and (c) rotates the sample analysis substrate to transfer the first liquid in the reaction chamber to the main chamber.

[Item 20]

A method for transferring a liquid by use of a sample analysis substrate, the sample analysis substrate being rotatable to transfer the liquid, the sample analysis substrate comprising:

a substrate including a rotation shaft;

a first holding chamber located in the substrate, the first holding chamber having a first space usable to hold a first liquid;

a reaction chamber located in the substrate, the reaction chamber having a space usable to hold an analyte-containing liquid sample;

a first flow path located in the substrate, the first flow path having a first opening and a second opening respectively connected with the first holding chamber and reaction chamber;

a main chamber located in the substrate, the main chamber having a space usable to hold the analyte-containing liquid sample and magnetic particles having a ligand immobilized to a surface thereof;

a second flow path located in the substrate, the second flow path having a third opening and a fourth opening respectively connected with the reaction chamber and the main chamber; and a magnet accommodation chamber located in the substrate, the magnet accommodation chamber usable to accommodate a magnet;

wherein:

the first opening is located closer to the rotation shaft than the second opening;

the second opening is located closer to the rotation shaft than the third opening; and the magnet accommodation chamber is located at a position at which, in the case where the magnet is accommodated in the magnet accommodation chamber, the magnet captures the magnetic particles in the main chamber;

the method comprising:

(a) introducing the first liquid and the liquid sample respectively into the first holding chamber and the reaction chamber;

(b) transferring the liquid sample in the reaction chamber to the main chamber;

(c) after step (b), transferring the first liquid in the first holding chamber to the reaction chamber; and (d) transferring the first liquid in the reaction chamber to the main chamber.

Hereinafter, a sample analysis substrate, a sample analysis device, a sample analysis system and a program for the sample analysis system in this embodiment will be described in detail with reference to the attached drawing. In the drawings of this disclosure, a part of the components may be omitted, or reference signs thereof may be omitted, for easier understanding.

According to the sample analysis substrate, the sample analysis device, the sample analysis system and the program for the sample analysis system in this embodiment, even if a chamber that held the reaction solution still has a portion thereof remaining therein, highly accurate signal measurement is performed. In addition, in the case where two or more liquids held in different chambers are to be transferred to another chamber, the sample analysis substrate is rotated in various manners to prevent, with certainty, the liquids from being transferred at a timing when the liquids do not need to be transferred. For example, a certain amount of washing solution held in one or a plurality of chambers is weighed out and transferred to another chamber a plurality of times to perform the B/F separation. In this case, a substrate solution held in the another chamber is prevented, with certainty, from being transferred at a timing when the substrate solution does not need to be transferred. In this embodiment, the liquid is described as a substrate solution or as a washing solution. The liquid is not limited to the substrate solution or the washing solution, and may be any of various types of liquid usable for sample analysis.

Figure 2A:
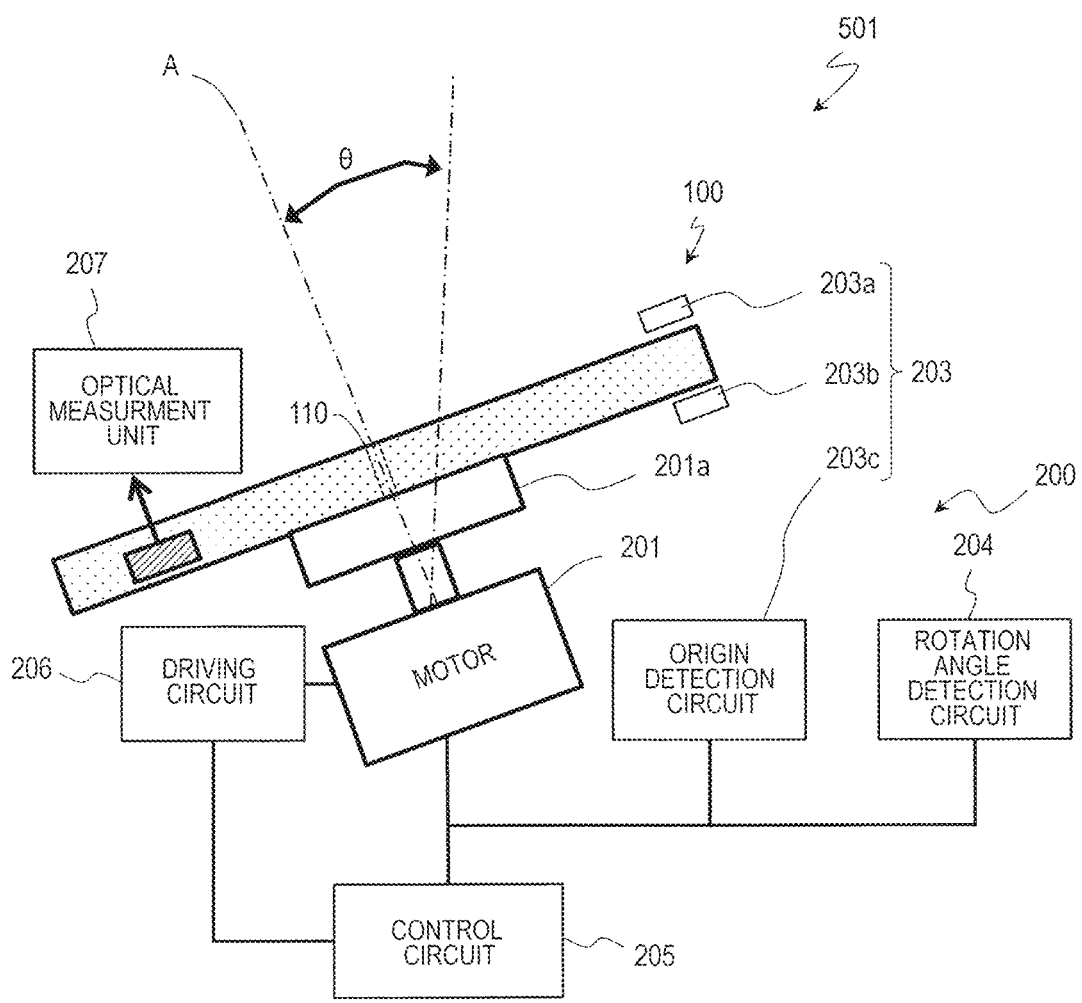
FIG. 2A is a schematic view showing an example of structure of a sample analysis system in an embodiment.

FIG. 2A is a schematic view showing an overall structure of a sample analysis system 501. The sample analysis system 501 includes a sample analysis substrate 100 and a sample analysis device 200.

(Structure of the Sample Analysis Device 200)

The sample analysis device 200 includes a motor 201, an origin detector 203, a rotation angle detection circuit 204, a control circuit 205, a driving circuit 206, and an optical measurement unit 207.

The motor 201 includes a turntable 201*a* and a rotation shaft A inclined with respect to the direction of gravity (vertical direction) G by angle θ that is larger than 0 degrees and 90 degrees or smaller, and rotates the sample analysis substrate 100 located on the turntable 201*a* about the rotation shaft A. Since the rotation shaft A is inclined, a centrifugal force provided by the rotation and also a movement realized by a gravitational force are usable to transfer a liquid in the sample analysis substrate 100. An inclination angle of the rotation shaft A with respect to the direction of gravity G is preferably 5 degrees or larger, more preferably 10 degrees or larger and 45 degrees or smaller, and still more preferably 20 degrees or larger and 30 degrees or smaller. The motor 201 may be, for example, a DC motor, brushless motor, an ultrasonic motor or the like.

Figure 2B:
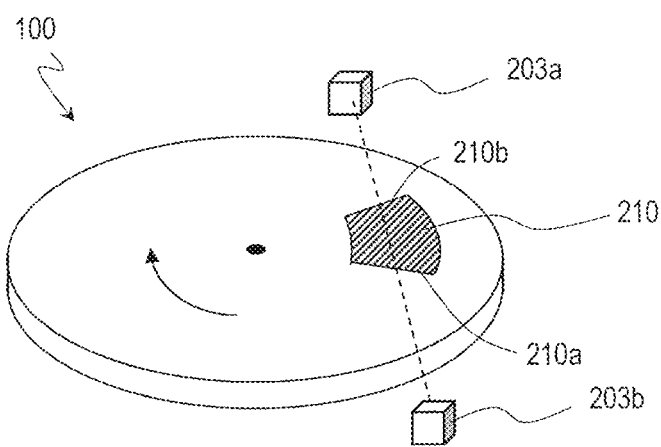
FIG. 2B is a schematic view showing an example of structure detecting an origin of a sample analysis substrate in the sample analysis system.

The origin detector 203 detects an origin of the sample analysis substrate 100 attached to the motor 201. For example, as shown in FIG. 2A, the origin detector 203 includes a light source 203a, a light receiving element 203b and an origin detection circuit 203c, and is located such that the sample analysis substrate 100 is located between the light source 203a and the light receiving element 203b. For example, the light source 203a is a light emitting diode, and the light receiving element 203b is a photodiode. As shown in FIG. 2B, the sample analysis substrate 100 includes a marker 210 located at a specific position. The marker 210 has, for example, a light-blocking property and blocks a part of light emitted from the light source 203a. A region of the sample analysis substrate 100 where the marker 210 is provided has a low light transmittance (e.g., 10% or lower), and a region of the sample analysis substrate 100 other than the marker 210 has a high light transmittance (e.g., 60% or higher).

When the sample analysis substrate 100 is rotated by the motor 201, the light receiving element 203b outputs a detection signal in accordance with the amount of light incident thereon to the origin detection circuit 203c. In accordance with the rotation direction, the detection signal is increased or decreased at an edge 210a or an edge 210b of the marker 210. In the case where, for example, the sample analysis substrate 100 is rotated clockwise as represented by the arrow, the origin detection circuit 203c detects a decrease in the detected amount of light and outputs the decrease as an origin signal. In this specification, the position of the edge 210a of the marker 210 is treated as the position of the origin of the sample analysis substrate 100 (angular position acting as a reference for the sample analysis substrate 100). Alternatively, a specific angular position arbitrarily defined based on the position of the edge 210a of the marker 210 may be defined as the origin position. In the case where the marker 210 is fan-shaped and a central angle thereof is smaller than the angle detection accuracy required for sample analysis, the position of the marker 210 itself may be defined as the origin position.

The origin position is used by the sample analysis device 200 to acquire information on a rotation angle of the sample analysis substrate 100. The origin detector 203 may have another structure. For example, the sample analysis substrate 100 may include a magnet for detecting the origin and the origin detector 203 may be a magnetism detection element that detects the magnetism of the magnet. Alternatively, a magnet described below that captures the magnetic particles may be used to detect the origin. In the case where the sample analysis substrate 100 is attachable to the turntable 201a only at a specific angle, the origin detector 203 does not need to be provided.

The rotation angle detection circuit 204 detects an angle of the rotation shaft A of the motor 201. The rotation angle detection circuit 204 may be, for example, a rotary encoder attached to the rotation shaft A. In the case where the motor 201 is a brushless motor, the rotation angle detection circuit 204 may include a hall element and a detection circuit that receives an output signal from the hall element and outputs the angle of the rotation shaft A.

The driving circuit 206 rotates the motor 201. Specifically, the driving circuit 206 rotates the sample analysis substrate 100 clockwise or counterclockwise based on an instruction from the control circuit 205. The driving circuit 206 also stops swinging or rotating the sample analysis substrate 100 based on the detection results provided by the rotation angle detection circuit 204 and the origin detector 203 and an instruction from the control circuit 205.

The optical measurement unit 207 detects a signal (e.g., colorant, light emission, fluorescence, etc.) in accordance with the labeling substance 307 of the labeled antibody 308 bound to the complex body 310 (FIG. 1) held on the sample analysis 100.

The control circuit 205 includes, for example, a CPU provided in the sample analysis device 200. The control circuit 205 executes a computer program read into a RAM (Random Access Memory; not shown) to transmit a command to other circuits in accordance with a procedure of the computer program. Each of the circuits receiving the command operates as described in this specification to realize the function of the corresponding circuit. As shown in, for example, FIG. 2A, the command from the control circuit 205 is transmitted to the driving circuit 206, the rotation angle detection circuit 204, the optical measurement unit 207 and the like. The procedure of the computer program is shown in the flowchart provided in one of the attached drawings.

The RAM having the computer program read thereinto, namely, the RAM having the computer program stored thereon, may be volatile or non-volatile. A volatile RAM does not hold the information stored thereon unless power is supplied thereto. For example, a dynamic random access memory (DRAM) is a typical volatile RAM. A non-volatile RAM holds the information even if no power is supplied thereto. For example, a magnetoresistive RAM (MRAM), a resistive random access memory (ReRAM) and a ferroelectric random access memory (FeRAM) are examples of non-volatile RAM. In this embodiment, it is preferred to use a non-volatile RAM.

A volatile RAM and a non-volatile RAM are both examples of non-transitory computer-readable storage medium. A magnetic storage medium such as a hard disc or like and an optical storage medium such as an optical disc or the like are also examples of non-transitory computer-readable storage medium. Namely, a computer program according to this disclosure may be stored on any of various non-transitory computer-readable mediums, other than a medium such as air or the like (temporary medium), that propagates the computer program as a radio signal.

In this specification, the control circuit 205 is described as an element separated from the rotation angle detection circuit 204 and the origin detection circuit 203c of the origin detector 203. Alternatively, these circuits may be realized by common hardware. For example, the CPU (computer) included in the sample analysis device 200 may execute a computer program acting as the control circuit 205, a computer program acting as the rotation angle detection circuit 204 and a computer program acting as the origin detection circuit 203c of the origin detector 203 in a serial manner or a parallel manner. With such an arrangement, the CPU appears to be operated as different elements.

(Sample Analysis Substrate 100)

[1. Overall Structure]

Figure 3A:
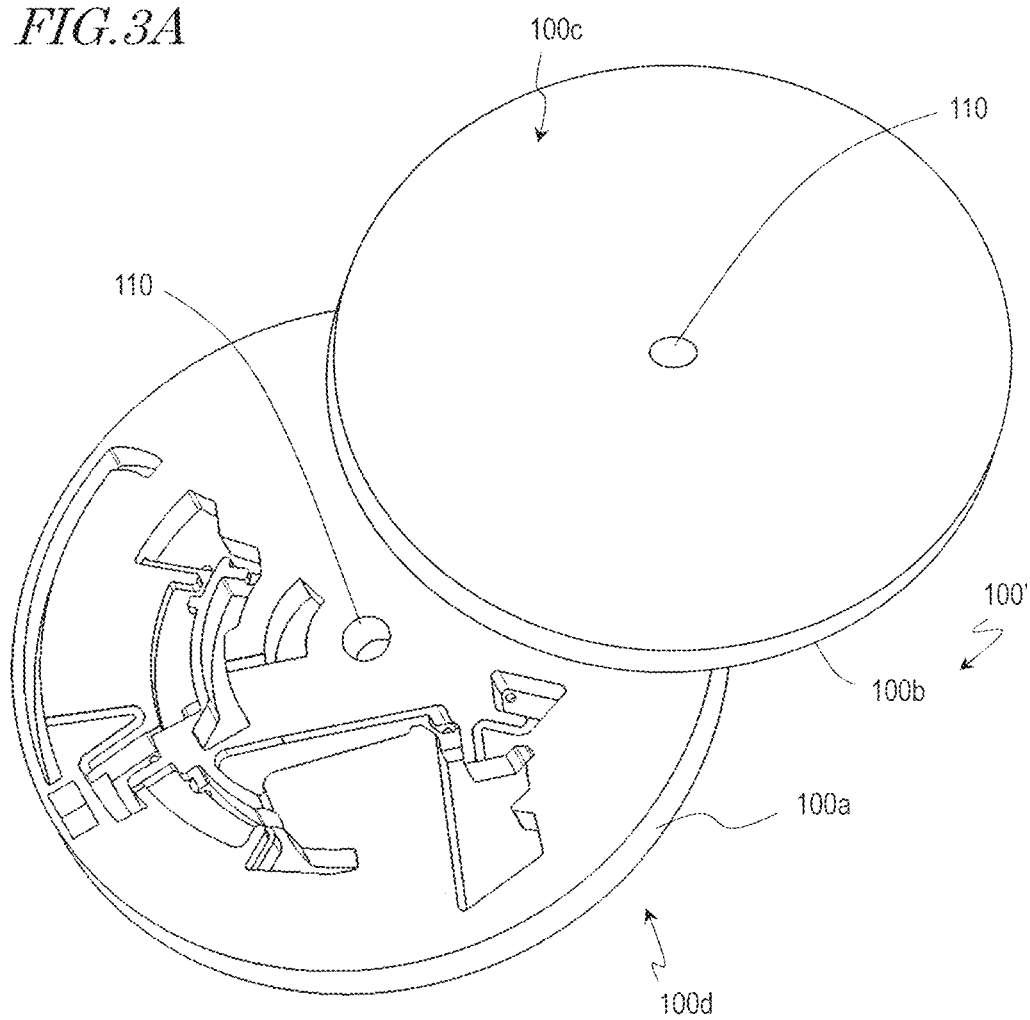
FIG. 3A is an exploded isometric view showing an example of sample analysis substrate.

FIG. 3A is an exploded isometric view of the sample analysis substrate 100. The sample analysis substrate 100 includes a rotation shaft 110 and a plate-like substrate 100' having a predetermined thickness in a direction parallel to the rotation shaft 110. The substrate 100' of the sample analysis substrate 100 includes a base plate 100a and a cover plate 100b. In this embodiment, the substrate 100' of the sample analysis substrate 100 is circular. Alternatively, the substrate 100' of the sample analysis substrate 100 may be, for example, polygonal, elliptical, fan-shaped or the like.

The substrate 100' has two main surfaces 100c and 100d. In this embodiment, the main surface 100c and the main surface 100d are parallel to each other, and a thickness of the substrate 100' defined by the distance between the main surface 100c and the main surface 100d (distance between the two main surfaces) is the same regardless of the position in the substrate 100'. Alternatively, the main surfaces 100c and 100d do not need to be parallel to each other. For example, the two main surfaces may be partially unparallel or parallel to each other, or may be entirely unparallel to each other. Still alternatively, at least one of the main surfaces 100c and 100d may have a recessed portion or a protruding portion.

Figure 3B:
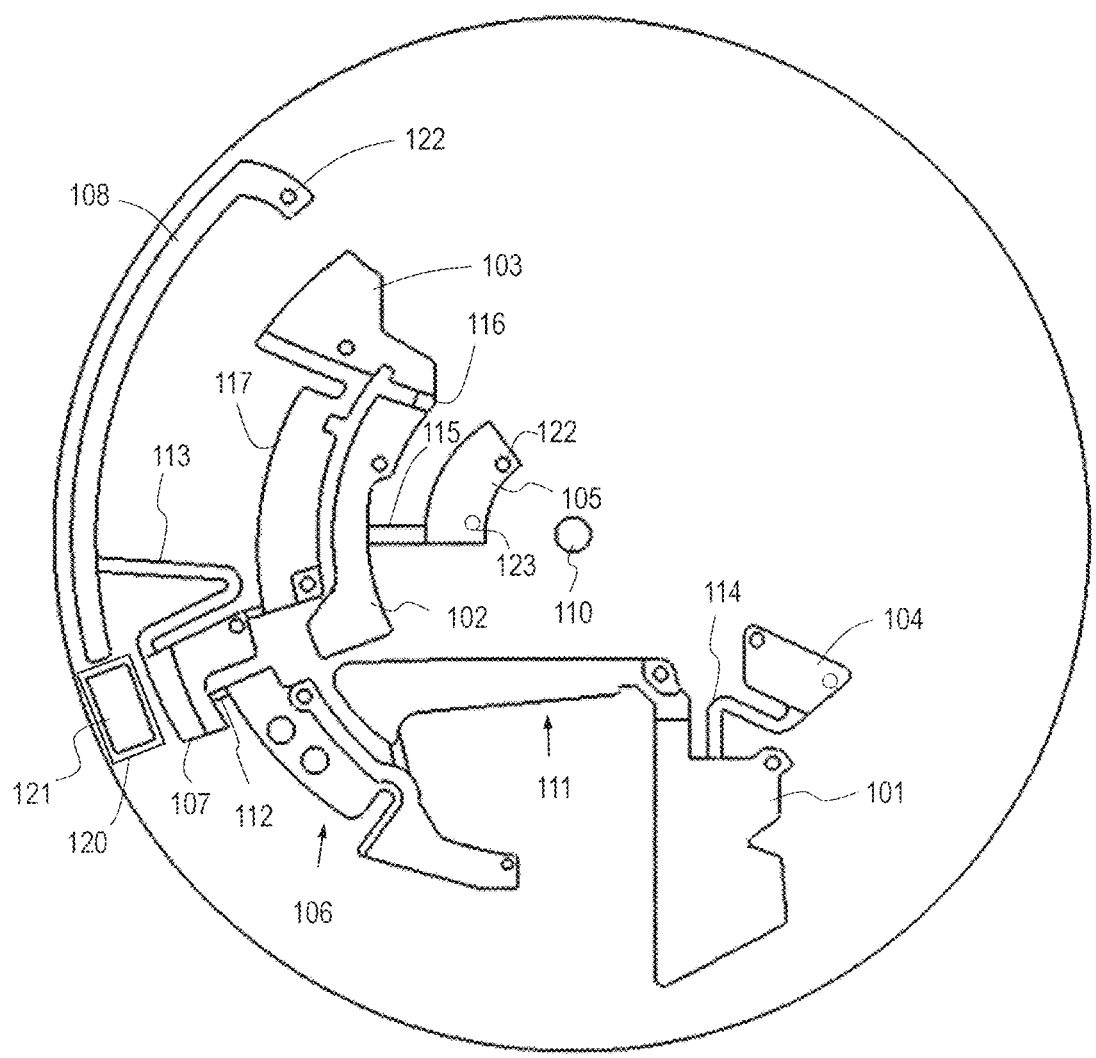
FIG. 3B is a plan view showing an example of sample analysis substrate.

FIG. 3B is a plan view of the base plate 100a. As shown in FIG. 3B, the sample analysis substrate 100 includes a first holding chamber 101, a second holding chamber 102, a third holding chamber 103, a first storage chamber 104, a second storage chamber 105, a reaction chamber 106, a main chamber 107 and a recovery chamber 108 located in the substrate 100'. There is no specific limitation on the shape of each of the chambers unless otherwise specified below. The chambers may have any shape. The chambers each have a space generally defined by a top surface and a bottom surface generally parallel to the two main surfaces 100c and 100d (FIG. 3A) of the substrate 100' and three or more side surfaces located between the two main surfaces 100c and 100d. The top surface, the bottom surface and two adjacent side surfaces among the side surfaces do not need to be divided from each other by a clear ridge. For example, the chambers may each be a flat sphere or a spheroid.

The sample analysis substrate 100 further includes a first flow path 111, a second flow path 112, a third flow path 113, a fourth flow path 114, a fifth flow path 115, a sixth flow path 116, and a seventh flow path 117 located in the substrate 111'. The first flow path 111 connects the first holding chamber 101 and the reaction chamber 106 to each other. The second flow path 112 connects the reaction chamber 106 and the main chamber 107 to each other. The third flow path 113 connects the main chamber 107 and the recovery chamber 108 to each other. The fourth flow path 114 connects the first storage chamber 104 and the first holding chamber 101 to each other. The fifth flow path 115 connects the second storage chamber 105 and the second holding chamber 102 to each other. The sixth flow path 116 connects the second holding chamber 102 and the third holding chamber 103 to each other. The seventh flow path 117 connects the third holding chamber 103 and the main chamber 107 to each other. In this manner, the first holding chamber 101 connected with the first storage chamber 104 via the fourth flow path 114 is connected with the reaction chamber 106, not with the main chamber 107, via the first flow path 111.

A liquid may be transferred between the chambers via the flow paths in any of various methods. For example, transfer by a gravitational force or transfer by a capillary force and rotation may be used. Hereinafter, these two transfer methods will be generally described.

In the case of a flow path in which a liquid is transferable by a gravitational force, the liquid is movable in the flow path by the gravitational force. As shown in, for example, FIG. 2A, the sample analysis substrate 100 is supported by the rotation shaft 110 as being inclined with respect to the direction of gravity G at an angle in the range that is larger than 0 degrees and 90 degrees or smaller. The rotation angle of the sample analysis substrate 100 is changed, so that the chamber as a transfer source that contains the liquid is located at a position higher than that of the chamber as a transfer destination. The term "higher" refers to being above in the direction of gravity G. With such an arrangement, the liquid in the chamber as the transfer source moves in the flow path by the gravitational force and is transferred to the chamber as the transfer destination. The flow path in which a liquid is transferable by a gravitational force is not a capillary channel described below. The flow path in which a liquid is transferable by a gravitational force has a diameter of, for example, 1 mm or longer.

Alternatively, the flow path may be a capillary channel. The "capillary channel" refers to a flow path that has a small cross-section and is allowed to be filled with a liquid in a part thereof by a capillary force provided by a capillary action. Transfer of a liquid via a capillary channel will be described by way of an example of structure including a chamber A and a chamber B, which are not capillary spaces, and a flow path as a capillary channel connecting the chamber A and the chamber B to each other. The liquid held in the chamber A, when contacting an opening of the capillary channel provided in the chamber A, is absorbed into the flow path by a capillary force, and thus the flow path is partially or entirety filled with the liquid. The position of the flow path filled with the liquid, and the amount of the liquid filling the flow path, are determined by the balance between the capillary force acting on the liquid in the flow path and the gravitational force.

In order to fill the capillary channel with the liquid by the capillary force, an air hole is formed in each of the chamber A and the chamber B to match the pressure in the two chambers with the pressure in an external environment, so as not to cause a pressure difference by the movement of the liquid.

In the state where the flow path is filled with the liquid by the capillary force, the liquid in the flow path is still by the balance among the capillary force, the atmospheric pressure and the gravitational force, and thus the liquid is not transferred from the chamber A to the chamber B. The liquid is not transferred even in the case where the sample analysis substrate is rotated so as to have a centrifugal force smaller than, or equal to, the capillary force act on the liquid in the flow path.

By contrast, in the case where the chamber B is located farther from the rotation shaft than the chamber A and the sample analysis substrate is rotated so as to have a centrifugal force stronger than the capillary force act on the liquid in the flow path as the capillary channel, the liquid in the chamber A is transferred to the chamber B by the centrifugal force.

In the case where a capillary action is used to transfer a liquid via a flow path, the flow path has a thickness of, for example, 50 μm to 300 μm. In order to form chambers or flow paths having different thicknesses, for example, spaces having different depths may be formed in the base plate 100a. Alternatively, spaces of the same depth may be formed in the base plate 100a and protruding portions having different heights may be formed on the cover plate 100b at positions corresponding to the chambers and flow paths. In this manner also, the chambers and the flow paths have different thicknesses.

As described below, a part of, or the entirety of, a flow path may be a capillary space so as to fill a part of, or the entirety of, a chamber with the held liquid with certainty. In this case, a region acting as the capillary space has a thickness of 50 μm to 300 μm as described above.

In order to transfer a liquid by a capillary force and a centrifugal force provided by a rotation, the sample analysis substrate 100 having a diameter of 60 mm may be rotated at a rotation rate in the range of 100 rpm to 8000 rpm, for example. The rotation rate is determined in accordance with the shape of each of the chambers and the flow paths, properties of the liquid, timing of transfer of, or treatment on, the liquid, or the like.

An inner surface of the flow path or the chamber on which a capillary force is to act, and an inner surface of a portion in the vicinity of a connection portion of the chamber connected with the flow path, may be treated to be hydrophilic. The hydrophilic treatment allows the capillary force to act strongly. In order to perform the hydrophilic treatment, the above-described inner surfaces may be, for example, coated with a nonion, cation, anion or amphoteric ion surfactant, treated with corona discharge, or supplied with microscopic physical recessed and protruding portions (see, for example, Japanese Laid-Open Patent Publication No. 2007-3361). In the case where the first flow path 111 through the seventh flow path 117 are spaces allowed to be filled with a liquid by a capillary action, these flow paths may be treated to be hydrophilic.

The first holding chamber 101, the second holding chamber 102, the third holding chamber 103, the first storage chamber 104, the second storage chamber 105, the reaction chamber 106, the main chamber 107 and the recovery chamber 108 are each provided with at least one air hole 122. With such a structure, the chambers are kept at the atmospheric pressure in the environment and the liquid is allowed to move between the flow paths by the capillary action and the siphon principle. The first storage chamber 104, the second storage chamber 105 and the reaction chamber 106 may each have an opening 123 usable to inject a washing solution and a substrate solution. The air hole 122 may also act as the opening 123.

The spaces of the first holding chamber 101, the second holding chamber 102, the third holding chamber 103, the first storage chamber 104, the second storage chamber 105, the reaction chamber 106, the main chamber 107 and the recovery chamber 108 are formed in the base plate 100a, and the base plate 100a is covered with the cover plate 100b. Thus, the top surface and the bottom surface of each of the spaces are formed. Namely, these spaces are defined by the inner surfaces of the substrate 100'. The first flow path 111, the second flow path 112, the third flow path 113, the fourth flow path 114, the fifth flow path 115, the sixth flow path 116 and the seventh flow path 117 are also formed in the base plate 100a, and the base plate 100a is covered with the cover plate 100b. Thus, top surfaces and bottom surfaces of these flow paths are formed. In this embodiment, the base plate 100a and the bottom plate 100b respectively define the top surfaces and the bottom surfaces. The substrate 100' may be formed of, for example, a resin such as acrylic resin, polycarbonate, polystyrene or the like.

Table 1 shows a combination of the substance or liquid to be introduced into the sample analysis substrate 100 in this embodiment at the start of sample analysis, the chamber to which the substance or liquid is to be introduced first, and the order in which the introduced substances and liquids are to be introduced into the main chamber. The combination shown in Table 1 is merely an example, and the substance or liquid to be introduced into the chamber and the order in which the substances and liquids are to be introduced into the main chamber are not limited to those shown in Table 1.

As shown in Table 1, the magnetic particle-immobilized antibody 305, a specimen containing the antigen 306 and the labeled antibody 308 are introduced into the reaction chamber 106, and the complex body 310 is generated in the reaction chamber 106. In this embodiment, among these substances, the magnetic particle-immobilized antibody 305 and the labeled antibody 308 are located as being contained in a dried agent in the reaction chamber 106 in advance. A substrate solution is introduced into the second storage chamber 105. A washing solution is introduced into the first storage chamber 104. As described below in detail, the washing solution held in the first storage chamber 104 is introduced into the main chamber 107 via the reaction chamber 106.

TABLE 1

| CHAMBER | SUBSTANCE TO BE HELD | ORDER OF INTRODUCTION INTO MAIN CHAMBER 107 |
|---|---|---|
| REACTION CHAMBER 106 | MAGNETIC PARTICLE-IMMOBILIZED ANTIBODY 305 AND LABELED ANTIBODY 308 (DRYING AGENT 125), SPECIMEN (ANTIGEN 305) | 1 |
| 1ST STORAGE CHAMBER 104 | WASHING SOLUTION | 2 |
| 2ND STORAGE CHAMBER 105 | SUBSTRATE SOLUTION | 3 |

Hereinafter, with reference to mainly FIG. 3C through FIG. 3H, the chambers and the flow paths regarding the complex body 310, the washing solution and the substrate solution will be described in the order of the introduction into the main chamber 107 shown in the table above. In FIG. 3C through FIG. 3H, the components of the sample analysis substrate 100 that are not related to, or not referred to, the description are not shown for easier understanding.

[Reaction Chamber 106]

Figure 3C:
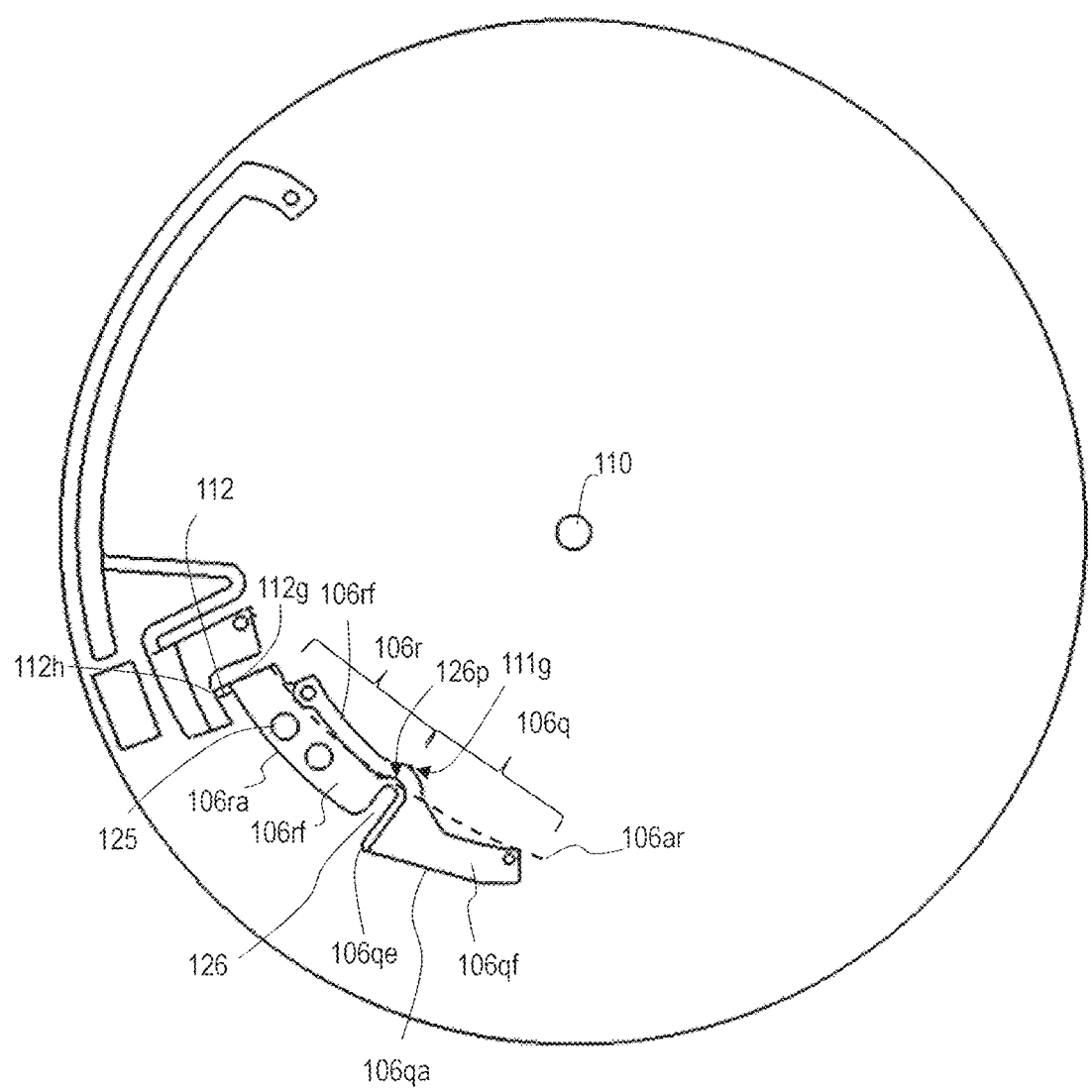
FIG. 3C is a plan view showing a structure regarding transfer of a reaction solution in the sample analysis substrate shown in FIG. 3A.

As shown in FIG. 3C, the reaction chamber 106 is provided in the sample analysis substrate 100. As described above with reference to FIG. 1, the reaction chamber 106 is a reaction field in which the magnetic particle-immobilized antibody 305, the specimen containing the antigen 306 and the labeled antibody 308 are reacted to form the complex body 310.

In this embodiment, the reaction chamber 106 includes a first portion 106q and a second portion 106r.

In this embodiment, the first portion 106q and the second portion 106r are generally aligned in a circumferential direction of a circle centered around the rotation shaft 11. A wall portion 126 formed of an inner surface of the substrate 100' is located between the first portion 106q and the second portion 106r. The wall portion 126 protrudes toward the rotation shaft 110 and separates the first portion 106q and the second portion 106r from each other. The first portion 106q and the second portion 106r are in contact with each other on a position on a radius connecting the rotation shaft 110 and a point 126p, in the wall portion 126, that is closest to the rotation shaft 110.

The first portion 106q includes a first region 106qf, which is a non-capillary space, and a second region 106qe, which is a capillary space. The first region 106qf and the second region 106qe are adjacent to each other, and spaces thereof are in communication with each other. The second region 106qe of the first portion 106q is a narrow region along the wall portion 126. The second region 106qe is in contact with an outermost side surface 106qa, which is farthest from the rotation shaft 110 among side surfaces of the first portion 106q. By contrast, the space of the first region 106qf is sufficiently large to hold a specimen. In the first portion, the first region 106*qf* is closer to the rotation shaft 110 than the second region 106*qe*.

The second portion 106*r* includes a first region 106*rf*, which is a non-capillary space, and a second region 106*re*, which is a capillary space. The first region 106*rf* and the second region 106*re* are adjacent to each other, and spaces thereof are in communication with each other. The first region 106*rf* is located along a side surface facing an outermost side surface 106*ra*, which is farthest from the rotation shaft 110 among side surfaces defining the second portion 106*r*. Specifically, the first region 106*rf* is located closer to the rotation shaft 110 than the second region 106*re*.

The first region 106*qf* of the first portion 106*q* is connected with the first region 106*rf* of the second region 106*r*. The second region 106*re* of the second portion 106*r* is connected with the second region 106*re* of the second region 106*r*.

As represented by the dashed line in FIG. 3C, the first portion 106*q* and the second portion 106*r* each include a portion located farther from an arc 126*ar*, which has, as a radius, a line segment connecting the rotation shaft 110 and the point 126*p*, in the wall portion 126, closest to the rotation shaft 110. Specifically, a part of the first region 106*qr* of the first portion 106*q* and a part of the second region 106*re* of the second portion 106*r* are located outer to the arc 126*ar*.

As described above, in the reaction chamber 106, the non-capillary spaces and the capillary spaces have different thicknesses from each other.

In this embodiment, the dried agent 125 containing the magnetic particle-immobilized antibody 305 and the labeled antibody 308 both in a dried state is held in the second region 106*re* of the second portion 106*r* in advance. A liquid containing a specimen solution that contains the antigen 306 is introduced into the first region 106*qf* of the first portion 106*q* of the reaction chamber 106 at the start of sample analysis. When the introduced liquid contacts the second region 102*qe* of the first portion 106*q*, the introduced liquid fills the second region 102*qe* by a capillary force and further fills the second region 102*re* of the second portion. This causes the liquid to contact the dried agent 125, and thus the magnetic particle-immobilized antibody 305 and the labeled antibody 308 in the dried agent 125 are eluted or dispersed into the liquid. As a result, the antigen 306, the magnetic particle-immobilized antibody 305 and the labeled antibody 308 are mixed together in the liquid to form the complex body 310.

In the case where the sample analysis substrate 100 is provided with the dried agent 125, it is preferred that the dried agent 125 is held in the capillary space of the reaction chamber 106 (in the second region 106*re*) for the following reason. A liquid in a non-capillary space of a reaction chamber is moved to a capillary space by a capillary force. The force acting on the liquid at this point is smaller than a centrifugal force provided by the rotation of the sample analysis substrate 100. Therefore, if the dried agent 125 is held in a non-capillary space (in the first region 106*qf*), the magnetic particle-immobilized antibody 305 in the dried agent 125 does not all move to the capillary space and may partially stay in the non-capillary space.

The manner of introducing the specimen solution containing the antigen 306, the magnetic particle-immobilized antibody 305 and the labeled antibody 308 into the reaction chamber 106 is not limited to the above-described manner. The sample analysis substrate 100 may not be provided with the dried agent 125, in which case the magnetic particle-immobilized antibody 305, and the specimen containing the antigen 306, and the labeled antibody 308 may be introduced into the first region 106*qf* of the first portion 106*q* at the start of sample analysis. Alternatively, the sample analysis substrate 100 may include, for example, chambers respectively usable to hold the magnetic particle-immobilized antibody 305, the specimen containing the antigen 306 and the labeled antibody 308 and flow paths (e.g., capillary channels) coupling the respective chambers and the reaction chamber 106 to each other. Certain amounts of the specimen containing the antigen 306 and the labeled antibody 308 may be put into the respective chambers, and the magnetic particle-immobilized antibody 305, the specimen containing the antigen 306 and the labeled antibody 308 injected into the respective chambers may be transferred to, and mixed together in, the reaction chamber 106 to form the complex body 310.

[Second Flow Path 112]

A solution containing the complex body 310 in the reaction chamber 106 is transferred to the main chamber 107 via the second flow path 112. The second flow path 112 has an opening 112*g* and an opening 112*h*. It is preferred that the opening 112*g* of the second flow path 112 is provided in an outermost side surface 106*ra* farthest from the rotation shaft 110 among side surfaces defining the second region 106*re* of the second portion 106*r* of the reaction chamber 106 or in an adjacent side surface among the side surfaces defining the reaction chamber 106 that is adjacent to the outermost side surface 106*ra*, more specifically, in a part of such an adjacent side surface including a connection portion connected with the outermost side surface 106*ra*. A reason for this is that with such an arrangement, when the liquid in the reaction chamber 106 is transferred to the main chamber 107, the liquid is suppressed from remaining in the reaction chamber 106. FIG. 3C shows an example in which the opening 112*g* is located in a part of the outermost side surface 106*a*.

The opening 112*h* of the second flow path 112 is located farther from the rotation shaft 110 than the opening 112*g*. As described below, the opening 112*h* is connected with a side surface of the main chamber 107. Since the opening 112*h* is located farther from the rotation shaft 110 than the opening 112*g*, when the sample analysis substrate 100 is rotated, the solution containing the complex body 310 in the reaction chamber 106 is transferred to the main chamber 107 via the second flow path 112 by a centrifugal force. The second flow path 112 may be a capillary channel or a flow path in which a liquid is transferable by a gravitational force.

[Main Chamber 107]

Figure 3D:
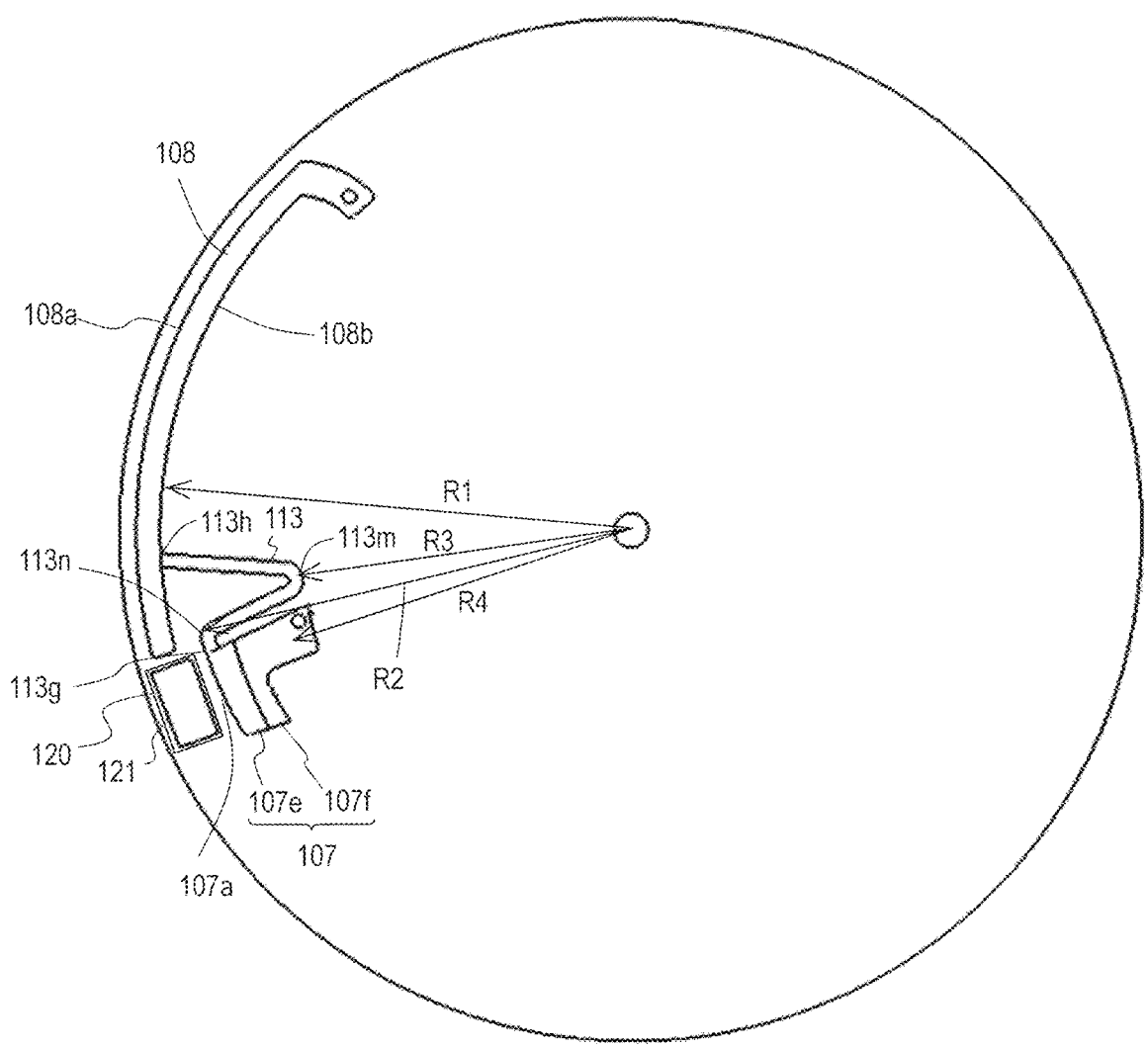
FIG. 3D is a plan view showing a main chamber and a siphon structure of a third flow path in the sample analysis substrate shown in FIG. 3A.

As shown in FIG. 3D, the main chamber 107 is a field in which the solution containing the complex body 310 is subjected to the B/F separation. In order to perform the B/F separation, the sample analysis substrate 100 includes a magnet accommodation chamber 120 located in the substrate 100' and a magnet 121 located in the magnet accommodation chamber 120.

The magnet accommodation chamber 120 is located close to the space of the main chamber 107 in the sample analysis substrate 100. More specifically, the magnet accommodation chamber 120 is located close to an outermost side surface 107*a* farthest from the rotation shaft 110 among a plurality of side surfaces of the main chamber 107. Alternatively, the magnet accommodation chamber 120 in the sample analysis substrate 100 may be located at a position close to a surface of the main chamber 107 other than the outermost side surface 107*a*, for example, the top surface or the bottom surface thereof. Namely, as long as the magnetic particles are captured on a wall of the main chamber 107 by the magnet 121 located in the magnet accommodation chamber 120, there is no specific limitation on the position of the magnet 121. The magnet 121 may be structured to be detachable in accordance with the state of the B/F separation, may be provided in the substrate 100' so as to be undetachable from the magnet accommodation chamber 120, or may be provided on the sample analysis device 200.

Figure 3E:
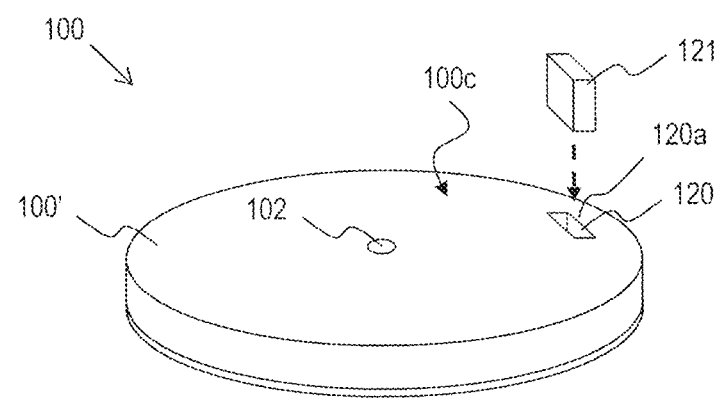
FIG. 3E is an isometric view showing an example of method for holding a magnet in the sample analysis substrate.

In the case where the magnet 121 is detachable, as shown in, for example, FIG. 3E, the substrate 100' may include the magnet accommodation chamber 120 of a recessed type that has an opening 120a at the main surface 100c. The magnet accommodation chamber 120 has a space capable of accommodating the magnet 121. The magnet 121 may be inserted into the magnet accommodation chamber 120 via the opening 120a to be mounted on the substrate 100'. The opening 120a of the magnet accommodation chamber 120 may be provided at the main surface 100d or a side surface located between the two main surfaces 100c and 100d.

In the case where the magnet 121 is provided on the sample analysis device 200, a magnetic unit including the magnet 121, for example, may be provided on the turntable 201a of the sample analysis device 200. In this case, when a user puts the sample analysis substrate 100 at a predetermined position on the turntable 201a (magnetic unit), the magnet 121 is located at a position where the magnetic particles may be captured on the wall of the main chamber 107. In another example in which the magnet 121 is provided on the sample analysis device 200, the sample analysis device 200, for example, may include the magnet 121 and a driving mechanism that moves the magnet 121. In this case, the sample analysis substrate 100 may include an accommodation chamber usable to hold the magnet 121, and the driving mechanism may insert the magnet 121 into the accommodation chamber of the sample analysis substrate 100 or remove the magnet 121 from the accommodation chamber in accordance with the state of the B/F separation.

When the reaction solution is transferred to the main chamber 107 via the second flow path 112, an assembly of the complex body 310 and the unreacted magnetic particle-immobilized antibody 305 (hereinafter, such an assembly will be referred to simply as a "magnetic particle 311") gathers and is captured on the outermost side surface 107a or in the vicinity thereof by a magnetic force the magnet 121 located close to the outermost side surface 107a.

The space of the main chamber 107 may include a first region 107f and a second region 107e adjacent to, and connected with, the first region 107f. The first region 107f is a non-capillary space in which a liquid is movable by a gravitational force, and the second region 107e is a capillary space acted on by a capillary force. Therefore, the first region 107f is thicker than the second region 107e, and the space of the first region 107f is larger than the space of the second region 107e. Specifically, the first region 107f and the second region 107e each have a thickness in the range described above regarding the thickness of a flow path.

It is preferred that the second region 107e is in contact with the outermost side surface 107a, and that at least a part of the first region 107f is closer to the rotation shaft 110 than the second region 107e. An opening 117h of the second flow path 112 is provided in one of the side surfaces in contact with the first region 107f.

The liquid in the main chamber 107 is transferred to the recovery chamber 108 via the third flow path 113. As described below, an opening 113g of the third flow path 113 is provided on a side surface in contact with the second region 102e so as to be connected with the space of the second region 102e.

In the main chamber 107, the first region 107f is a space in which a liquid is movable by a gravitational force. Therefore, the first region 107f may have a necessary size of space with certainty. The second region 107e is a capillary space, and thus is filled, without fail, with a part of the liquid held in the main chamber 107. Therefore, the third flow path 113 contacts the second region 107e, and thus all the liquid in the main chamber 107 is transferred to the recovery chamber 108 via the third flow path 113. Since the washing solution and the substrate solution are introduced, as well as the reaction solution, into the main chamber 107, it is important as features that the main chamber 107 has a sufficient size of space to hold these liquids and is capable of transferring the held liquids to the recovery chamber 108 with certainty when necessary.

[Third Flow Path 113]

The third flow path 113 has the opening 113g and an opening 113h. The opening 113g is connected with the main chamber 107, and the opening 113h is connected with the recovery chamber 108.

It is preferred that the opening 113g of the third flow path 113 is provided in the outermost side surface 107a farthest from the rotation shaft 110 among the side surfaces of the main chamber 107 or in an adjacent side surface among the side surfaces of the main chamber 107 that is adjacent to the outermost side surface 107a, more specifically, in a part of such an adjacent side surface including a connection portion connected with the outermost side surface 107a. FIG. 3D shows an example in which the opening 113g is located in the adjacent side surface adjacent to the outermost side surface 107a. As described above, the opening 113g is connected with the second region 107e of the main chamber 107.

The opening 113h of the third flow path 113 is located farther from the rotation shaft 110 than the opening 113g. It is preferred that the opening 113h is provided in an innermost side surface 108b closest to the rotation shaft 110 among the side surfaces of the recovery chamber 108 or in an adjacent side surface among the side surfaces of the recovery chamber 108 that is adjacent to the innermost side surface 108b, more specifically, at a position in such an adjacent side surface that is close to the innermost side surface 108b. FIG. 3D shows an example in which the opening 113h is located in a part of the innermost side surface 108b.

The third flow path 113 is capable of absorbing the liquid held in the main chamber 107 by a capillary action. The third flow path 113 is thinner than the second region 107e of the main chamber 107. This allows a capillary force to act on the third flow path 113 more strongly than on the second region 107e of the main chamber 107, and thus a part of the liquid in the second region 107e of the main chamber 107 is absorbed into the third flow path 113.

The third flow path 113 may further control the movement of the liquid by the siphon principle. For this purpose, the third flow path 113 includes a first bending portion 113n and a second bending portion 113m to form a siphon structure. The first bending portion 113n is protruding in a direction away from the rotation shaft 110, and the second bending portion 113m is protruding toward the rotation shaft 110. The first bending portion 113n is located between the second bending portion 113m and the main chamber 107, which is closer to the rotation shaft 110 among the main chamber 107 and the recovery chamber 108 connected to each other by the third flow path 113.

Herein, the "siphon principle" refers to control on liquid transmission by the balance between a centrifugal force applied to the liquid by the rotation of the sample analysis substrate 100 and a capillary force of the flow path.

In the case where, for example, the third flow path 113 is a capillary channel that does not have the siphon structure, the liquid transferred from the reaction chamber 106 to the main chamber 107 via the second flow path 112 by a centrifugal force provided by the rotation of the sample analysis substrate 100 fills the third flow path 113 by a capillary force of the third flow path 113. If the rotation of the sample analysis substrate 100 is continued in this state, the liquid is not held in the main chamber 107 and is undesirably transferred to the recovery chamber 108 via the third flow path 113. At this point, the sample analysis substrate 100 is rotating at a rotation rate that provides a centrifugal force stronger than the capillary force of the third flow path 113.

By contrast, in the case where the third flow path 113 has the siphon structure, the liquid transferred from the reaction chamber 106 to the main chamber 107 is absorbed into the third flow path 113 by a capillary force of the third flow path 113. However, in the case where the sample analysis substrate 100 continues rotating at a rotation rate that provides a centrifugal force stronger than the capillary force of the third flow path 113, the third flow path 113 is not entirety filled with the liquid because the centrifugal force is stronger than the capillary force applied to the liquid. Namely, the third flow path 113 is filled with the liquid merely to a height that is equal to the height of the liquid surface of the liquid in the main chamber 107.

In the case where the sample analysis substrate 100 is rotating at a rotation rate that provides a centrifugal force weaker than the capillary force of the third flow path 113, the third flow path 113 is filled with the liquid by the capillary force, and the liquid does not move any further by the capillary force.

In order to transfer the liquid in the main chamber 107 to the recovery chamber 108, the sample analysis substrate 100 is rotated at a rotation rate that provides a centrifugal force weaker than, or equal to, the capillary force of the third flow path 113 (encompassing a rotation rate of zero). Thus, the third flow path 113 is entirely filled with the liquid by the capillary force. Then, the sample analysis substrate 100 is rotated at a rotation rate that provides a centrifugal force stronger than the capillary force of the third flow path 113. As a result, the liquid in the main chamber 107 is transferred to the recovery chamber 108.

In this manner, in the case where the third flow path 113 has a siphon structure, the reaction solution, the washing solution and the substrate solution are once held in the main chamber 107, and the B/F separation, washing of the magnetic particle, and the reaction with the substrate solution are appropriately performed in the main chamber 107.

FIG. 3D will be referred to. In order to cause the third flow path 113 to have the siphon structure, it is preferred that R1>R2 (condition 1) is fulfilled where R1 is the distance between the rotation shaft 110 and the innermost side surface 108b closest to the rotation shaft 110 among the side surfaces of the recovery chamber 108 located far from the rotation shaft 110, and R2 is the distance between the rotation shaft 110 and a position in the first bending portion 113n that is farthest from the rotation shaft 110.

In the case where the liquid held in the main chamber 107 located close to the rotation shaft 110 is eccentrically held along the side surface of the main chamber 107 by the centrifugal force, it is preferred that R4>R3 (condition 2) is fulfilled where R4 is the distance between the rotation shaft 110 and the liquid surface of the liquid, and R3 is the distance between the rotation shaft 110 and a position in the second bending portion 113m that is closest to the rotation shaft 110.

In the case where the third flow path 113 fulfills the conditions 1 and 2 and thus the reaction liquid is transferred from the reaction chamber 106 to the main chamber 107, the sample analysis substrate 100 may be rotated at a rotation rate that provides a centrifugal force stronger than the capillary force applied to the liquid in the third flow path 113. With such an arrangement, the reaction solution or the washing solution transferred to the main chamber 107 is prevented from being transferred to the recovery chamber 108 as it is.

[Recovery Chamber 108]

The recovery chamber 108 stores the reaction solution, other than the magnetic particles 311, that is transferred from the main chamber 107 via the third flow path 113, and also stores the used washing solution transferred from the main chamber 107 via the third flow path 113. The recovery chamber 108 has a space of a capacity larger than the sum of the amount of reaction solution described above and a total amount of used washing solution corresponding to the number of times of washing. It is preferred that a main portion of the recovery chamber 108 holding the liquid is located farther from the rotation shaft 110 than the main chamber 107.

[First Storage Chamber 104]

Figure 3F:
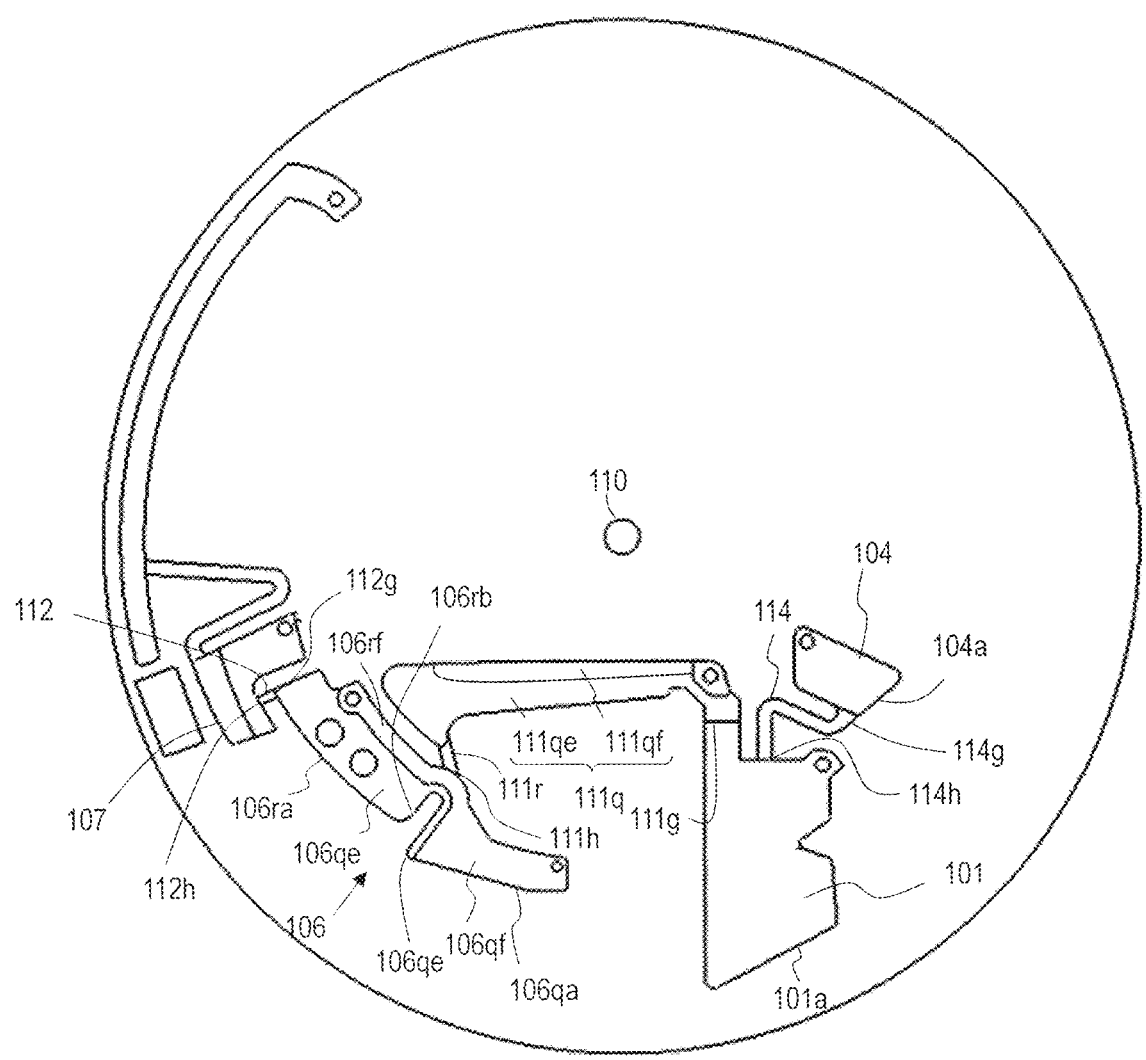
FIG. 3F is a plan view showing a structure regarding transfer of a washing solution in the sample analysis substrate shown in FIG. 3A.

FIG. 3F will be referred to. The first storage chamber 104 stores the washing solution usable for washing for the B/F separation. As described below in detail, in the sample analysis system in this embodiment, the complex body 310 may be washed a plurality of times for the B/F separation. Therefore, the first storage chamber 104 has a space capable of holding a total amount of washing solution corresponding to the number of times of washing.

[Fourth Flow Path 114]

The washing solution in the first storage chamber 104 is transferred to the first holding chamber 101 via the fourth flow path 114. The fourth flow path 114 has an opening 114g and an opening 114h. It is preferred that the opening 114g of the fourth flow path 114 is provided in an outermost side surface 104a farthest from the rotation shaft 110 among the side surfaces of the first storage chamber 104 or in an adjacent side surface among the side surfaces of the first storage chamber 104 that is adjacent to the outermost side surface 104a, more specifically, in a part of such an adjacent side surface including a connection portion connected with the outermost side surface 104a. FIG. 3F shows an example in which the opening 114g is located in the connection portion, of the adjacent side surface, connected with the outermost side surface 104a.

The opening 114h of the fourth flow path 114 is located farther from the rotation shaft 110 than the opening 114g. As described below, the opening 114h is connected with a side surface of the first holding chamber 101. Since the opening 114h is located farther from the rotation shaft 110 than the opening 114g, when the sample analysis substrate 100 is rotated, the washing solution in the first storage chamber 104 is transferred to the first holding chamber 101 via the fourth flow path 114 by a centrifugal force. The fourth flow path 114 may be a capillary channel or a flow path in which a liquid is transferable by a gravitational force.

[First Holding Chamber 101]

The first holding chamber 101 holds all the washing solution stored in the first storage chamber 104. Then, in order to wash the complex body 310 in the main chamber 107, the first holding chamber 101 transfers a part of the washing solution to the reaction chamber 106 and holds the remaining part of the washing solution. As described below, the amount of the washing solution needed for one cycle of washing is weighed out by use of the first flow path 111. Therefore, the first holding chamber 101 has a capacity larger than, or equal to, that of the first flow path 111, more specifically, has a capacity larger than, or equal to, the total amount of washing solution corresponding to the number of times of washing (e.g., if the washing is to be performed twice, a capacity larger than, or equal to, twice the capacity of the first flow path 111, and if the washing is to be performed three times, a capacity larger than, or equal to, three times the capacity of the first flow path 111).

The opening 114h of the fourth flow path 114 is provided in one inner side surface that faces an outermost side surface 103a of the first holding chamber 101 while having the space usable to hold the liquid between the one inner side surface and the outermost side surface 101a.

[First Flow Path 111]

As described above, the first flow path 111 connects the first holding chamber 101 and the reaction chamber 106 to each other. Therefore, in the case where the washing solution is to be introduced into the first storage chamber 104, the washing solution is once transferred to the reaction chamber 106 and then is transferred to the main chamber 107.

The first flow path 111 includes a first portion 111q and a second portion 111r connected with the first portion 111q. The second portion 111r is a capillary channel. The first portion 111q has an opening 111g, and is connected with the first holding chamber 101. A part of the first holding chamber 101 and a part of the first flow path 111 are generally aligned in a radial direction of a circle centered around the rotation shaft 110, with the opening 111g being located between these parts. The second portion 111r has a second opening 111h, and is connected with the first region 106qf of the first portion 106q of the reaction chamber 106. The second opening 111h is closer to the rotation shaft 110 than the opening 112g of the second flow path 112.

The first portion 111q of the first flow path 111 includes a first region 111qe and a second region 111qf. In this embodiment, the first portion 111q has a shape extending in a direction oblique with respect to the radial direction of the sample analysis substrate 100. The second region 111qf of the first portion 111q is located closer to the rotation shaft 110 than the first region 111qe. The first region 111qe is a capillary space, and the second region 111qf is not a capillary space allowed to be filled with a liquid by a capillary force. For example, the second region 111qf is thicker than the first region 111qe. Therefore, the second region 11qf is also filled with the liquid, which increases the amount of the washing solution to be weighed out.

The second region 111qf is provided with an air hole 122. The second region 111qf also act as an air path guaranteeing the movement of the air. Specifically, since the second region 111qf is provided, even if air bubbles are generated in the liquid held in the first region 111qe for some reason, the air bubbles easily move to the second region 111qf be removed from the liquid. With such an arrangement, in the case where the sample analysis substrate 100 is rotated, specifically, the air bubbles are suppressed from entering the second portion 111r. Thus, the movement of the liquid is suppressed from being disturbed.

Figure 3G:
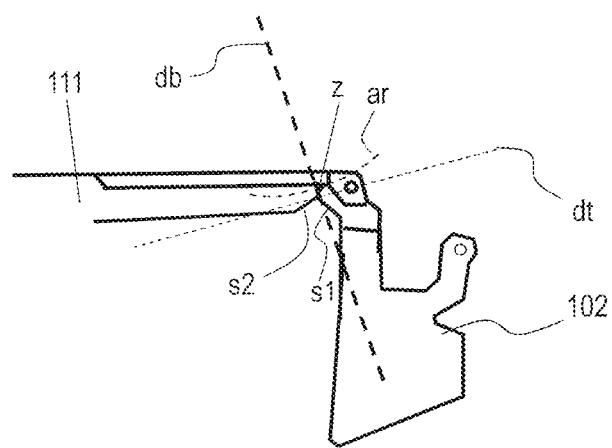
FIG. 3G is a partial enlarged plan view of a structure of a first flow path in the sample analysis substrate.

As described below in detail, in the case where the rotation angle of the sample analysis substrate 100 is changed to an angle at which the washing solution contacts an opening 116g in the state where the washing solution is held in the first holding chamber 101, the first flow path 111 is filled with the washing solution by a capillary action except for the second region 116qf. In this state, the sample analysis substrate 100 is rotated at a rotation rate that provides a centrifugal force stronger than the capillary force applied to the washing solution in the first flow path 111. In this case, as shown in FIG. 3G, the washing solution is divided, along a straight line db connecting the rotation shaft 110 and position z on a plane perpendicular to the rotation shaft 110, into washing solution transferred to the first holding chamber 101 and washing solution returning to the first flow path 111. As shown in FIG. 3G, the reference position z is defined by the border between two side surfaces s1 and s2. The side surfaces s1 and s2 are respectively located farther from the rotation shaft 110 than the space of the first holding chamber 101 and the space of the first flow path 111. More specifically, the side surface or plane s1 is inclined toward the first holding chamber 101, and the side surface or plane s2 is inclined toward the second holding chamber, from a tangential direction dt of an arc ar centered around the rotation shaft 110. As a result of the division, the amount of washing solution needed for one cycle of washing is weighed out and is transferred to the main chamber 107. The washing solution transferred to the main chamber 107 is transferred to the recovery chamber 108 via the third flow path 113 as described above.

[Second Storage Chamber 105]

Figure 3H:
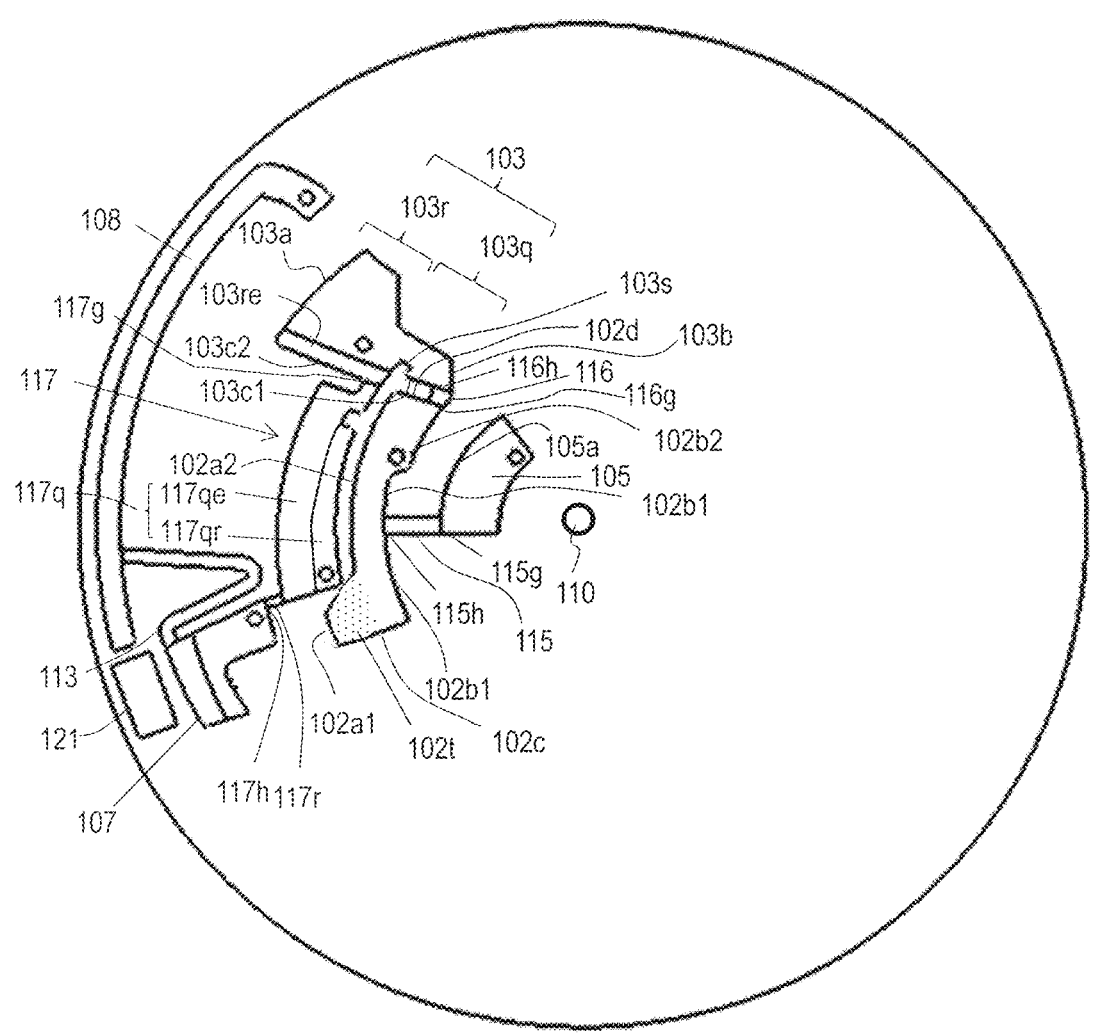
FIG. 3H is a plan view showing a structure regarding transfer of a substrate solution in the sample analysis substrate shown in FIG. 3A.

FIG. 3H will be referred to. The second storage chamber 105 stores the substrate solution at the start of the analysis performed by use of the sample analysis system. There is no specific limitation on the shape of the second storage chamber 105, and the second storage chamber 105 may have any shape.

[Fifth Flow Path 115]

The fifth flow path 115 connects the second storage chamber 105 and the second holding chamber 102 to each other. The fifth flow path 115 extends in, for example, the radial direction of the circle centered around the rotation shaft 110, and is a capillary channel. The fifth flow path 115 has an opening 115g and an opening 115h. It is preferred that the opening 115g is provided in an outermost side surface 105a farthest from the rotation shaft 110 among the side surfaces of the second storage chamber 105 or in an adjacent side surface among the side surfaces of the second storage chamber 105 that is adjacent to the outermost side surface 105a, more specifically, at a position in such an adjacent side surface that is close to the outermost side surface 105a. In this embodiment, the opening 115g is provided in the outermost side surface 105a. The opening 115h is connected with the second holding chamber 102.

[Second Holding Chamber 102]

The second holding chamber 102 stores the substrate solution transferred from the second storage chamber 105 during the B/F separation including the washing after the start of the analysis performed by use of the sample analysis system. The second holding chamber 102 is located farther from the rotation shaft 110 than the second storage chamber 105. The second holding chamber 102 has a first outer side surface 102a1 and a second outer side surface 102a2, and a first inner side surface 102b1 and a second inner side surface 102b2 enclosing the space usable to hold the substrate solution. The first outer side surface 102a1 and the second outer side surface 102a2 do not overlap each other in the radial direction, and the first outer side surface 102a1 is located farther from the rotation shaft 110 than the second outer side surface 102a2. The first inner side surface 102b1 and the second inner side surface 102b2 do not overlap each other in the radial direction, and the first inner side surface 102b1 is located farther from the rotation shaft 110 than the second inner side surface 102b2.

The second first holding chamber 102 further has an adjacent side surface 102c adjacent to the first outer side surface 102a1 and the first inner side surface 102b1, and an adjacent side surface 102d adjacent to the second outer side surface 102a2 and the second inner side surface 102b2. The space of the second holding chamber 102 has a shape extending in a circumferential direction while being sandwiched between the adjacent side surface 102c and the adjacent side surface 102d.

As described below, in this embodiment, the opening 116g of the sixth flow path 116 is provided in the first inner side surface 102b1. The opening 116g of the sixth flow path 116 described below in detail is located adjacent to a connection position in the adjacent side surface 102d connected with the second inner side surface 102b2. Namely, the sixth flow path 116 is located at a position in the adjacent side surface 102d that is close to the rotation shaft 110. With such a structure, a majority part of the space of the second holding chamber 102 is located farther from the rotation shaft 110 than an opening 116h of the sixth flow path 116. Therefore, regardless of the rotation angle at which the sample analysis substrate 100 is held, the substrate solution held in the second holding chamber 102 is suppressed from being transferred to the third holding chamber 103 via the sixth flow path 116.

The first outer side surface 102a1 is located far from the rotation shaft 110, and the space of the second holding chamber 102 includes a protruding portion 102t contacting the first outer side surface 102a1 and protruding outward. Therefore, the substrate solution is held in the protruding portion 102t of the space of the second holding chamber 102. Thus, the liquid surface of the substrate solution held in the second holding chamber 102 is separated from the opening 111g of the sixth flow path 116, and the substrate solution is suppressed with more certainty from being transferred to the third holding chamber 103 via the sixth flow path 116.

[Sixth Flow Path 116]

The sixth flow path 116 connects the second holding chamber 102 and the third holding chamber 103 to each other. The sixth flow path 116 has the opening 116g and the opening 116h. The opening 116g is provided in the adjacent side surface 102d of the second holding chamber 102. The opening 116h is provided in one of the side surfaces of the third holding chamber 103. The sixth flow path 116 is a flow path in which a liquid is movable by a gravitational force.

[Third Holding Chamber 103]

The third holding chamber 103 holds the substrate solution transferred from the second holding chamber 102 via the sixth flow path 116. The third holding chamber 103 includes a first portion 103q adjacent to the second holding chamber 102 in the circumferential direction and a second portion 103r adjacent to the seventh flow path 117 in the circumferential direction. The first portion 103q and the second portion 103r are aligned in the radial direction. The third holding chamber 103 is close to the adjacent side surface 101d of the second holding chamber 102.

The third holding chamber 103 has an outermost side surface 103a farthest from the rotation shaft 110 and a second adjacent side surface 103c2 adjacent to the outermost side surface 103a. The third holding chamber 103 has an innermost side surface 103b closest to the rotation shaft 110 and a first adjacent side surface 103c1 adjacent to the innermost side surface 103b. The first adjacent side surface 103c1 and the second adjacent side surface 103c2 are located on the same side with respect to the space of the third holding chamber 103, namely, are located to face the second holding chamber 102 and the seventh flow path 117. A recessed portion 103s is formed between the first adjacent side surface 103c1 and the second adjacent side surface 103c2, and the recessed portion 103s separates the first adjacent side surface 103c1 and the second adjacent side surface 103c2 from each other.

The first portion 103q of the third holding chamber 103 has the innermost side surface 103b and the first adjacent side surface 103c1, and the second portion 103r has the outermost side surface 103a and the second adjacent side surface 103c2.

The opening 116h of the sixth flow path 116 is provided in the first portion 103q of the third holding chamber 103, more specifically, at a position in the first adjacent side surface 103c1 that is close to the innermost side surface 103b.

An opening 117g of the seventh flow path 117 is provided in the second portion 103r, more specifically, at a position in the second adjacent side surface 103c2 that is away from the outermost side surface 103a, still more specifically, at a position in the second adjacent side surface 103c2 that is closest to the rotation shaft 110. As described below, in the case where the seventh flow path 117 is a capillary channel, the second portion 103r may include a capillary space 103re connecting the outermost side surface 103a with a portion, of the seventh flow path 117, in which the opening 117g is located. In this case, it is preferred that the capillary space 103re is located along the second adjacent side surface 10c2.

[Seventh Flow Path 117]

The seventh flow path 117 includes a first portion 117q and a second portion 117r, and has the opening 117g and the opening 117h. One of two ends of the first portion 117q and one of two ends of the second portion 117r are connected to each other. The opening 117g is located at the other end of the first portion 117q, and is connected with the second adjacent side surface 103c2 of the third holding chamber 103 as described above. The opening 117h is located at the other end of the second portion 117r, and is connected with the main chamber 107. The second portion 117r is a capillary channel.

The first portion 117q includes a first region 117qe and a second region 117qf. In this embodiment, the first portion 117q has a shape extending in the circumferential direction. The second region 117qf is located closer to the rotation shaft 110 than the first region 117qe. The first region 117qe is a capillary channel, and the second region 117qf is not a capillary space allowed to be filled with a liquid by a capillary action. For example, the second region 117qf is thicker than the first region 117qe. When the first region 117qe is filled with a liquid by a capillary action, the second region 117qf is not filled with a liquid. The second region 117qf is provided with an air hole 122. It is preferred that the first region 117qe is thicker than the capillary space 103re of the second holding chamber 103. With such an arrangement, the substrate solution held in the capillary space 103re of the third holding chamber 103 is absorbed into the seventh flow path 117.

The opening 117g is located closer to the rotation shaft 110 than the opening 117h. In order to transfer substantially all the liquid in the seventh flow path 117 to the third holding chamber 103, it is preferred that various portions of the seventh flow path 117 are located as far as the opening 117g from the rotation shaft 110 or are located farther from rotation shaft 110 than the opening 117g. With such an arrangement, when the substrate solution filling the seventh flow path 117 is subjected to a centrifugal force stronger than the capillary force applied to the substrate solution in the seventh flow path 117, all the substrate solution in the seventh flow path 117 is transferred to the main chamber 107.

The total capacity of the first region 117qe of the first portion 117q and the second region 117r corresponds to the amount of the substrate solution to be used for the analysis. The first region 117qe and the second region 117r are filled with the substrate solution by a capillary force, and thus the substrate solution is weighed out.

Like in the case of the first path 111, the second region 117qf of the first portion 117q acts as an air path. When air bubbles are generated in the substrate solution held in the first region 117qe of the first portion 117q for some reason, the air bubbles easily move to the second region 117qf to be removed from the liquid. With such an arrangement, in the case where the sample analysis substrate 100 is rotated, specifically, the air bubbles are suppressed from entering the second portion 117r. Thus, the movement of the substrate solution is suppressed from being disturbed.

In the above example, the first region 117qe of the first portion 117q and the second portion 117r in the seventh flow path 117 are respectively a capillary space and a capillary channel. Alternatively, these spaces may be a space and a flow path in which a liquid is movable by a gravitational force.

(Operation of the Sample Analysis System 501)

Figure 4:
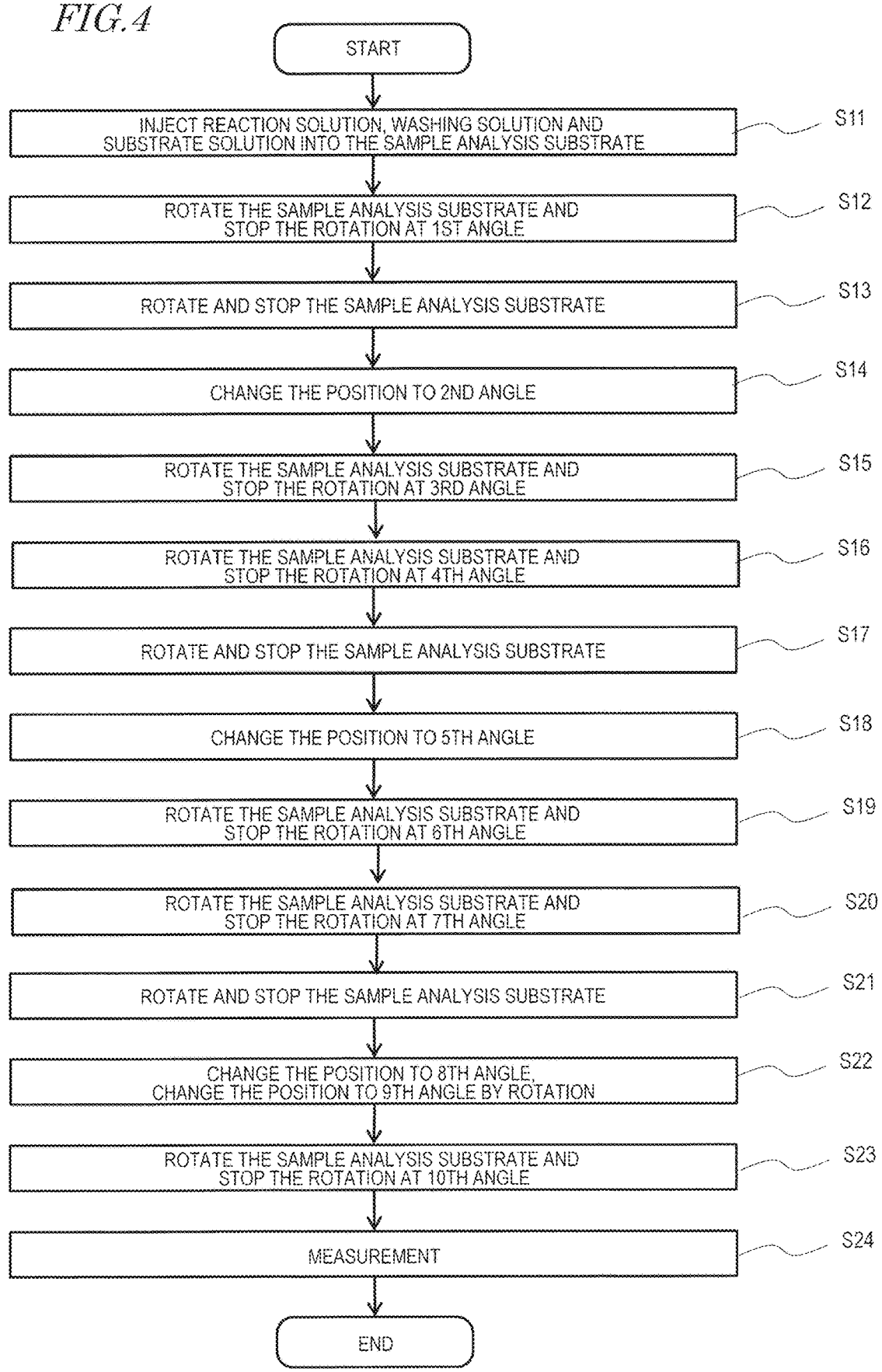
FIG. 4 is a flowchart showing an example of operation of the sample analysis system.

An operation of the sample analysis system 501 will be described. FIG. 4 is a flowchart showing an operation of the sample analysis system 501. A program defining a procedure that controls each of parts of the sample analysis system 501 in order to operate the sample analysis system 501 is stored on, for example, a memory of the control circuit 205. The program is executed by an operator to realize the following operation. Before the steps described below, the sample analysis substrate 100 is mounted on the sample analysis device 200 to detect the origin of the sample analysis substrate 100. The dried agent 125 containing the magnetic particle-immobilized antibody 305 and the labeled antibody 308 is held in advance in the second region 106re of the second portion 106r of the reaction chamber 106. In the following procedure, the sample analysis substrate is, for example, always rotated clockwise. It should be noted that the rotation direction of the sample analysis substrate is not limited to clockwise and may be counterclockwise.

[Step S11]

Figure 5:
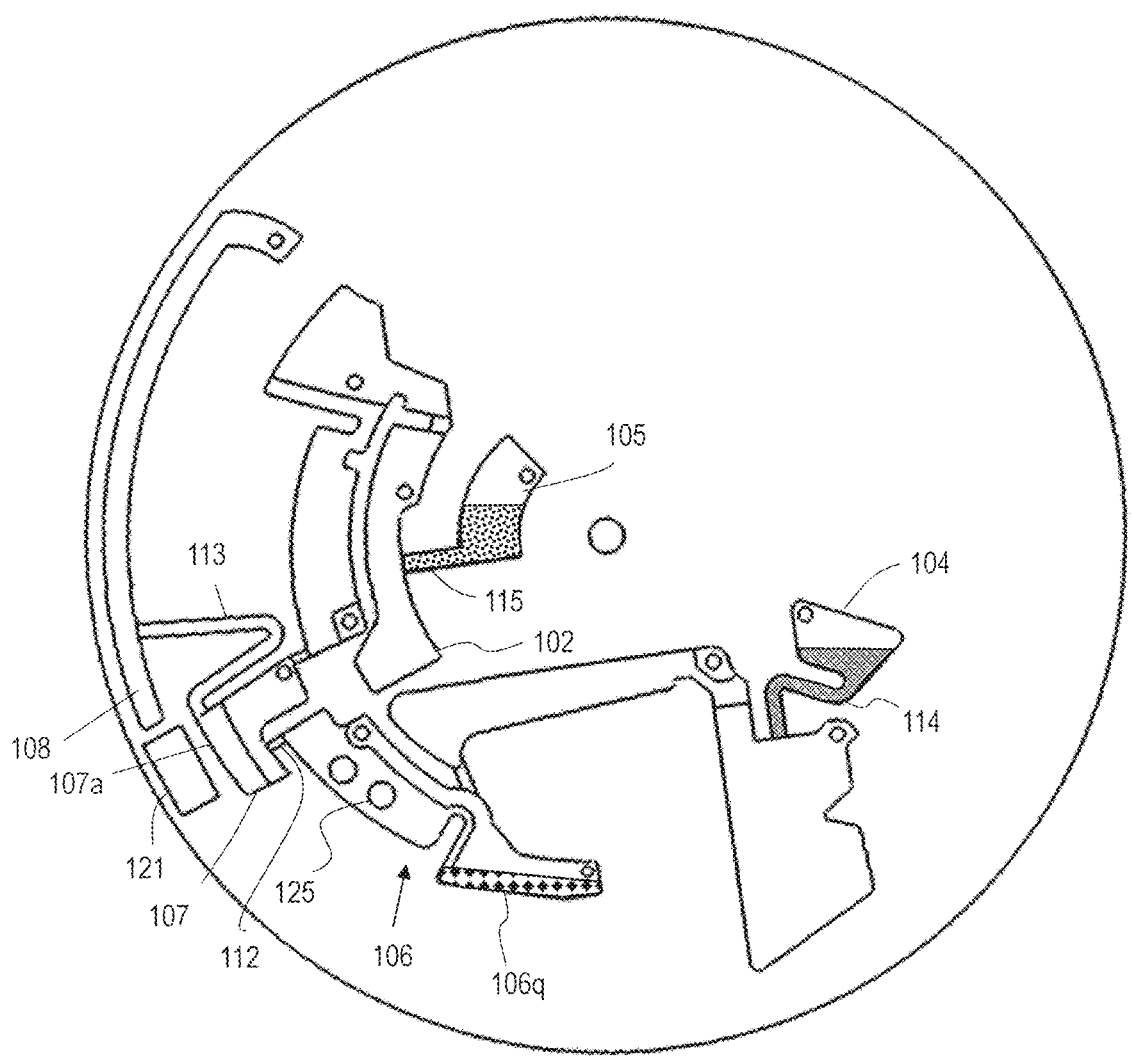
FIG. 5 schematically shows an example of angle at which the sample analysis substrate is stopped and an example of position of a liquid during the operation of the sample analysis system.

First, as shown in FIG. 5, the washing solution and the substrate solution are respectively introduced into the first storage chamber 104 and the second storage chamber 105. The substrate solution contains a substrate substance that causes light emission, fluorescence or change of the absorption wavelength by a reaction with the labeling substance 307 or a catalyst action provided by the labeling substance 307. A specimen solution is introduced into the first portion 106q of the reaction chamber 106. The specimen may be injected into the first portion 106q of the reaction chamber 106 by use of a syringe or the like.

Figure 6:
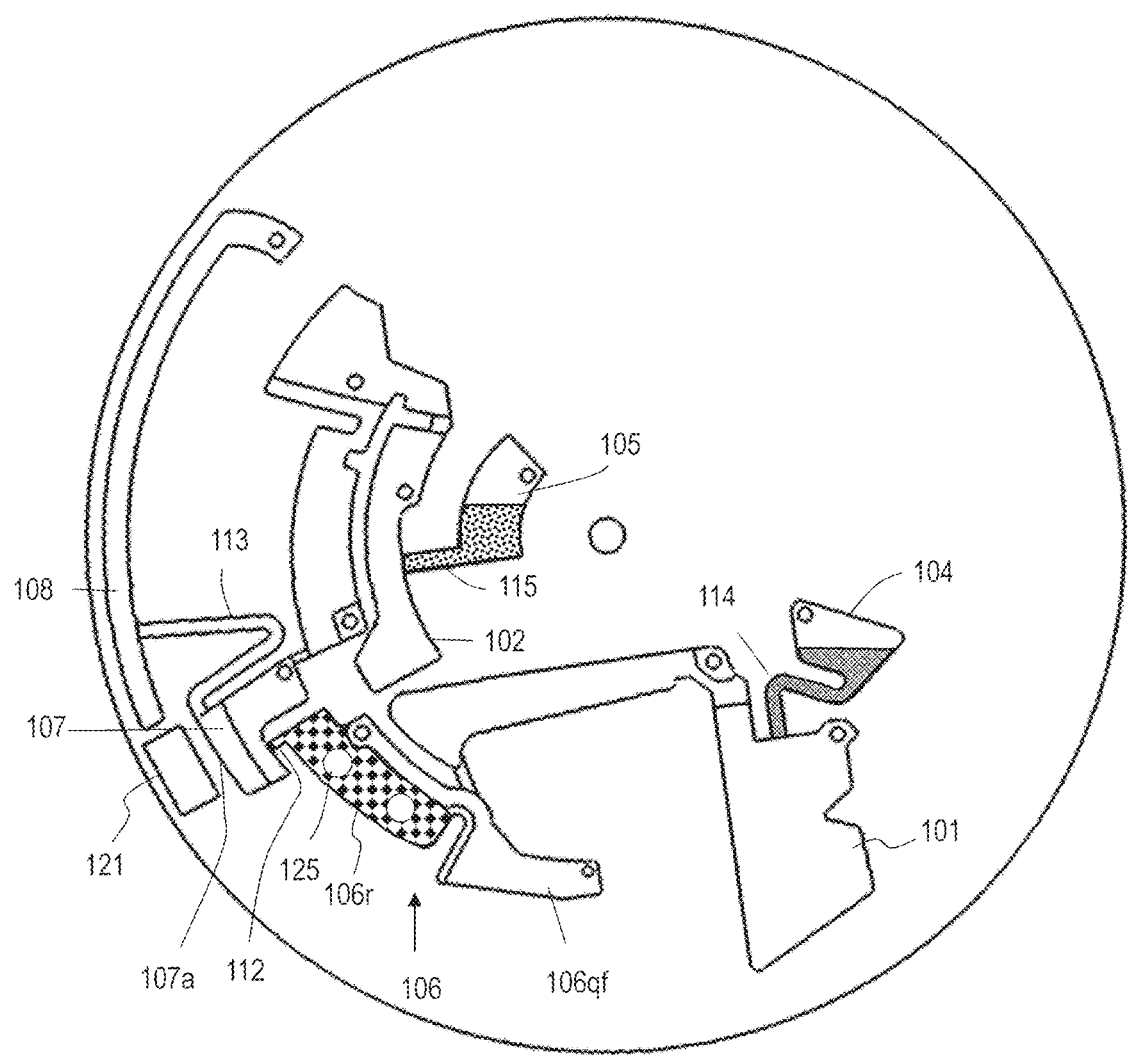
FIG. 6 schematically shows an example of angle at which the sample analysis substrate is stopped and an example of position of the liquid during the operation of the sample analysis system.

When being introduced into the first portion 106q of the reaction chamber 106, the specimen solution fills the first region 106qf, which is a non-capillary space, of the first portion 106q and the second region 106qe, which is a capillary space, of the first portion 106q. The second region 106qe is connected with the second region 106re, which is a capillary space, of the second portion 106r. Therefore, as shown in FIG. 6, the specimen solution is absorbed into these capillary spaces by a capillary force. As a result, the specimen solution located in the first region 106qf of the first portion 106g is moved to the second region 106re of the second portion 106r.

As a result, the specimen solution contacts the dried agent 125, and thus the magnetic particle-immobilized antibody 30 is released into the specimen solution and the labeled antibody 308 is eluted into the specimen solution. In the specimen solution, the magnetic particle-immobilized antibody 305, the antigen 306 in the specimen, and the labeled antibody 308 are bound to each other by an antigen-antibody reaction to generate the complex body 310. In order to promote the release of the magnetic particle-immobilized antibody 30 and the elution of the labeled antibody 308 into the specimen solution, the sample analysis substrate 100 may be swung. At this point, the fifth flow path 115, the fourth flow path 114 and the second flow path 112 are respectively filled with the substrate solution, the washing solution and the reaction solution containing the complex 310 by a capillary action.

[Step S12]

After the complex body 310 is generated, the sample analysis substrate 100 is rotated to move the reaction solution containing the complex body 310 to the main chamber 107 from the second region 106re of the second portion 106r of the reaction chamber 106. As described above, the second flow path 112 is filled with the reaction solution by the capillary action. Therefore, when the reaction solution containing the complex body 310 in the reaction chamber 106 is subjected to a centrifugal force stronger than the capillary force applied to the reaction solution in the second flow path 112 by the rotation of the sample analysis substrate 100, the reaction solution is transferred to the main chamber 107. The reaction solution transferred to the main chamber 107 is not transferred to the recovery chamber 108 as long as the sample analysis substrate 100 is rotating. A reason for this is that since the third flow path 113 has a siphon structure as described above, the liquid does not move in the third flow path 113 toward the rotation shaft 110 against the centrifugal force. In the reaction solution containing the complex body 310 transferred to the main chamber 107, most of the magnetic particles 311 are captured by the outermost side surface 107a by the magnetic force of the magnet 121.

The rotation rate of the sample analysis substrate 100 is set to a level at which the centrifugal force provided by the rotation prevents the liquid such as the reaction solution or the like from moving by a gravitational force and at which the liquid is subjected to a centrifugal force stronger than the capillary force of each of the capillary channels. In later steps, such a rotation rate is set for the rotation, a centrifugal force provided by which is to be used. In this embodiment, in the case where the sample analysis substrate 100 is rotated to provide such a centrifugal force, the sample analysis substrate 100 is rotated clockwise.

At the same time as the movement of the reaction solution, the washing solution is transferred from the first storage chamber 104 to the first holding chamber 101 via the fourth flow path 114. The substrate solution is transferred from the second storage chamber 105 to the second holding chamber 102 via the fifth flow path 115.

Figure 7:
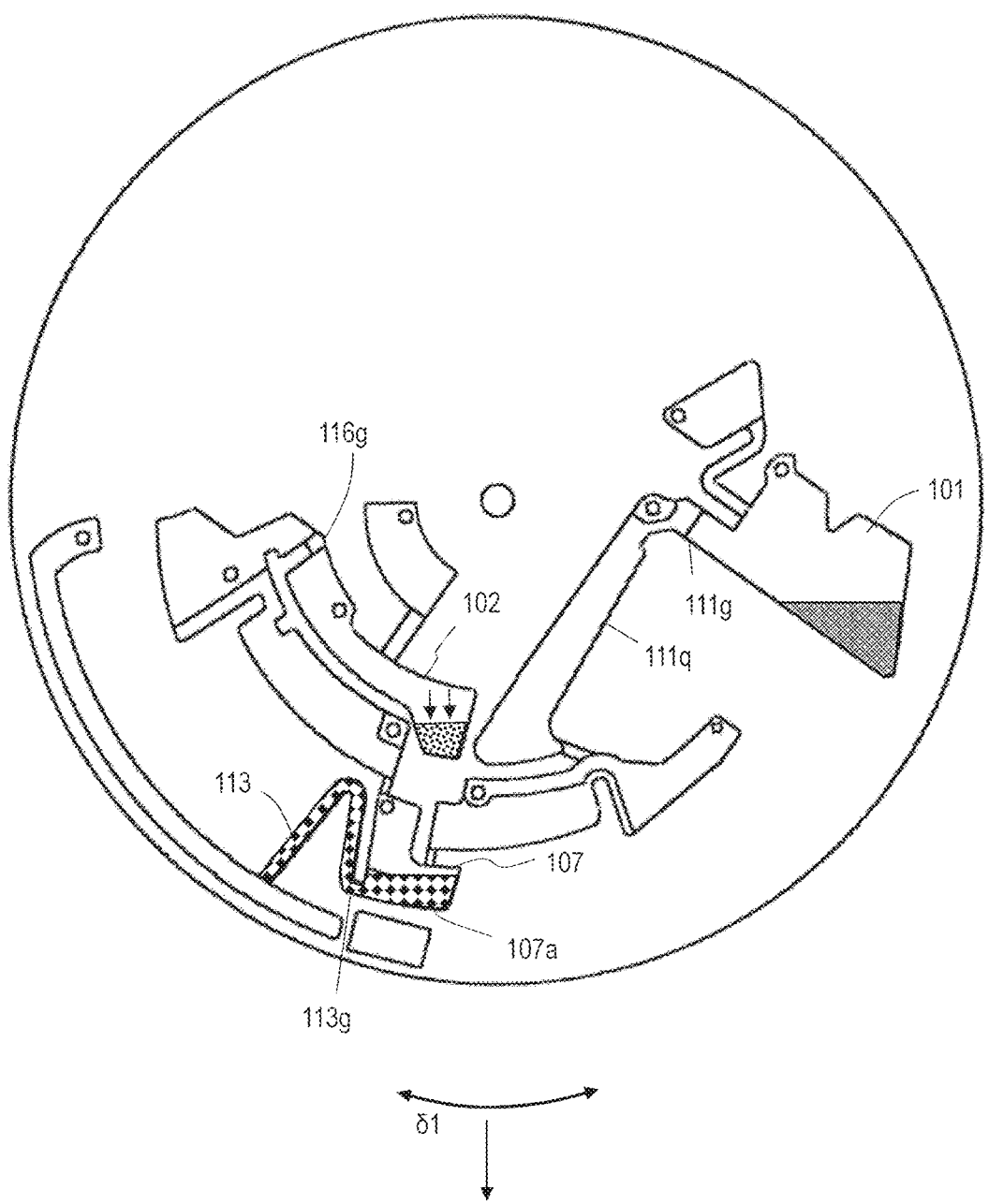
FIG. 7 schematically shows an example of angle at which the sample analysis substrate is stopped and an example of position of the liquid during the operation of the sample analysis system.

After the washing solution, the substrate solution and the reaction solution are all transferred respectively to the first holding chamber 101, the second holding chamber 102 and the main chamber 107, the sample analysis substrate 100 is stopped at a predetermined first angle. As shown in FIG. 7, the predetermined first angle is an angle at which, in the sample analysis substrate 100, the washing solution transferred to the first holding chamber 101 does not contact the first portion 111g beyond the opening 111g of the first flow path 111, the substrate solution in the second holding chamber 102 does not contact the opening 116g of the sixth flow path 116, and the reaction solution in the main chamber 107 contacts the opening 113g of the third flow path 113. This angle depends on the shapes and the positions in the substrate 100' of the second holding chamber 102, the main chamber 107 and the first holding chamber 101, the amounts of the washing solution, the substrate solution and the reaction solution, the inclination angle θ of the sample analysis substrate 100, and the like. In the example shown in FIG. 7, it is sufficient that the direction of gravity (represented by the arrow) in the sample analysis system 501 projected on a plane parallel to the sample analysis substrate 100 is in the angle range of the sample analysis substrate 100 represented by δ1.

The reaction solution in the main chamber 107 contacts the opening 113g of the third flow path 113 to fill the third flow path 113 by a capillary action.

[Step S13]

The sample analysis substrate 100 is rotated. Along with the rotation, a centrifugal force is generated and acts on the reaction solution and the magnetic particles 311 (complex body 310 and the unreacted magnetic particles) in the main chamber 107. This centrifugal force acts to cause the liquid and the complex body 310 to move toward the outermost side surface 107a of the main chamber 107. Therefore, the magnetic particles 311 are pressed onto the outermost side surface 107a.

Figure 8:
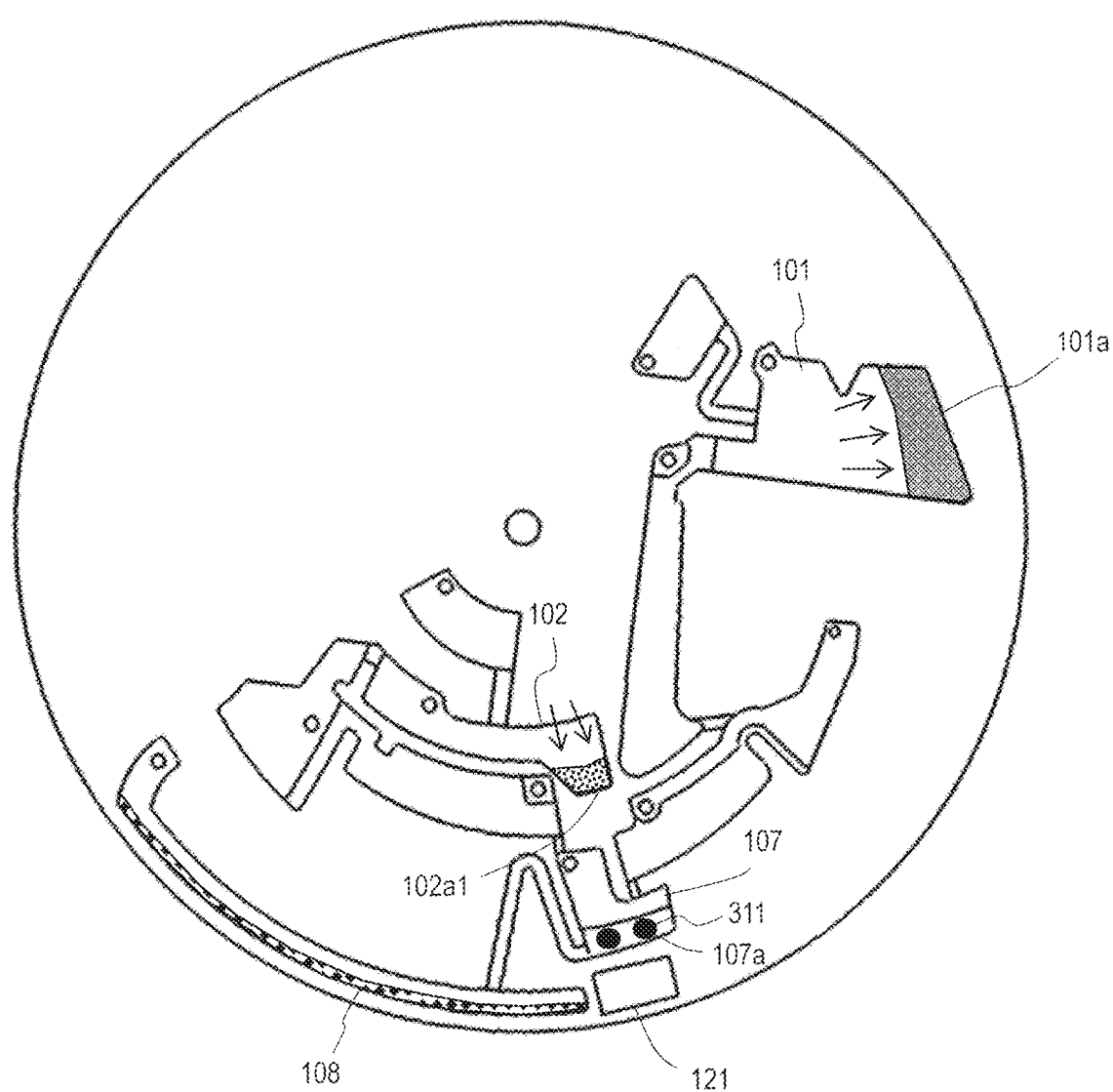
FIG. 8 schematically shows an example of angle at which the sample analysis substrate is stopped and an example of position of the liquid during the operation of the sample analysis system.

As shown in FIG. 8, the reaction solution receiving the centrifugal force is discharged from the third flow path 113 and transferred to the recovery chamber 108. The magnetic particles 311 are strongly pressed onto the outermost side surface 107a by the sum of the centrifugal force and the absorbing force of the magnet 121 and are captured.

As a result, only the reaction solution is discharged from the third flow path 113 to the recovery chamber 108, whereas the magnetic particles 311 stay in the main chamber 107. The washing solution in the first holding chamber 101 receives the centrifugal force by the rotation but is pressed onto the outermost side surface 101a of the first holding chamber 101 and thus stays in the first holding chamber 101. The substrate solution in the second holding chamber 102 also receives the centrifugal force by the rotation but is pressed onto the first outer side surface 102a1 and thus stays in the second holding chamber 102.

After the transfer of the reaction solution to the recovery chamber 108 and the transfer of the substrate solution to the main chamber 107 are finished, the rotation of the sample analysis substrate 100 is stopped.

In this manner, the reaction solution and the magnetic particles 311 are separated from each other. Specifically, the reaction solution moves to the recovery chamber 108, whereas the magnetic particles 311 stay in the main chamber 107. Even after the rotation of the sample analysis substrate 100 is stopped, the magnetic particles 311 may be kept in the state of gathering at the outermost side surface 107a by the absorbing force received from the magnet 121. The angle at which the sample analysis substrate 100 is stopped may be the first angle, a second angle described regarding the next step or any other angle.

[Step S14]

Figure 9:
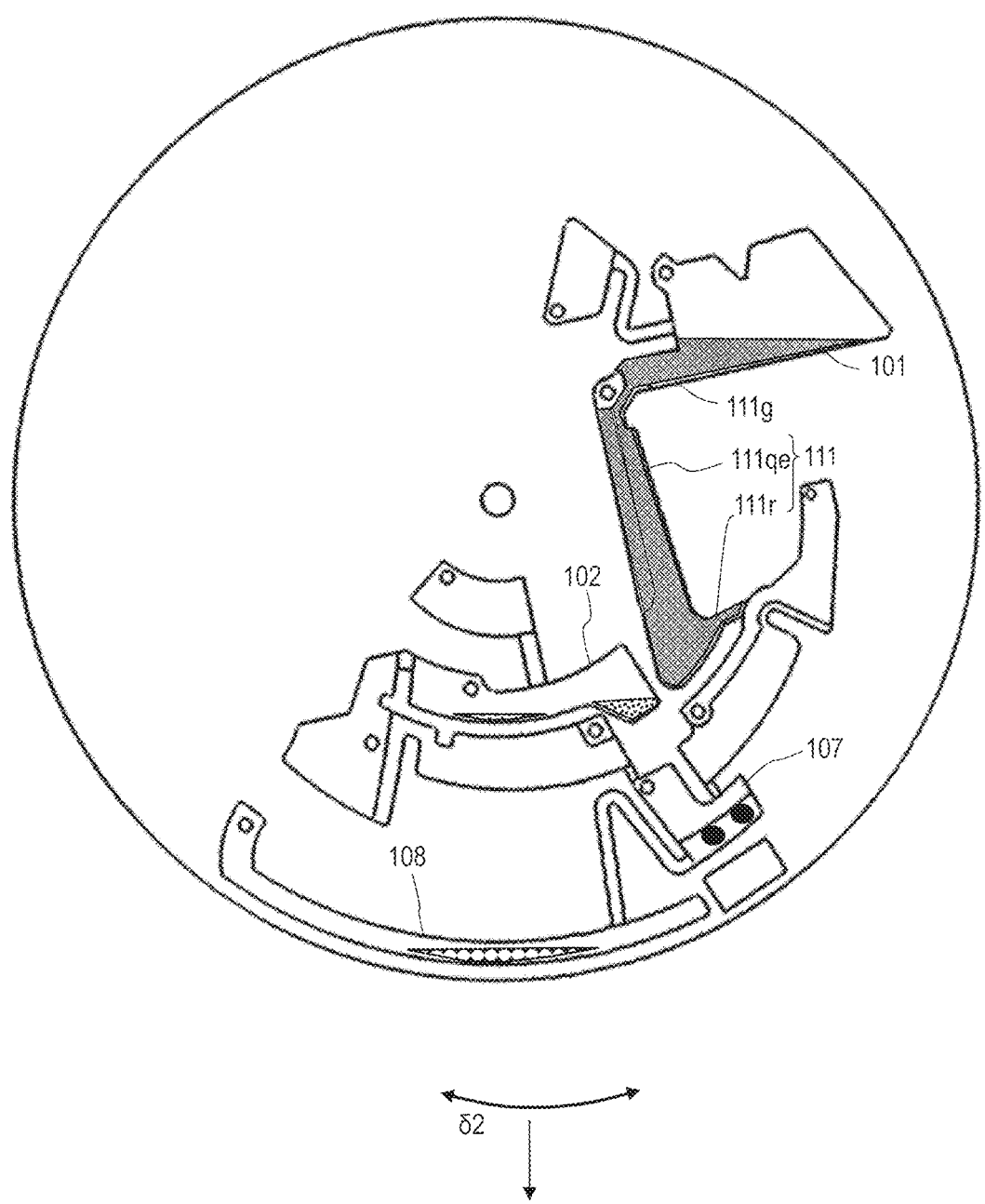
FIG. 9 schematically shows an example of angle at which the sample analysis substrate is stopped and an example of position of the liquid during the operation of the sample analysis system.

As shown in FIG. 9, in the case of not being stopped at the second angle in the previous step, the sample analysis substrate 100 is slightly rotated and stopped at the second angle, which is predetermined. The second angle is an angle at which the washing solution transferred to the first holding chamber 101 contacts the opening 111g of the first flow path 111. For example, in the example shown in FIG. 9, the second angle is an angle at which the direction of gravity is located in the angle range of the sample analysis substrate 100 represented by δ2.

The washing solution, when contacting the first portion 111g of the first flow path 111 via the opening 111g, is absorbed into the entirety of the first region 111qe of the first portion 111g by a capillary force, and the first portion 111q and the second portion 111r of the first flow path 111 are filled with the washing solution. The second region 111qf is also filled with the washing solution moved by a gravitational force. Thus, the amount of washing solution needed for one cycle of washing is weighed out.

In order to guarantee that the first flow path 111 is filled with the washing solution, the sample analysis substrate 100 may be rotated several times clockwise and counterclockwise alternately, namely, may be swung, around the second angle. At this point, the washing solution does not move from the second portion 111r of the first flow path 111 to the main chamber 107 because the capillary force acts on the first flow path 111.

[Step S15]

Figure 10:
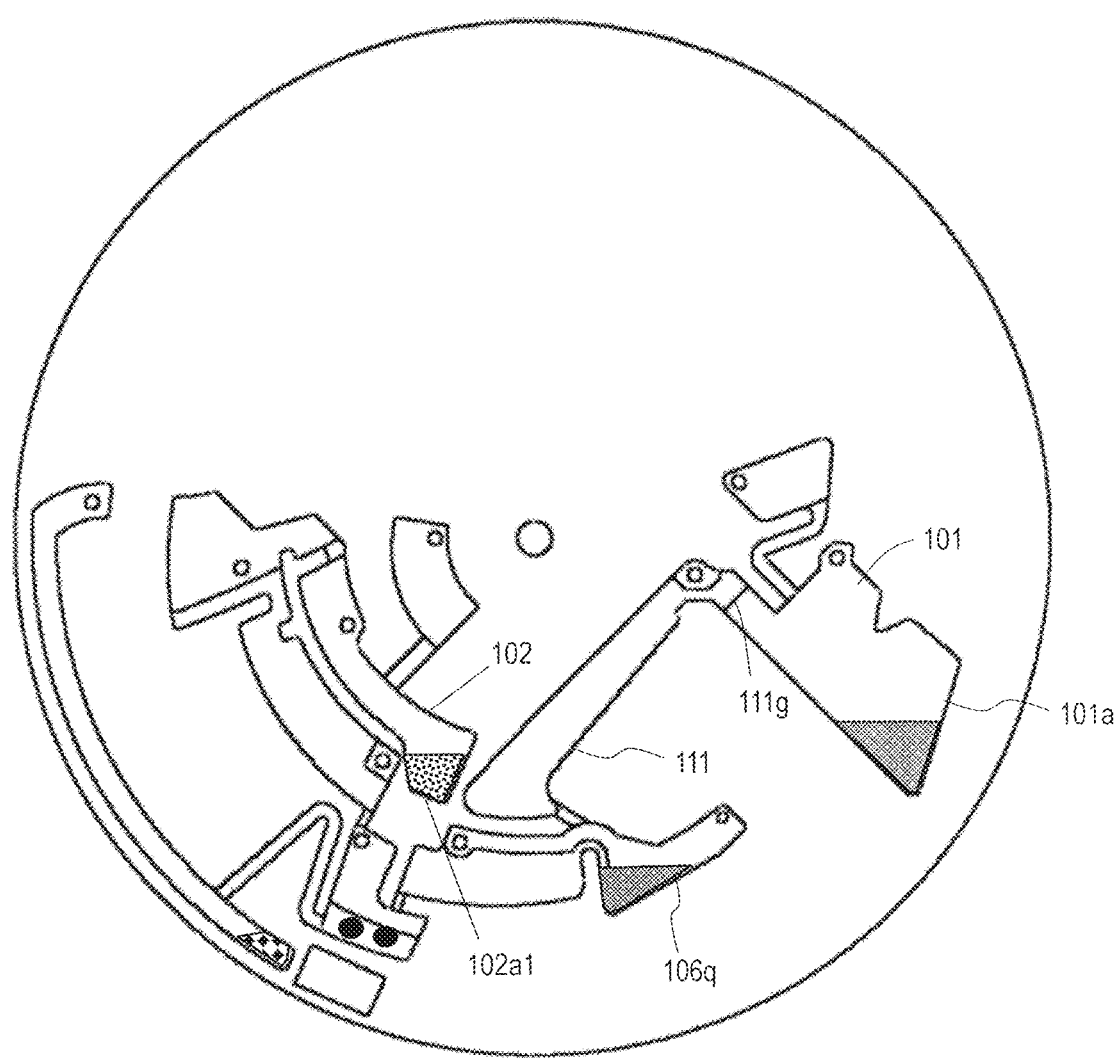
FIG. 10 schematically shows an example of angle at which the sample analysis substrate is stopped and an example of position of the liquid during the operation of the sample analysis system.

Next, the sample analysis substrate 100 is rotated. A centrifugal force provided by the rotation acts on the washing solution in the first flow path 111 and the first holding chamber 101. As described above with reference to FIG. 3G, the washing solution that is located on the side of the first flow path 111 with respect to the straight line db moves to the first portion 106q of the reaction chamber 106 via the first flow path 111. The washing solution that is located on the side of the first holding chamber 101 with respect to the straight line db is returned to the first holding chamber 101 by the centrifugal force. Therefore, as shown in FIG. 10, only the washing solution weighed out by use of the first flow path 111 is transferred to the first portion 106q of the reaction chamber 106.

In the second holding chamber 102, the substrate solution is pressed onto the first outer side surface 102a1 by the centrifugal force. Therefore, the substrate solution stays in the second holding chamber 102. Similarly, the washing solution in the first holding chamber 101 is also pressed onto the outermost side surface 101a by the centrifugal force. Therefore, the washing solution stays in the first holding chamber 101.

Figure 11:
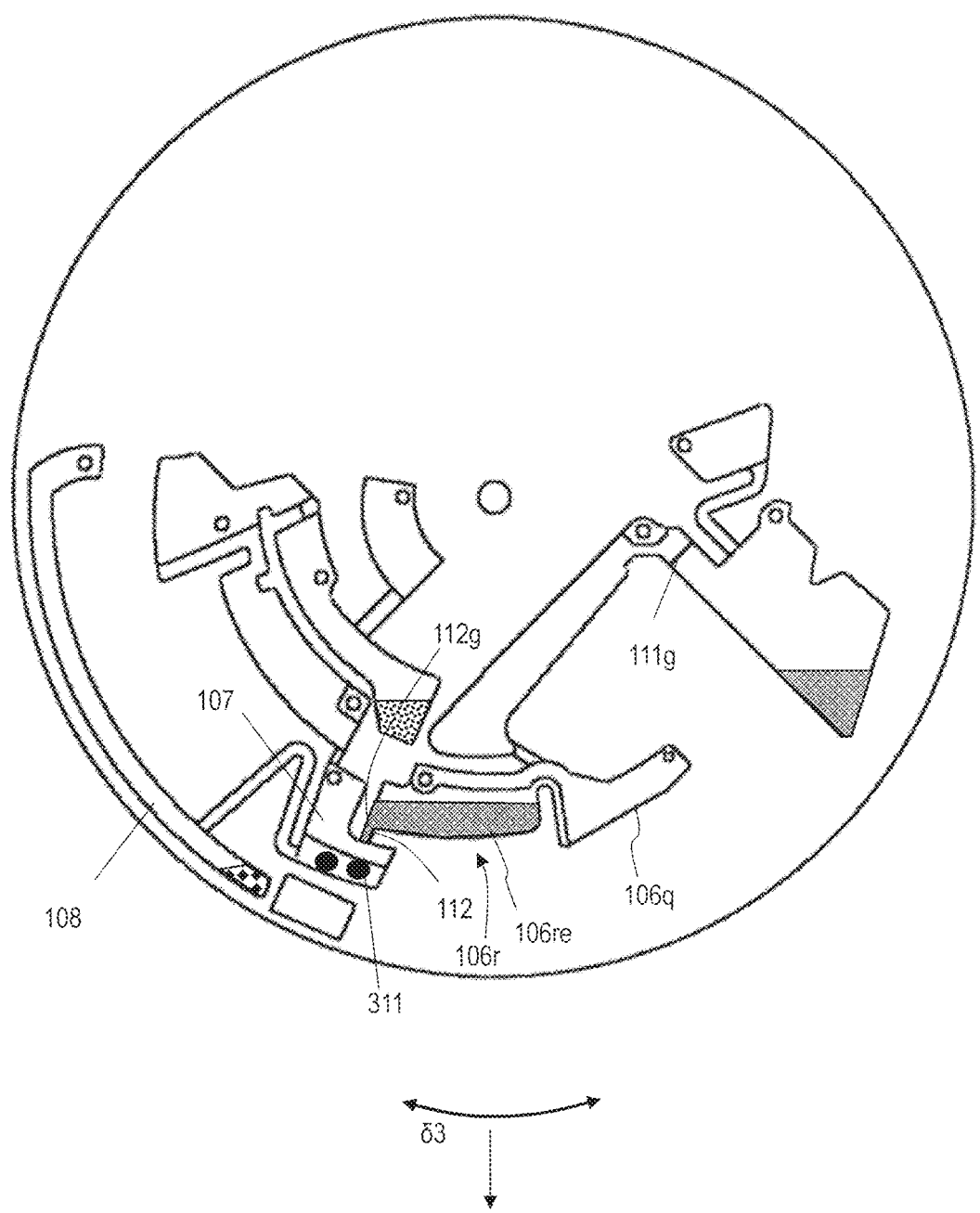
FIG. 11 schematically shows an example of angle at which the sample analysis substrate is stopped and an example of position of the liquid during the operation of the sample analysis system.

As shown in FIG. 11, after all the washing solution in the first flow path 111 moves to the first portion 106q of the reaction chamber 106, the sample analysis substrate 100 is stopped at a predetermined third angle. The third angle is an angle at which the washing solution in the first holding chamber 101 does not contact the opening 111g. For example, in the example shown in FIG. 11, it is sufficient that the direction of gravity in the sample analysis system 501 projected on a plane parallel to the sample analysis substrate 100 is in the angle range of the sample analysis substrate 100 represented by δ3.

When the washing solution that has been weighed out is introduced into the first portion 106q of the reaction chamber 106, the washing solution fills the first region 106qf, which is a non-capillary space, of the first portion 106q and the second region 106qe, which is a capillary space, of the first portion 106q. The second region 106qe is connected with the second region 106re, which is a capillary space, of the second portion 106r. Therefore, the washing solution is absorbed into these capillary spaces by a capillary force. As a result, the washing solution located in the first region 106qf of the first portion 106q moves to the second region 106re of the second portion 106r. Therefore, the reaction solution remaining in the first portion 106q and the second portion 106r of the reaction chamber 106 is mixed with the washing solution. Namely, the reaction chamber 106 is washed with the washing solution.

The washing solution in the reaction chamber 106 contacts the opening 112g of the second flow path 112 to fill the second flow path 112 by a capillary action.

[Step S16]

The sample analysis substrate 100 is rotated to move the washing solution from the second region 106re of the second portion 106r of the reaction chamber 106 to the main chamber 107. The second flow path 112 is filled with the washing solution. Therefore, when the washing solution in the second flow path 112 is subjected to a centrifugal force, provided by the rotation of the sample analysis substrate 100, that is stronger than the capillary force, the washing solution is transferred to the main chamber 107. As a result, the reaction solution remaining in the first portion 106q and the second portion 106r of the reaction chamber 106 is transferred to the main chamber 107 together with the washing solution. The magnetic particles 311 in the main chamber 107 contact the washing solution to perform a first cycle of washing.

The reaction solution transferred to the main chamber 107 is not transferred to the recovery chamber 108 as long as the sample analysis substrate 100 is rotating. A reason for this is that since the third flow path 113 has a siphon structure, the washing solution does not move in the third flow path 113 toward the rotation shaft 110 against the centrifugal force. The washing solution in the first holding chamber 101 and the substrate solution in the second holding chamber 102 stay in the respective chambers.

Figure 12:
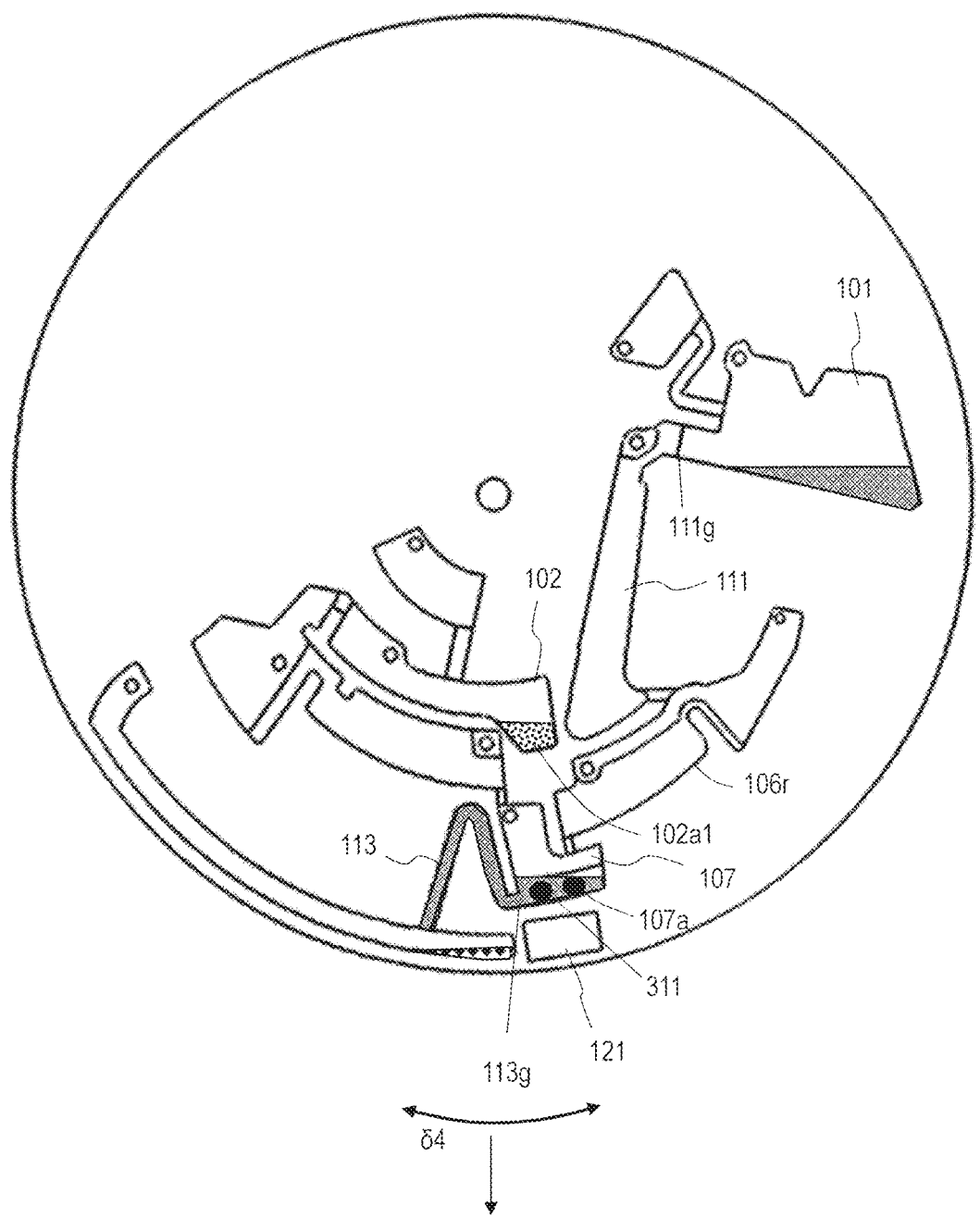
FIG. 12 schematically shows an example of angle at which the sample analysis substrate is stopped and an example of position of the liquid during the operation of the sample analysis system.

As shown in FIG. 12, after the washing solution in the reaction chamber 106 is all moved to the main chamber 107, the sample analysis substrate 100 is stopped at a predetermined fourth angle. The fourth angle is an angle at which the washing solution in the first holding chamber 101 does not contact the opening 111g and the washing solution transferred to the main chamber 107 contacts the opening 113g of the third flow path 113. For example, in the example shown in FIG. 12, it is sufficient that the direction of gravity in the sample analysis system 501 projected on a plane parallel to the sample analysis substrate 100 is in the angle range of the sample analysis substrate 100 represented by δ4.

The washing solution in the main chamber 107 contacts the opening 113g of the third flow path 113 to fill the third flow path 113 by a capillary action.

[Step S17]

The sample analysis substrate 100 is rotated. Along with the rotation, a centrifugal force is generated and acts on the washing solution and the magnetic particles 311 in the main chamber 107. This centrifugal force acts to cause the washing solution and the magnetic particles 311 to move toward the outermost side surface 107a of the main chamber 107. The washing solution and the magnetic particles 311 are captured at the outermost side surface 107a by the centrifugal force and the absorbing force of the magnet 121.

Figure 13:
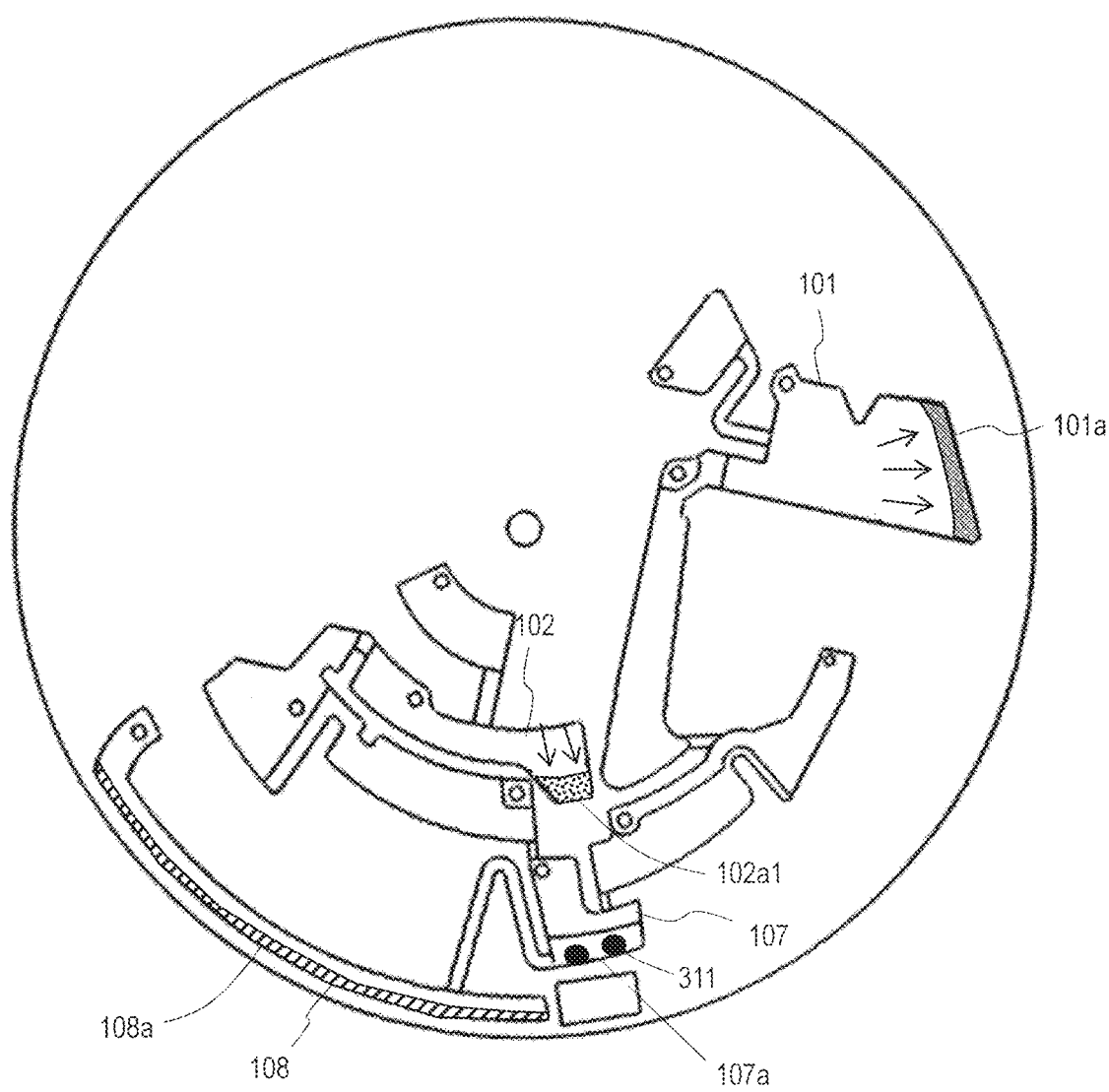
FIG. 13 schematically shows an example of angle at which the sample analysis substrate is stopped and an example of position of the liquid during the operation of the sample analysis system.

As shown in FIG. 13, the washing solution receiving the centrifugal force is discharged from the third flow path 113 and transferred to the recovery chamber 108. In this manner, only the washing is discharged from the third flow path 113, whereas the magnetic particles 311 stay in the main chamber 107. The washing solution in the first holding chamber 101 and the substrate solution in the second holding chamber 102 are respectively pressed onto the outermost side surface 101a and the first outer side surface 102a1 and thus stay in the first holding chamber 101 and the second holding chamber 102.

After the transfer of the washing solution to the recovery chamber 108 is finished, the rotation of the sample analysis substrate 100 is stopped. As a result, the washing solution and the magnetic particles 311 are separated from each other. Specifically, the washing solution moves to the recovery chamber 108, whereas the magnetic particles 311 stay in the main chamber 107. Even after the rotation of the sample analysis substrate 100 is stopped, the magnetic particles 311 may be kept in the state of gathering at the outermost side surface 107a by the absorbing force received from the magnet 121. The angle at which the sample analysis substrate 100 is stopped may be the fourth angle or a fifth angle described regarding the next step.

[Step S18]

Figure 14:
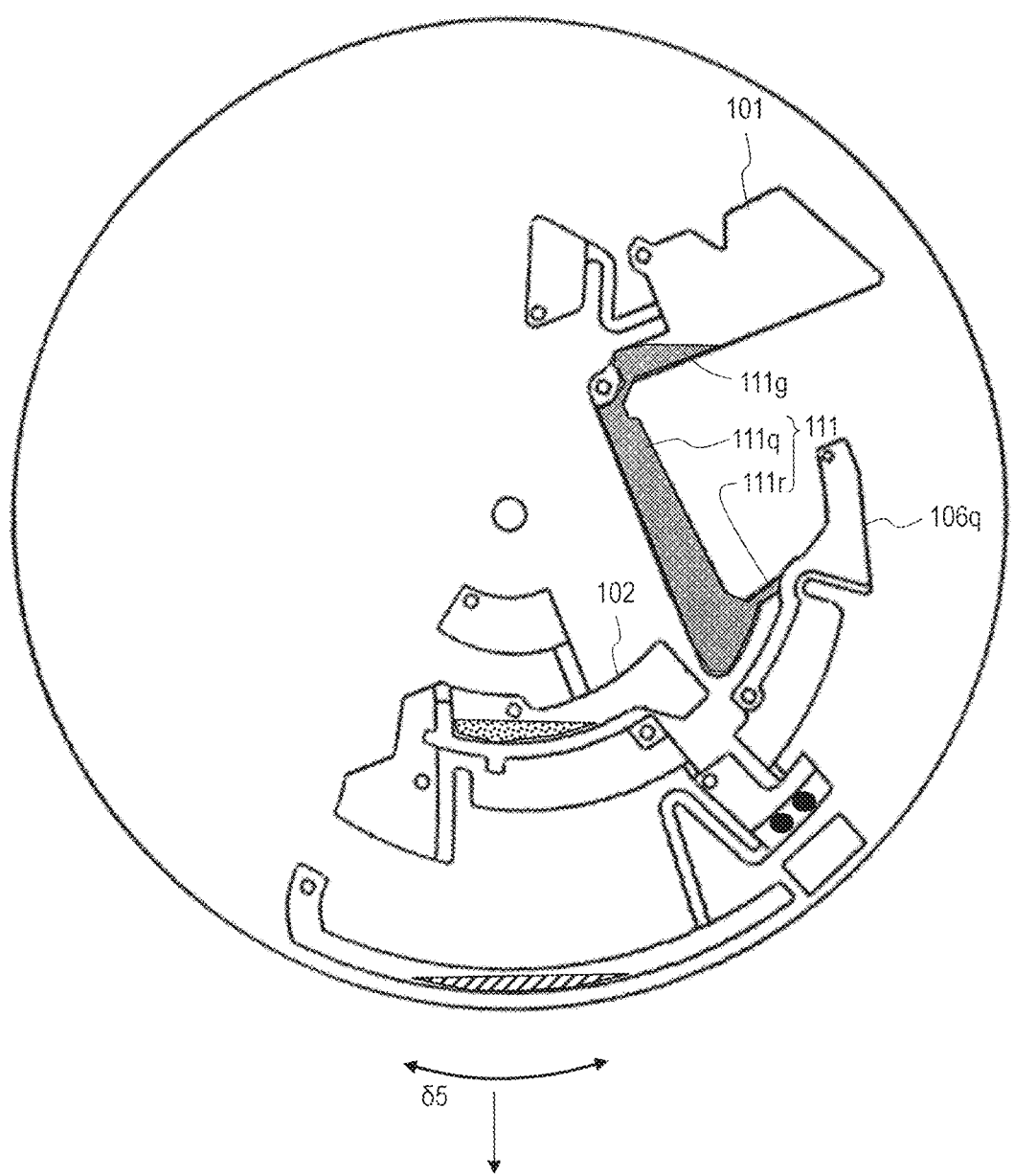
FIG. 14 schematically shows an example of angle at which the sample analysis substrate is stopped and an example of position of the liquid during the operation of the sample analysis system.

As shown in FIG. 14, in the case of not being stopped at the fifth angle in the previous step, the sample analysis substrate 100 is slightly rotated and stopped at the fifth angle, which is predetermined. The fifth angle is an angle at which the washing solution transferred to the first holding chamber 101 contacts the opening 111q of the first flow path 111. For example, in the example shown in FIG. 14, the fifth angle is an angle at which the direction of gravity is located in the angle range of the sample analysis substrate 100 represented by δ5. Since the amount of washing solution left in the first holding chamber 101 is different from that in step S4, the angle range δ4 may be different from the angle range δ2.

The washing solution is absorbed into the first flow path 111 from the first holding chamber 101 by a capillary force of the first portion 111q of the first flow path 111, and the first portion 111q and the second portion 111r of the first flow path 111 are filled with the washing solution. Thus, the amount of washing solution needed for one cycle of washing is weighed out again.

In order to guarantee that the first flow path 111 is filled with the washing solution, the sample analysis substrate 100 may be swung around the fifth angle. At this point, the washing solution does not move from the first flow path 111 to the reaction chamber 106 because a capillary force acts on the first flow path 111.

[Step S19]

Figure 15:
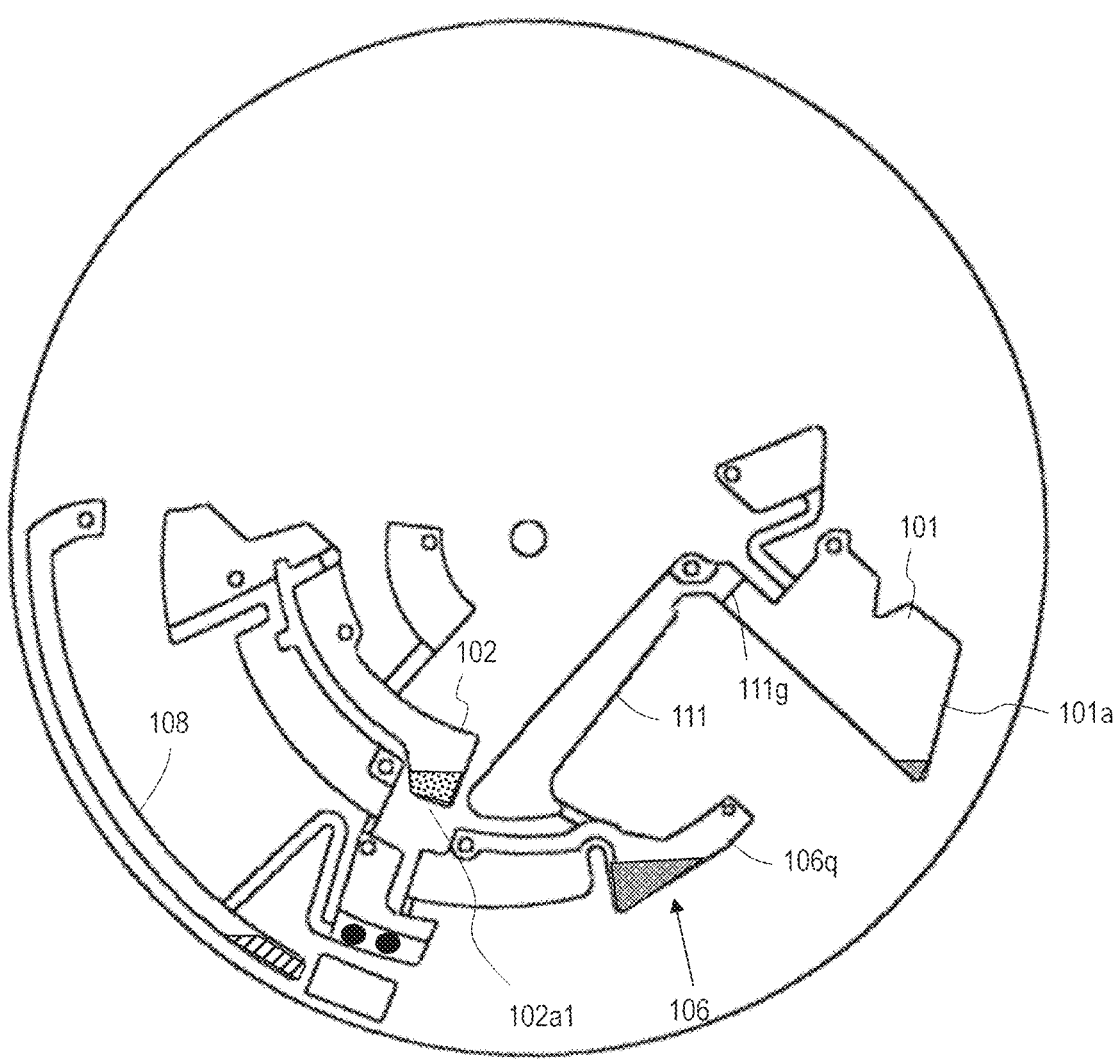
FIG. 15 schematically shows an example of angle at which the sample analysis substrate is stopped and an example of position of the liquid during the operation of the sample analysis system.

Next, the sample analysis substrate 100 is rotated. A centrifugal force provided by the rotation acts on the washing solution in the first flow path 111 and the first holding chamber 101. Like in the first cycle of washing, the washing solution that is located on the side of the first flow path 111 with respect to the straight line db in FIG. 3G moves to the first portion 106q of the reaction chamber 106 via the first flow path 111. The washing solution that is located on the side of the first holding chamber 101 with respect to the straight line db is returned to the first holding chamber 101 by the centrifugal force. Therefore, as shown in FIG. 15, only the washing solution weighed out by use of the first flow path 111 is transferred to the first portion 106q of the reaction chamber 106.

The substrate solution is pressed onto the first outer side surface 102a1 of the second holding chamber 102 by the centrifugal force. Therefore, the substrate solution stays in the second holding chamber 102. Similarly, the washing solution in the first holding chamber 101 is pressed onto the outermost side surface 101a in the first holding chamber 101 by the centrifugal force. Therefore, the washing solution stays in the first holding chamber 101.

Figure 16:
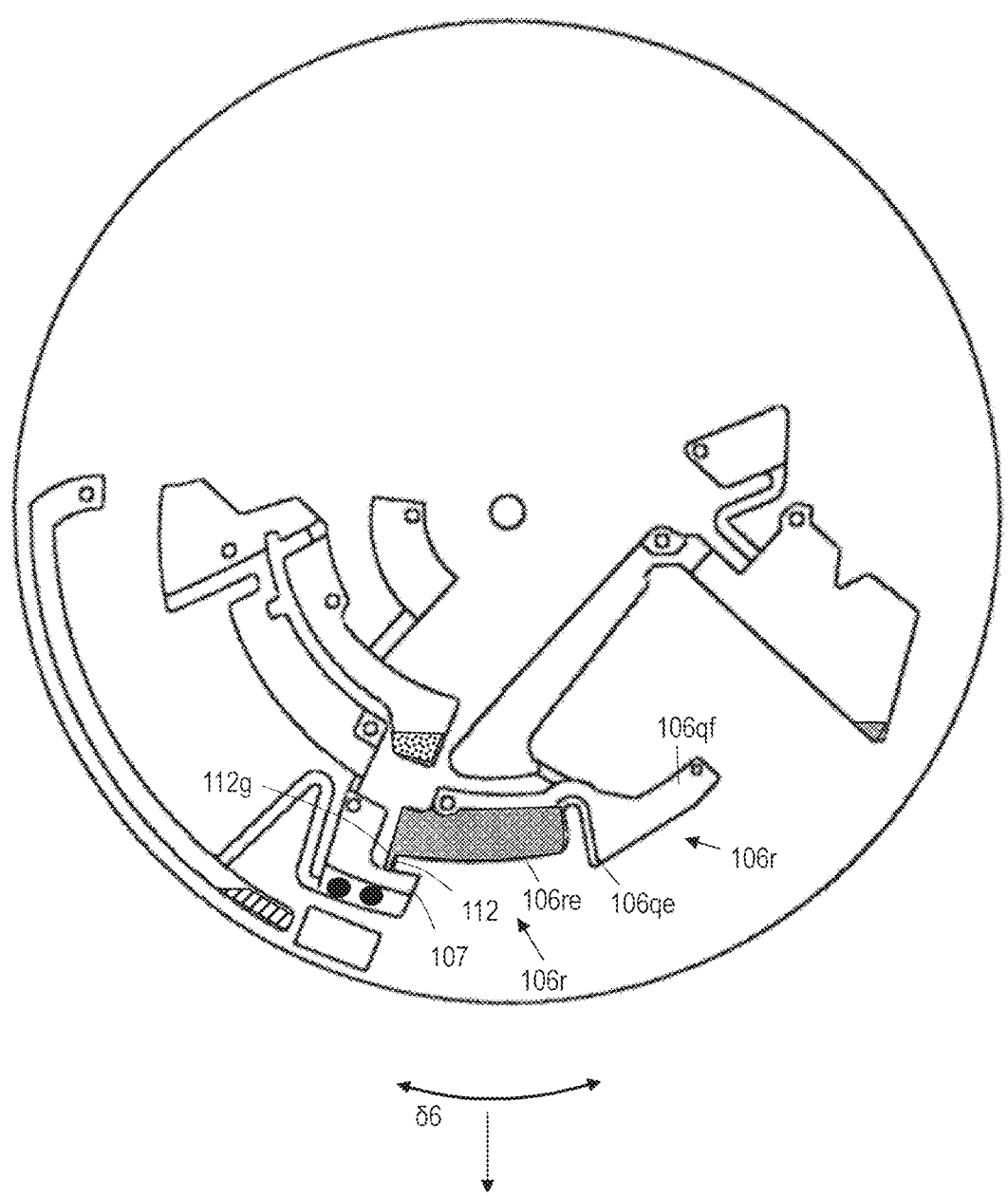
FIG. 16 schematically shows an example of angle at which the sample analysis substrate is stopped and an example of position of the liquid during the operation of the sample analysis system.

As shown in FIG. 16, after the washing solution in the first flow path 111 is all transferred to the first portion 106q of the reaction chamber 106, the rotation of the sample analysis substrate 100 is stopped at a predetermined sixth angle. The sixth angle is an angle at which the washing solution in the first holding chamber 101 does not contact the opening 111g. For example, in the example shown in FIG. 16, it is sufficient that the direction of gravity in the sample analysis system 501 projected on a plane parallel to the sample analysis substrate 100 is in the angle range of the sample analysis substrate 100 represented by δ6.

Like in the first cycle of washing, when the washing solution that has been weighed out is introduced into the first portion 106q of the reaction chamber 106, the washing solution fills the first region 106qf, which is a non-capillary space, of the first portion 106q and the second region 106qe, which is a capillary space, of the first portion 106q. The second region 106qe is connected with the second region 106re, which is a capillary space, of the second portion 106r. Therefore, the washing solution is absorbed into these capillary spaces by a capillary force. As a result, the washing solution located in the first region 106qf of the first portion 106q moves to the second region 106re of the second portion 106r. Therefore, the reaction solution that may possibly be remaining in the first portion 106q and the second portion 106r of the reaction chamber 106 is mixed with the washing solution. Namely, the reaction chamber 106 is washed again with the washing solution.

The washing solution in the reaction chamber 106 contacts the opening 112g of the second flow path 112 to fill the second flow path 112 by a capillary action.

[Step S20]

Like in the first cycle of washing, the sample analysis substrate 100 is rotated to move the washing solution from the second region 106re of the second portion 106r of the reaction chamber 106 to the main chamber 107. The second flow path 112 is filled with the washing solution. Therefore, when the washing solution in the second flow path 112 is subjected to a centrifugal force, provided by the sample analysis substrate 100, that is stronger than the capillary force, the washing solution is transferred to the main chamber 107. As a result, the reaction solution that may possibly be remaining in the first portion 106q and the second portion 106r of the reaction chamber 106 is transferred to the main chamber 107 together with the washing solution. In addition, the magnetic particles 311 in the main chamber 107 contact the washing solution to perform a second cycle of washing.

The reaction solution transferred to the main chamber 107 is not transferred to the recovery chamber 108 as long as the sample analysis substrate 100 is rotating, as described above. The washing solution in the first holding chamber 101 and the substrate solution in the second holding chamber 102 stay in the respective chambers.

Figure 17:
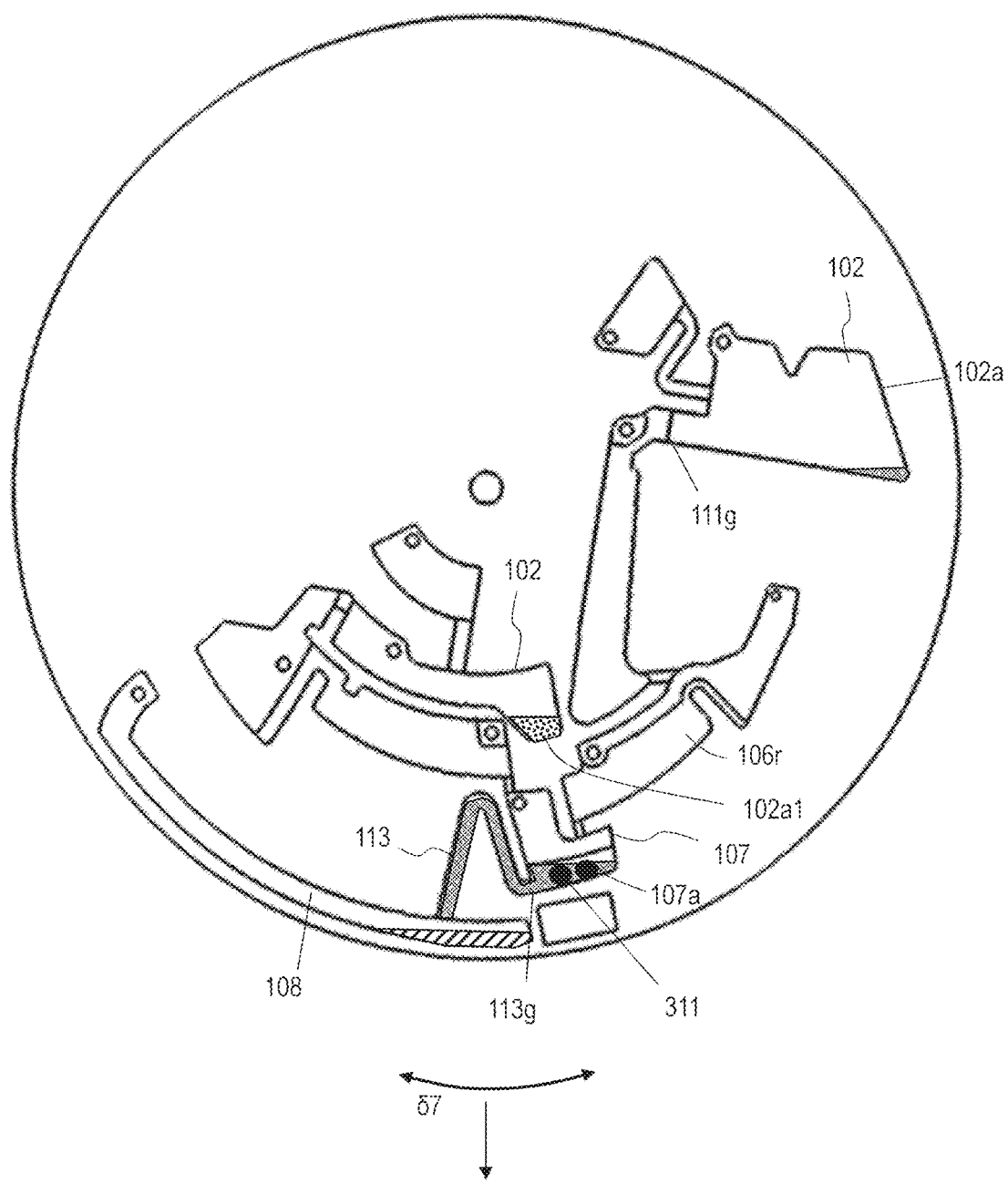
FIG. 17 schematically shows an example of angle at which the sample analysis substrate is stopped and an example of position of the liquid during the operation of the sample analysis system.

As shown in FIG. 17, after all the washing solution in the reaction chamber 106 moves to the main chamber 107, the sample analysis substrate 100 is stopped at a predetermined seventh angle. The seventh angle is an angle at which the washing solution in the first holding chamber 101 does not contact the opening 111g and the washing solution transferred to the main chamber 107 contacts the opening 113g of the third flow path 113. For example, in the example shown in FIG. 17, it is sufficient that the direction of gravity in the sample analysis system 501 projected on a plane parallel to the sample analysis substrate 100 is in the angle range of the sample analysis substrate 100 represented by δ7.

The washing solution in the main chamber 107 contacts the opening 113g of the third flow path 113 to fill the third flow path 113 by a capillary action.

[Step S21]

The sample analysis substrate 100 is rotated. Along with the rotation, a centrifugal force is generated and acts on the washing solution and the magnetic particles 311 in the main chamber 107. This centrifugal force acts to cause the washing solution and the magnetic particles 311 to move toward the outermost side surface 107a of the main chamber 107. The magnetic particles 311 are captured at the outermost side surface 107a by the centrifugal force and the absorbing force of the magnet 121.

The washing solution receiving the centrifugal force is discharged from the third flow path 113 and transferred to the recovery chamber 108. In this manner, only the washing solution is discharged from the third flow path 113, whereas the magnetic particles 311 stay in the main chamber 107. The washing solution in the first holding chamber 101 is pressed onto the outermost side surface 103a and thus stays in the first holding chamber 101. The substrate solution is also pressed onto the first outer side surface 102a1 and thus stays in the second holding chamber 102.

Figure 18:
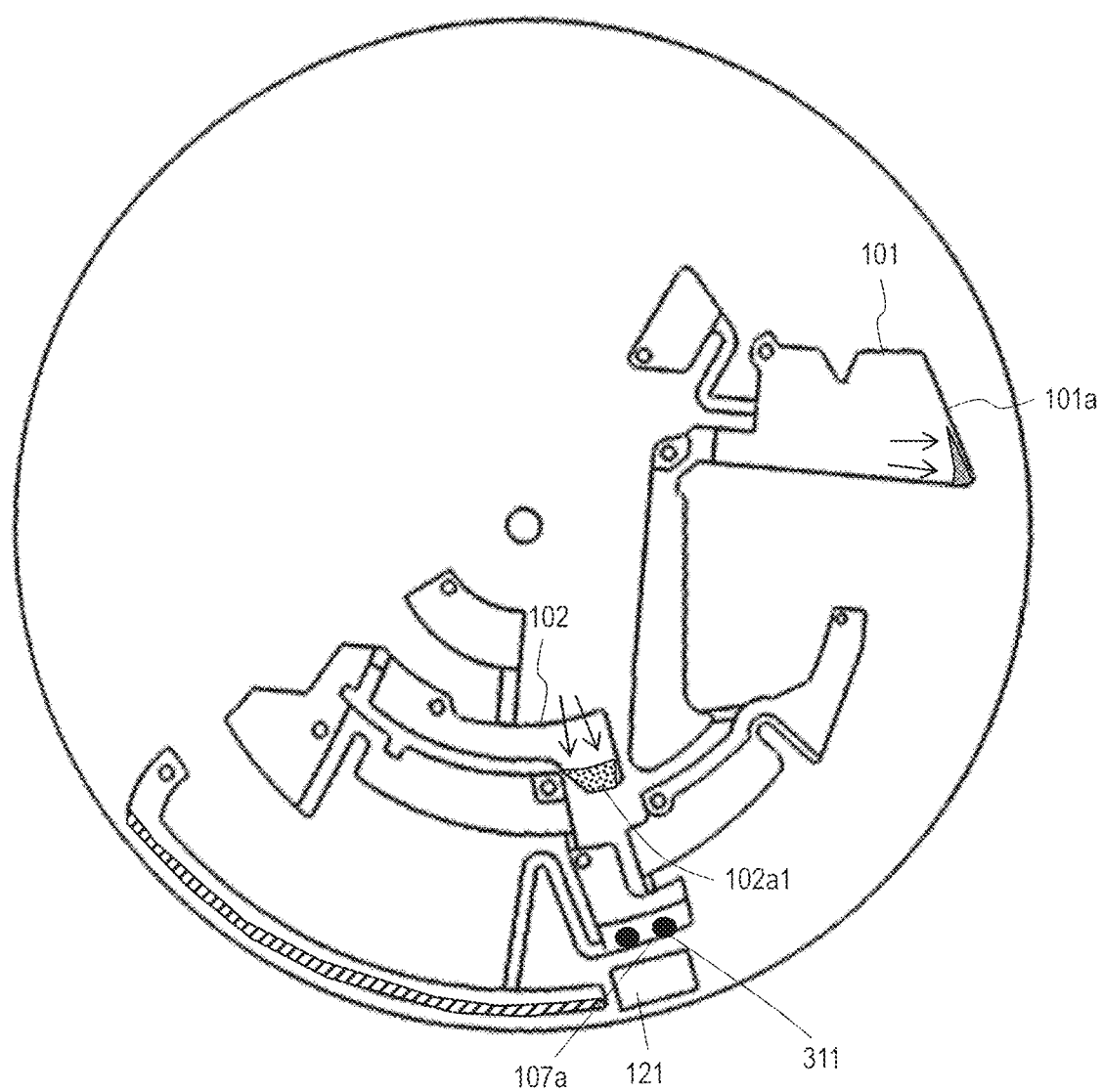
FIG. 18 schematically shows an example of angle at which the sample analysis substrate is stopped and an example of position of the liquid during the operation of the sample analysis system.

After the transfer of the washing solution to the recovery chamber 108 is finished, the rotation of the sample analysis substrate 100 is stopped. As a result, as shown in FIG. 18, the washing solution and the magnetic particles 311 are separated from each other. Specifically, the washing solution moves to the recovery chamber 108, whereas the magnetic particles 311 stay in the main chamber 107. Even after the rotation of the sample analysis substrate 100 is stopped, the magnetic particles 311 may be kept in the state of gathering at the outermost side surface 107a by the absorbing force received from the magnet 121. The angle at which the sample analysis substrate 100 is stopped may be the seventh angle or an eighth angle described regarding the next step. A B/F separation and washing step as described above is thus finished.

[Step S22]

The substrate solution is first moved from the second holding chamber 102 to the third holding chamber 103. As shown in FIG. 19, in the case of not being stopped at the eighth angle in the previous step, the sample analysis substrate 100 is rotated and stopped at the eighth angle, which is predetermined. In this case, the sample analysis substrate 100 is rotated clockwise. The eighth angle is an angle at which the substrate solution in the second holding chamber 102 contacts the opening 116g of the sixth flow path 116 and all the substrate solution may move to the third holding chamber 103 by a gravitational force. The eighth angle is an angle at which the sixth flow path 116 is located generally in the direction of gravity. As a result, the substrate solution in the second holding chamber 102 is transferred to the third holding chamber 103.

Figure 20:
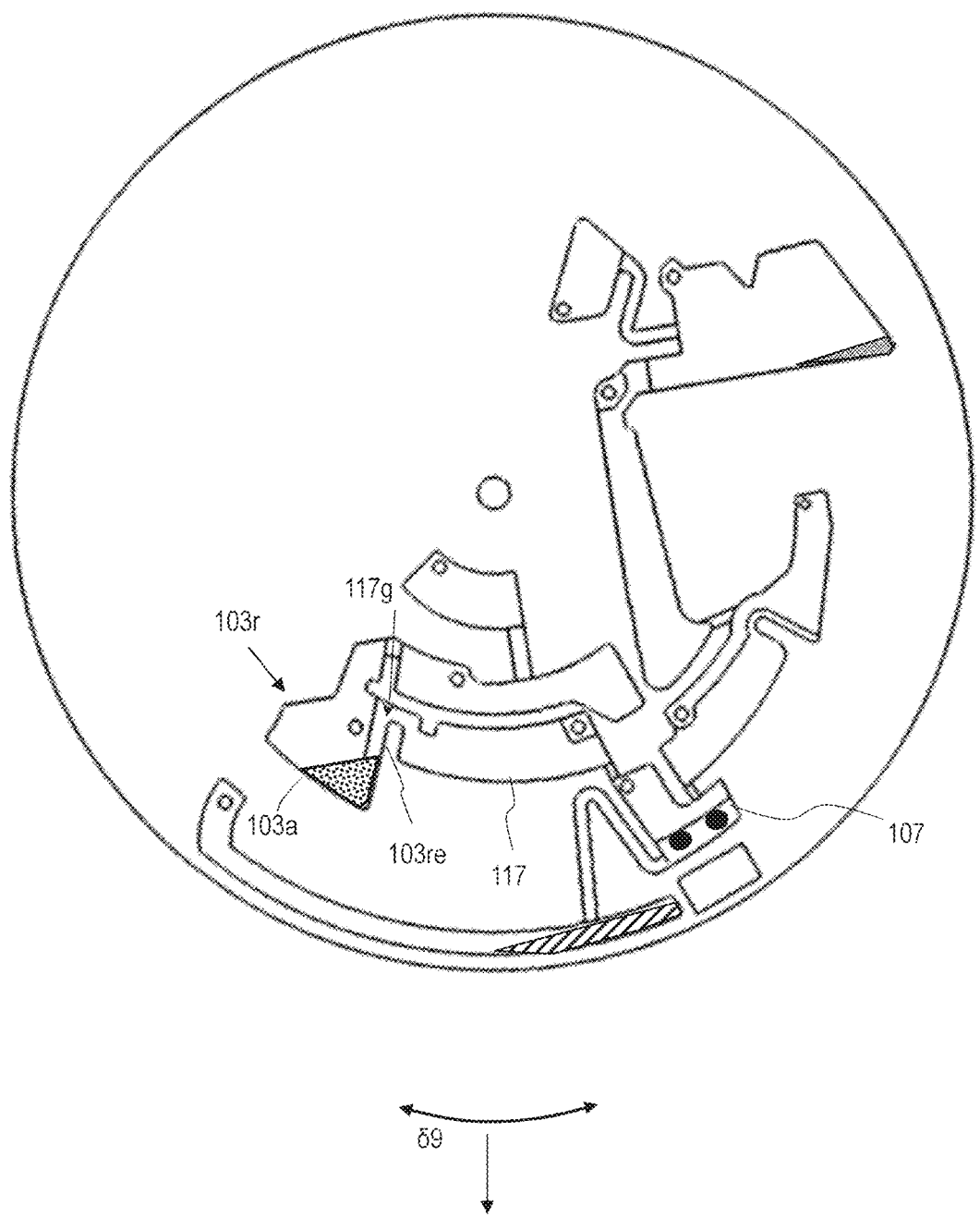
FIG. 20 schematically shows an example of angle at which the sample analysis substrate is stopped and an example of position of the liquid during the operation of the sample analysis system.
Figure 21:
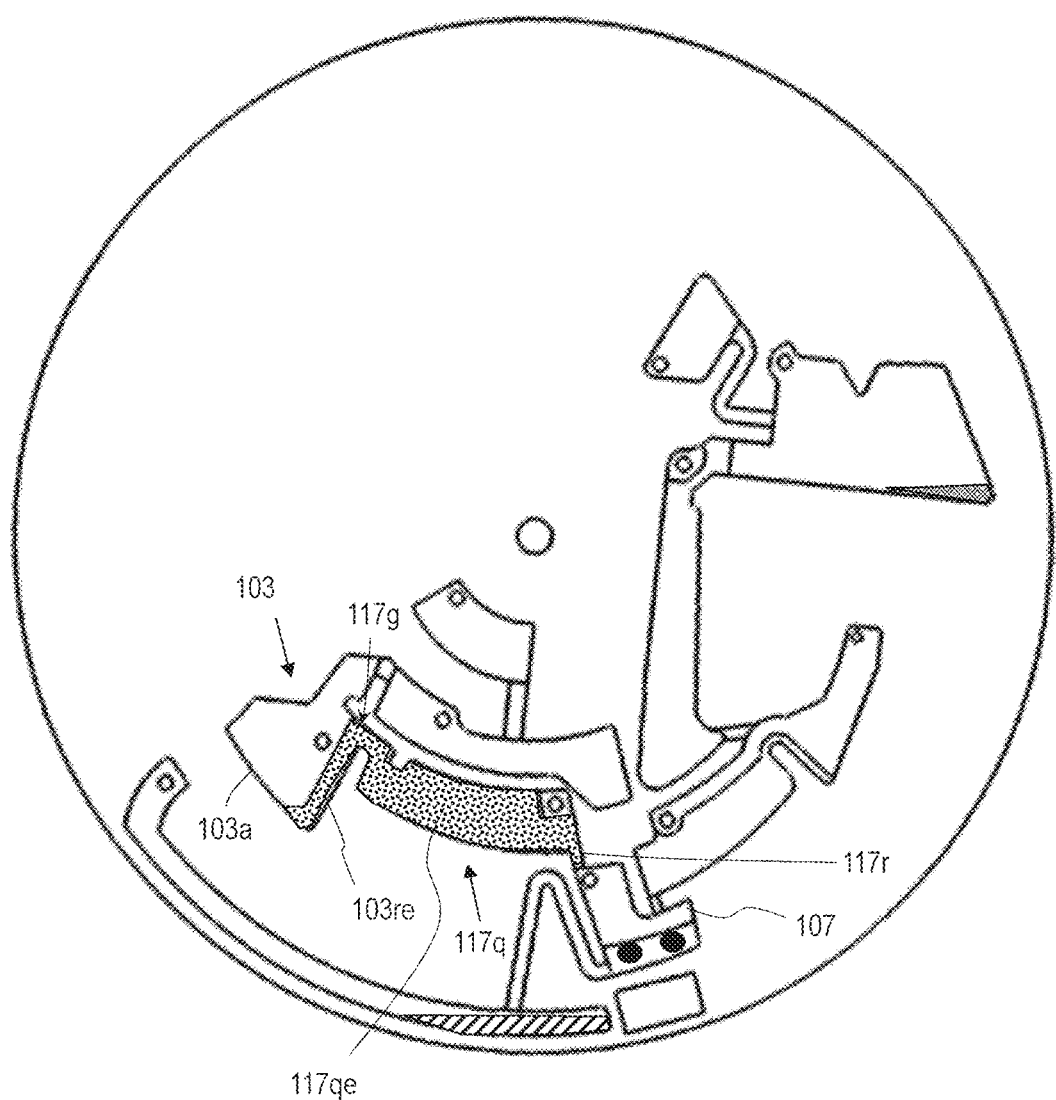
FIG. 21 schematically shows an example of angle at which the sample analysis substrate is stopped and an example of position of the liquid during the operation of the sample analysis system.

Next, as shown in FIG. 20, the sample analysis substrate 100 is rotated clockwise and is stopped at a predetermined ninth angle, at which the substrate solution in the third holding chamber 103 contacts the capillary space 103re of the second portion 103r. As a result of the capillary space 103re contacting the substrate solution, the substrate solution is absorbed into the capillary space 103re. As shown in FIG. 21, the substrate solution filling the capillary space 103re is absorbed into the seventh flow path 117 via the opening 117g by a capillary force, and the first region 117qe of the first portion 117q and the second portion 117r of the seventh flow path 117 are filled with the substrate solution. Thus, the substrate solution is weighed out.

In order to guarantee that the seventh flow path 117 is filled with the substrate solution, the sample analysis substrate 100 may be rotated several times clockwise and counterclockwise alternately, namely, may be swung, around the ninth angle. At this point, the washing solution does not move from the second portion 112r of the seventh flow path 117 to the main chamber 107 because a capillary force acts on the seventh flow path 117.

[Step S23]

Next, the sample analysis substrate 100 is rotated. A centrifugal force provided by the rotation acts on the washing solution in the seventh flow path 117 and the first holding chamber 101. The substrate solution in the seventh flow path 117 moves to the main chamber 107 by the centrifugal force. The substrate solution that is located on the side of the third holding chamber 103 with respect to the opening 112g is pressed onto the outermost side surface 102a of the third holding chamber 103 by a centrifugal force and thus stays in the third holding chamber 103.

The substrate solution moved to the main chamber 107 contains a substrate substance. As a result of the substrate substance reacting with the labeling substance 307 contained in the labeled antibody 308 in the magnetic particles 311 held in the main chamber 107, or as a result of a catalyst reaction of the labeling substance 307, light emission, fluorescence or change in the absorption wavelength occurs.

Figure 22:
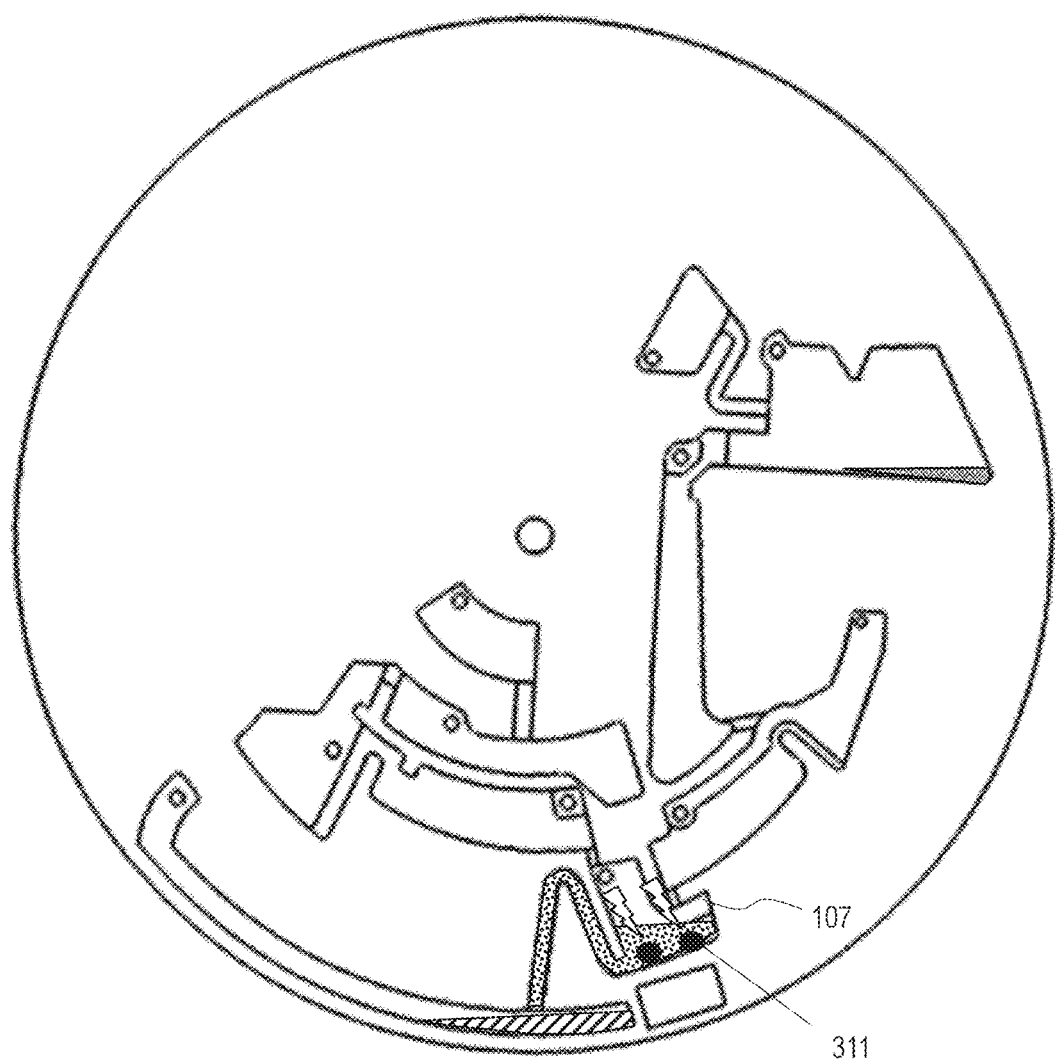
FIG. 22 schematically shows an example of angle at which the sample analysis substrate is stopped and an example of position of the liquid during the operation of the sample analysis system.

After the transfer of the substrate solution to the main chamber 107 is finished, as shown in FIG. 22, the rotation of the sample analysis substrate 100 is stopped at a tenth angle. The tenth angle is an angle at which the main chamber 107 is located at a predetermined angle with respect to the optical measurement unit 207 such that the light receiving element of the optical measurement unit 207 is, for example, close to the main chamber 107 so as to detect the light emission, fluorescence or change in the absorption wavelength of the substrate solution in main chamber 107.

[Step 24]

The optical measurement unit 207 performs optical measurement on a liquid held in the main chamber 107. Specifically, the optical measurement unit 207 detects a signal such as the colorant, light emission, fluorescence or the like of the substrate substance in accordance with the labeling substance 307 of the labeled antibody 308 bound to the complex body 310 contained in the magnetic particles 311. Thus, the detection of the antigen 306, the quantization of the concentration of the antigen 306, or the like is performed.

The optical measurement by the optical measurement unit 207 may be performed in the state where the sample analysis substrate 100 is rotating. In this case, in step S21, after the transfer of the substrate solution to the main chamber 107 is finished, a signal such as the colorant, light emission, fluorescence or the like of the substrate substance may be detected in the state where the sample analysis substrate 100 is rotating.

As described above, in this embodiment, the first holding chamber 101 holding the washing solution is connected with the reaction chamber 106 via the first flow path 111. The washing solution weighed out by use of the first flow path 111 is transferred to the main chamber 107, which holds the complex 310 to be washed, via the reaction chamber 106. Therefore, even in the case where the reaction solution remains in the reaction chamber 106, the reaction chamber 106 is washable by the washing solution. The remaining reaction solution is transferred to the chamber holding the complex body 310 and reacted with the substrate solution. Thus, a measurement error of the specimen is suppressed. Therefore, highly precise specimen analysis is performed.

In this embodiment, the first holding chamber 101 holding the substrate solution during the B/F separation and washing step has a space of a shape extending in the circumferential direction. In addition, the first holding chamber 101 has the opening of the sixth flow path 116 provided in one of two adjacent side surfaces thereof adjacent to the outermost side surface. The side surface having the opening faces the adjacent side surface close to the reaction chamber 106, the first holding chamber 101 holding the washing solution and the main chamber 107, and is located farther from these chambers. More specifically, the opening is provided at a position in such an adjacent side surface that is close to the rotation shaft 110. Therefore, regardless of the angle at which the sample analysis substrate 100 is rotated, the substrate solution does not easily contact the opening 111g of the sixth flow path 116 and is suppressed from being transferred to the third holding chamber 103.

(Other Embodiments of the Sample Analysis Substrate 100)

The sample analysis substrate 100 in the above-described embodiment may be modified in various manners.

[Other Examples of the Reaction Chamber 106]

In the above-described embodiment, the reaction chamber 106 includes the first portion 106q and the second portion 106r. The reaction chamber 106 does not need to include the first portion 106q.

Figure 23A:
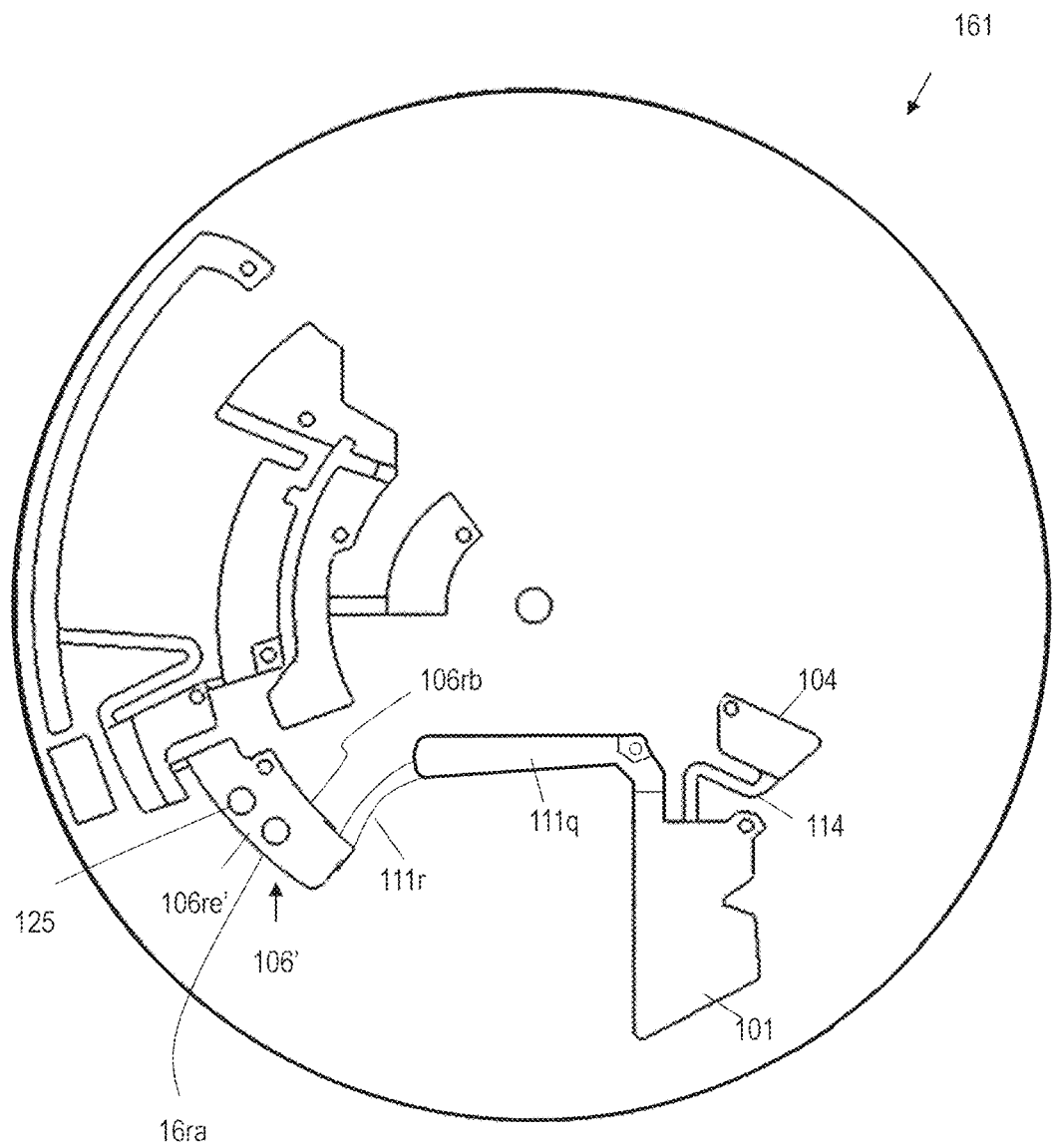
FIG. 23A is a plan view showing another example of sample analysis substrate.

In a sample analysis substrate 161 shown in FIG. 23A, a reaction chamber 106' includes only a second region 106re' of the second portion. The second portion 111r of the first flow path 111 faces the outermost side surface 106ra of the reaction chamber 106' and is connected with an innermost side surface 106rb closest to the rotation shaft 110. The second region 106re' holds the dried agent 125. The second region 106re' may be a capillary space or a non-capillary space. The dried agent 125 does not need to be held in the second region 106re'. In this case, the magnetic particle-immobilized antibody 305 and the labeling substance 307 may be introduced into the reaction chamber 106' together with the specimen solution, or may be transferred from another chamber.

Even in the case where the reaction chamber 106' having such a structure is provided, the washing solution is transferred to the main chamber 107 via the reaction chamber 106'. Therefore, the effect of washing the reaction chamber 106' with the washing solution is provided. With this structure, step S16 and step S20, among the above-described operations of the sample analysis system 501, may be omitted. The second flow path 112 may be a flow path in which a liquid is transferable by a capillary force or a flow path in which a liquid is transferable by a gravitational force.

Figure 23B:
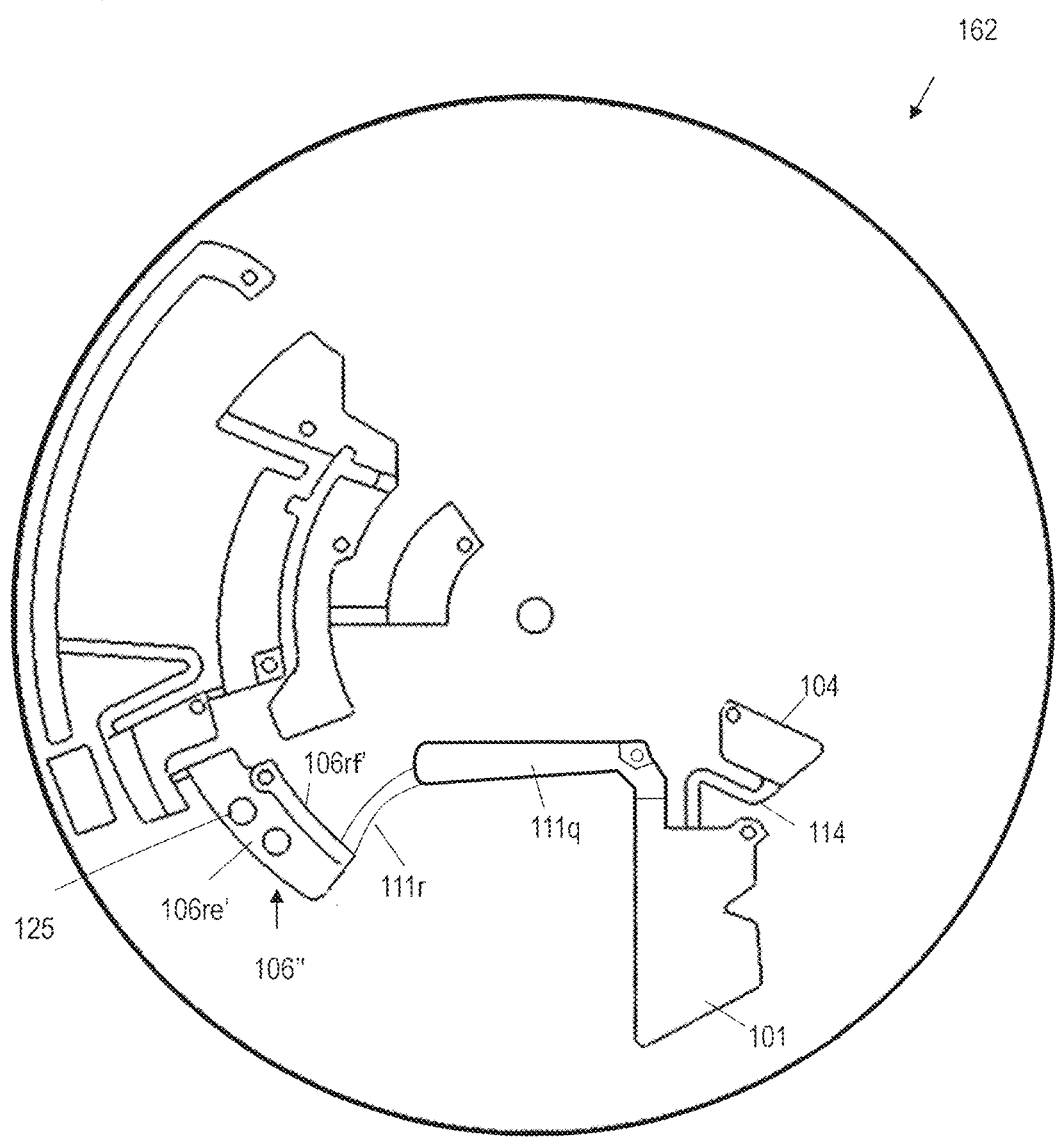
FIG. 23B is a plan view showing still another example of sample analysis substrate.

In a sample analysis substrate 162 shown in FIG. 23B, a reaction chamber 106" includes a first region 106rf and a second region 106re' of the second portion, but does not include the first portion. The first region 106rf is a non-capillary space, and the second region 106re' is a capillary space. In the example shown in FIG. 23B, the dried agent 125 is located in the second region 106re'. Alternatively, the dried agent 125 does not need to be provided.

Even in the case where the reaction chamber 106" having such a structure is provided, the washing solution is transferred to the main chamber 107 via the reaction chamber 106". Therefore, the effect of washing the reaction chamber 106" with the washing solution is provided. With this structure, step S16 and step S20, among the above-described operations of the sample analysis system 501, may be omitted. The second flow path 112 may be a flow path in which a liquid is transferable by a capillary force or a flow path in which a liquid is transferable by a gravitational force.

[Other Examples of the First Flow Path 111]

In the above-described embodiment, the first flow path 111 has a capillary space usable to weigh out the washing solution. The first flow path 111 does not need to have a function of weighing out a liquid.

Figure 24A:
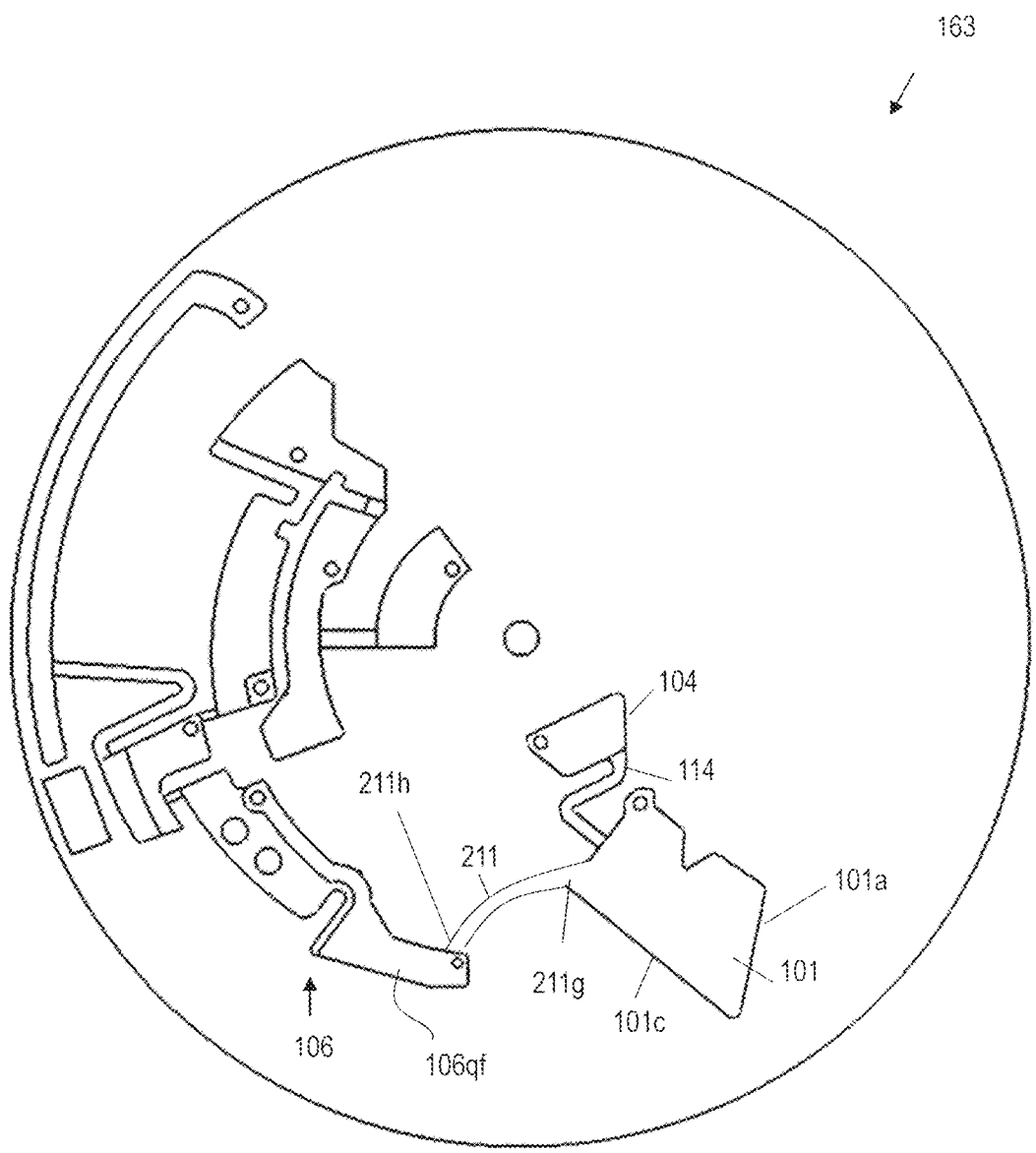
FIG. 24A is a plan view showing still another example of sample analysis substrate.

Unlike the sample analysis substrate 100, a sample analysis substrate 163 shown in FIG. 24A includes a first flow path 211, in which a liquid is transferable by a gravitational force.

In the case where the first flow path 211 does not have a function of weighing out a liquid, the rotation angle of the sample analysis substrate 163 may be controlled to control the amount of the washing solution to be transferred from the first holding chamber 101 to the first flow path 211, so that the washing solution is transferred to the reaction chamber 106 as being divided into a plurality of portions.

The first holding chamber 101 has the outermost side surface 101a farthest from the rotation shaft 110 and an adjacent side surface 101c adjacent to the outermost side surface 101a. The outermost side surface 101a and the adjacent side surface 101c define a recessed space having an opening opened toward the rotation shaft 110. The first flow path 211 is a flow path in which a liquid is transferable by a gravitational force, and has an opening 211g and an opening 211h. The opening 211g is located at a position, in the adjacent side surface 101c, that is closer to the rotation shaft 110. The opening 211h of the first flow path 211 is connected with the first region 106qf of the first portion 106q of the reaction chamber 106.

As described above, in the case where the sample analysis substrate 163 is held at an angle at which the washing solution held in the first holding chamber 101 contacts the opening 211g, the washing solution starts flowing into the first flow path 211 by a gravitational force, and the movement of the washing solution causes the surface of the washing solution to retract. The washing solution is transferred to a position matching the opening 211g. Therefore, the angle at which the sample analysis substrate 163 is held may be changed, so that the washing solution is transferred to the reaction chamber 106 a plurality of times.

Figure 24B:
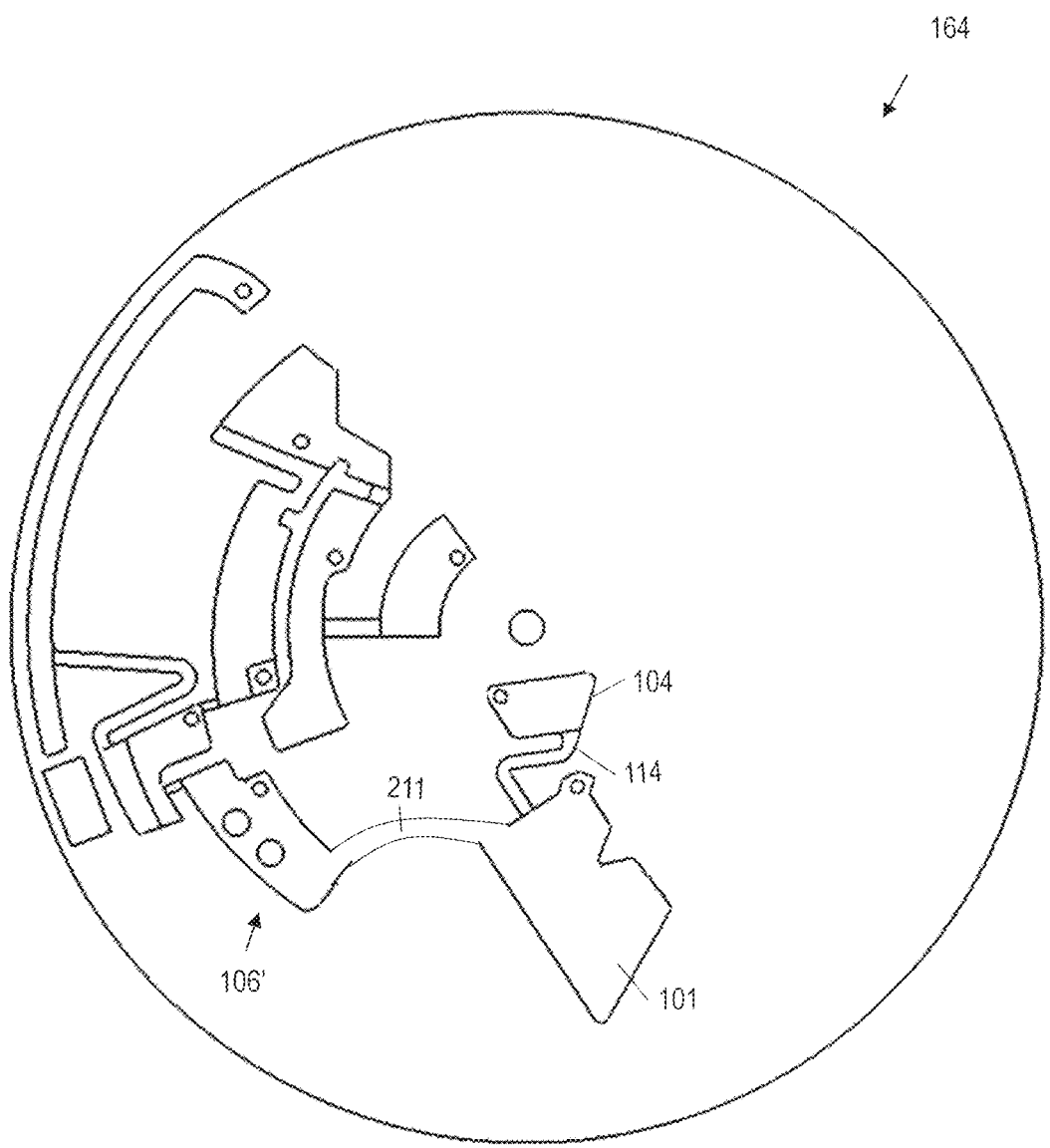
FIG. 24B is a plan view showing still another example of sample analysis substrate.
Figure 24C:
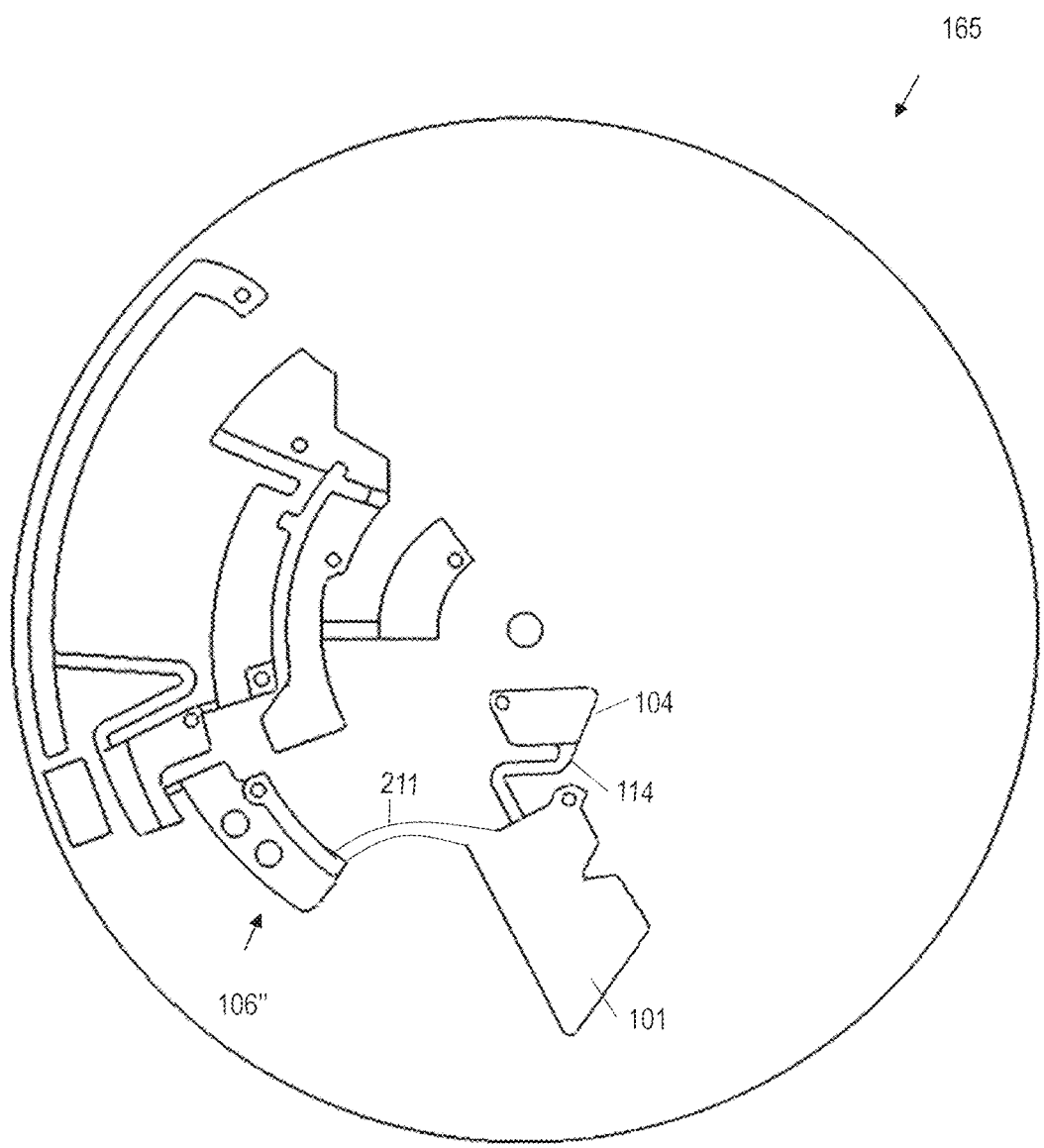
FIG. 24C is a plan view showing still another example of sample analysis substrate.

A sample analysis substrate 164 shown in FIG. 24B and a sample analysis substrate 165 shown in FIG. 24C are further modifications of the sample analysis substrate 163. Unlike the sample analysis substrate 163, the sample analysis substrate 164 and the sample analysis substrate 165 respectively include the reaction chamber 106' shown in FIG. 23A and the reaction chamber 106" shown in FIG. 23B. Even with such a sample analysis substrate, the above-described effect of washing the reaction chamber is provided.

Figure 25A:
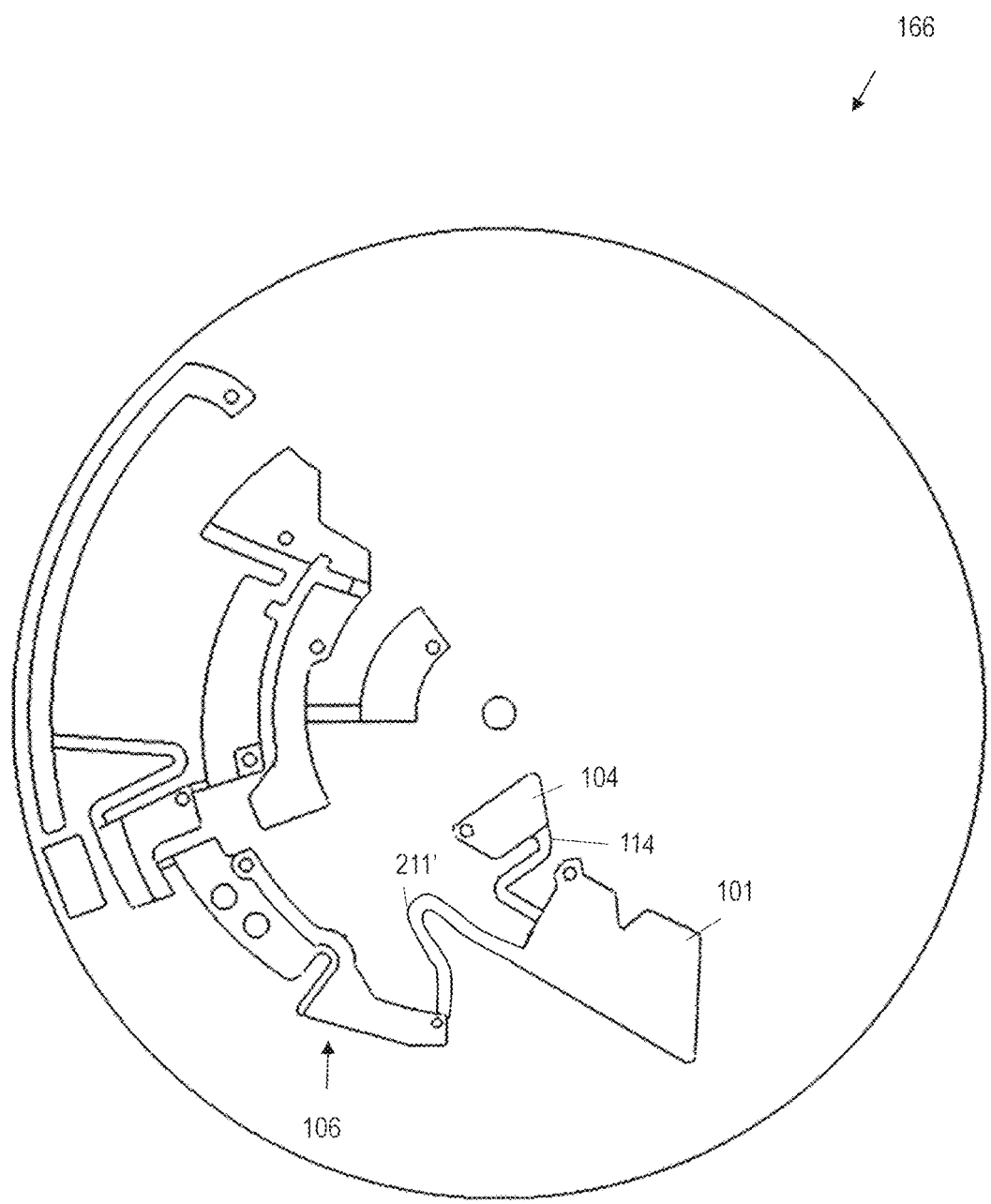
FIG. 25A is a plan view showing still another example of sample analysis substrate.
Figure 25B:
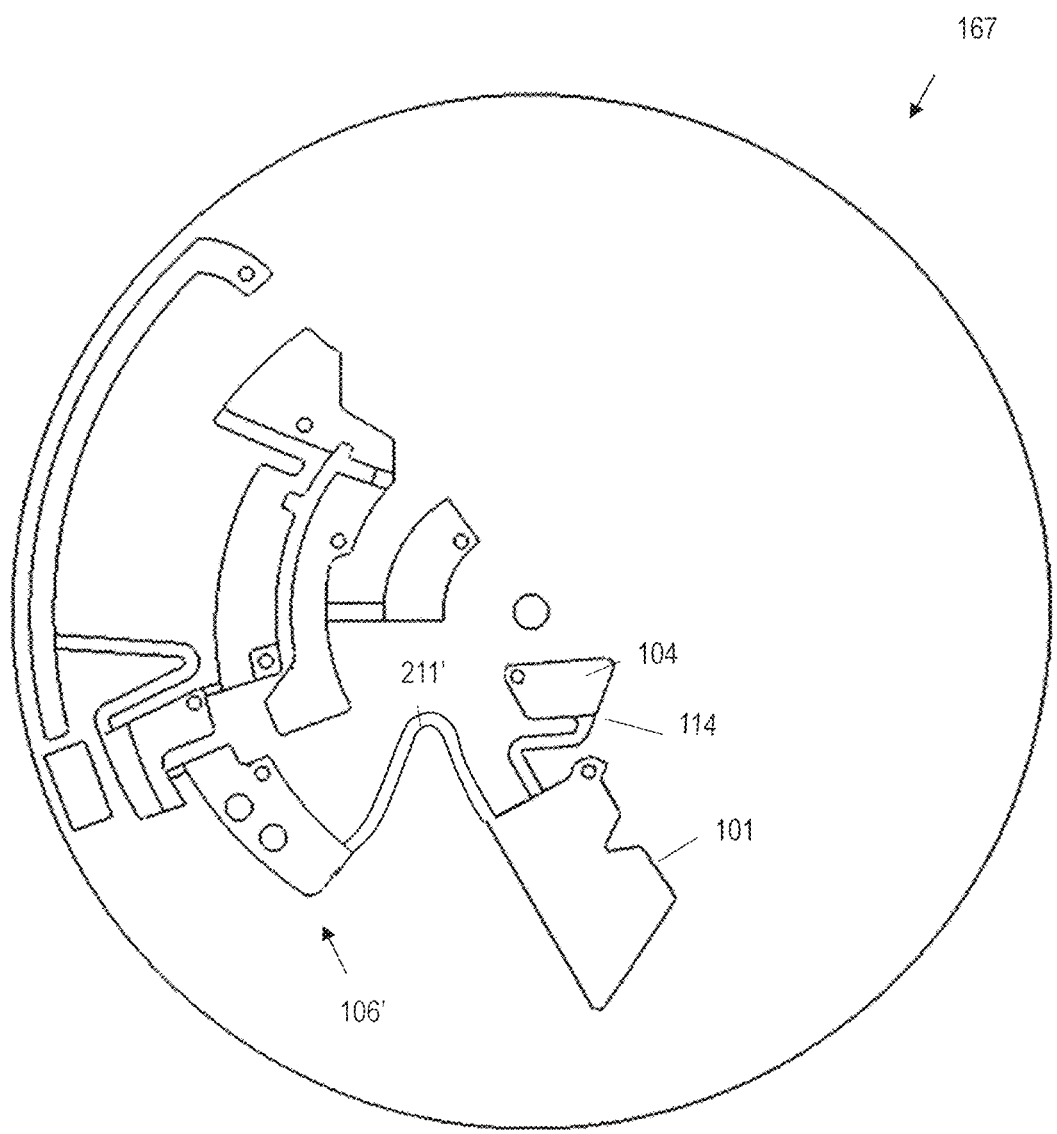
FIG. 25B is a plan view showing still another example of sample analysis substrate.
Figure 25C:
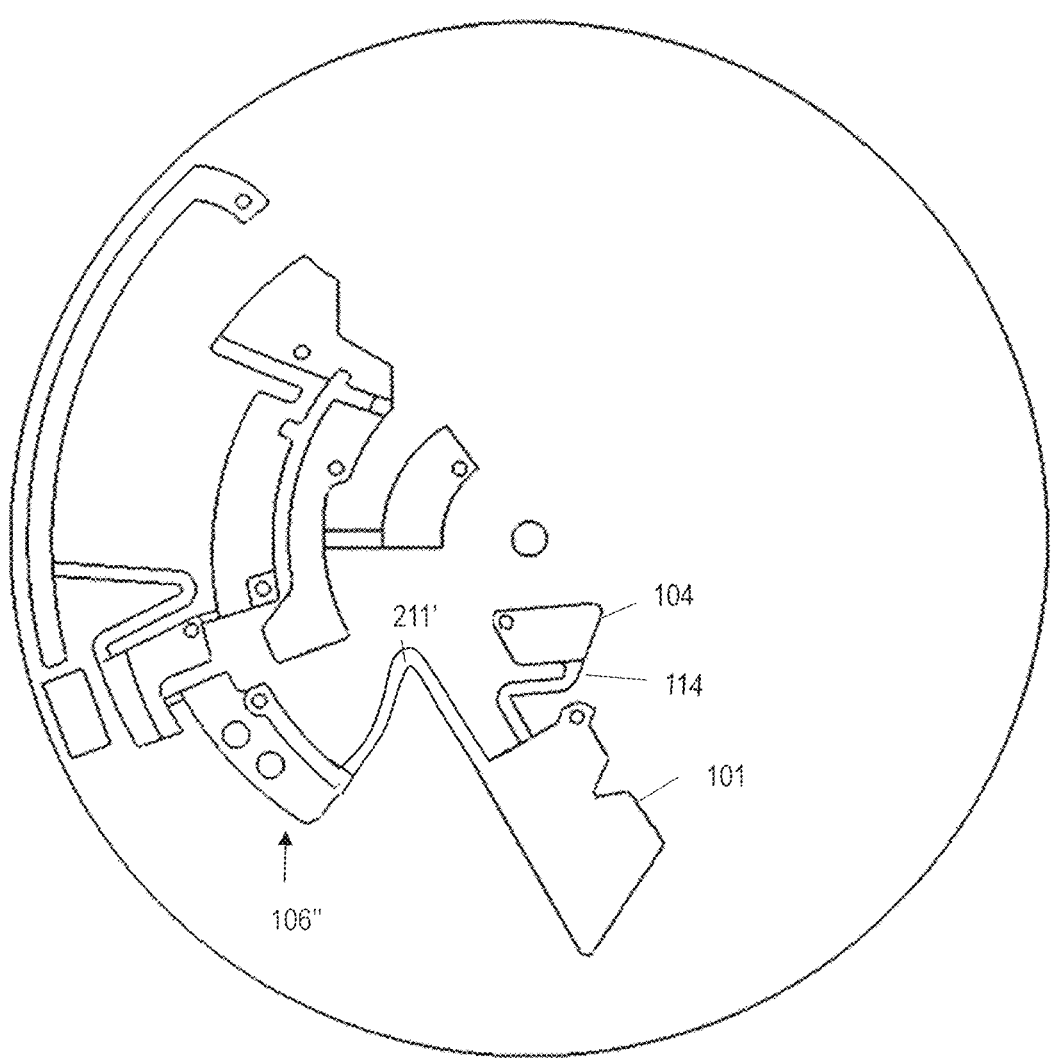
FIG. 25C is a plan view showing still another example of sample analysis substrate.

The first flow path may be of a type in which a liquid is transferable by a capillary force. Sample analysis substrates 166, 167 and 168 shown in FIG. 25A through FIG. 25C each include a first flow path 211', in which a liquid is transferable by a capillary force, instead of the first flow path 211 included in each of the sample analysis substrates 163, 164 and 165 shown in FIG. 24A through FIG. 24C. In this case, it is preferred that the first flow path 211' has a siphon structure. With the siphon structure, in the case where the reaction solution held in the reaction chamber is to be transferred to the main chamber, the washing solution transferred from the first storage chamber 104 to the first holding chamber 101 is prevented from being transferred to the reaction chamber via the first flow path 211' as it is.

With such a structure, the washing solution is transferred from the first holding chamber 101 to the reaction chamber 106, 106' or 106" by a centrifugal force provided by the rotation of the sample analysis substrate. Therefore, it is difficult to transfer the washing solution to the reaction chamber 106, 106' or 106" as being divided into a plurality of portions.

[Another Example of the First Holding Chamber and the First Flow Path]

In the above-described embodiment, the washing solution is weighed out by use of first flow path 111. Alternatively, the washing solution may be weighed out by use of the first holding chamber. A sample analysis substrate 169 shown in FIG. 26 includes a first holding chamber 133, which includes a first portion 133q, a second portion 133r, and a coupling portion 133p connecting the second portion 133r and the first portion 133q to each other.

In this embodiment, the second portion 133r and a part of the first portion 133q are generally aligned in a circumferential direction of a circle centered around the rotation shaft 110. A wall portion 100f formed of an inner surface of the substrate 100' is located between second portion 133r and the first portion 133q. The wall portion 100f separates the second portion 133r and the first portion 133q from each other. The coupling portion 133p is aligned with the wall portion 100f of the substrate 100' in the radial direction, and is located closer to the rotation shaft 110 than the wall portion 100f. The coupling portion 133p is not filled with a liquid by a capillary action, and causes the liquid to move between the first portion 133q and the second portion 133r by a gravitational force.

The second portion 133r includes a portion 133re located outer (in a direction away from the rotation shaft 110) to an arc ca. The arc ca is centered around the rotation shaft 110 and has, as a radius, a line segment connecting the rotation shaft 110 and a point 100e in the wall portion 100f that is closest to the rotation shaft. The portion 133re is usable to weigh out a predetermined amount of washing solution needed for one cycle of washing.

The distance from the rotation shaft 110 to the opening 111g, of the first flow path 111, provided in the second portion 133r is longer than the distance from the rotation shaft 110 to the point 100e, in the wall portion 100f, that is closest to the rotation shaft 110. Therefore, the washing solution weighed out by use of the portion 133re is transferred from the first flow path 111 to the reaction chamber 106 by a centrifugal force provided by the rotation.

The first portion 133q of the first holding chamber 133 includes a side portion 133qt and a bottom portion 133qs. The side portion 133qt is located to the side of the first storage chamber 104 on a circumferential direction of a circle centered around the rotation shaft 110. The bottom portion 133qs is located farther from the rotation shaft 110 than the first storage chamber 104. A part of the side portion 133qt and the entirety of the bottom portion 133qs of the first portion 133q are located farther from the rotation shaft 110 than the second portion 133r.

Preferably, the side portion 133qt includes a portion 133qt' located closer to the rotation shaft 110 than the arc ca, and a portion 133qt" located outer to the arc ca. As described above, the portion 133qt' is adjacent to the first portion 133q in the circumferential direction and is connected with the coupling portion 133p.

It is preferred that portions of the first portion 133q, of the first holding chamber 133, that are outer (in a direction away from the rotation shaft 110) to the arc ca, namely, the portion 133qt" and the bottom portion 133qs have a total capacity larger than the total amount of the washing solution held in the first storage chamber 104.

The space of the first holding chamber 133 includes the bottom portion 133$qs$. Therefore, in the state where the sample analysis substrate 169 is stopped at a predetermined angle, a part of the washing solution held in the first storage chamber 104 fills the fourth flow path 114 by a capillary action. The sample analysis substrate 169 is rotated in the state where the fourth flow path 114 is filled with the washing solution, and thus the washing solution in the first storage chamber 104 is transferred to the bottom portion 133$qs$ via the fourth flow path 114 by a centrifugal force provided by the rotation.

In the case where the sample analysis substrate 169 is held at a predetermined angle, a part of the washing solution transferred to the bottom portion 133$qs$ of the first holding chamber 133 flows into the second portion 133$r$ via the coupling portion 133$p$ by a gravitational force, and fills at least a part of the second portion 133$r$. Then, when the sample analysis substrate 100 is rotated, a centrifugal force acts on the washing solution filling the second portion 133$r$. As a result, an extra portion of the washing solution held in the second portion 133$r$ is returned to the first portion 133$q$, such that the arc ca (represented by the dotted line in FIG. 26) having, as the radius, the line segment connecting the rotation shaft 110 and the point 100$e$ in the wall portion 100$f$ that is closest to the rotation shaft 110 matches the liquid surface of the washing solution in the second portion 133$r$. Thus, a predetermined amount of washing liquid is weighed out. The capacity of the portion of the second portion 133$r$ that is located outer to the arc ca having, as the radius, the line segment connecting the rotation shaft 110 and the point 100$e$ in the wall portion 100$f$ that is closest to the rotation shaft 110 is ½ or less of the capacity of the first holding chamber 133.

Figure 26:
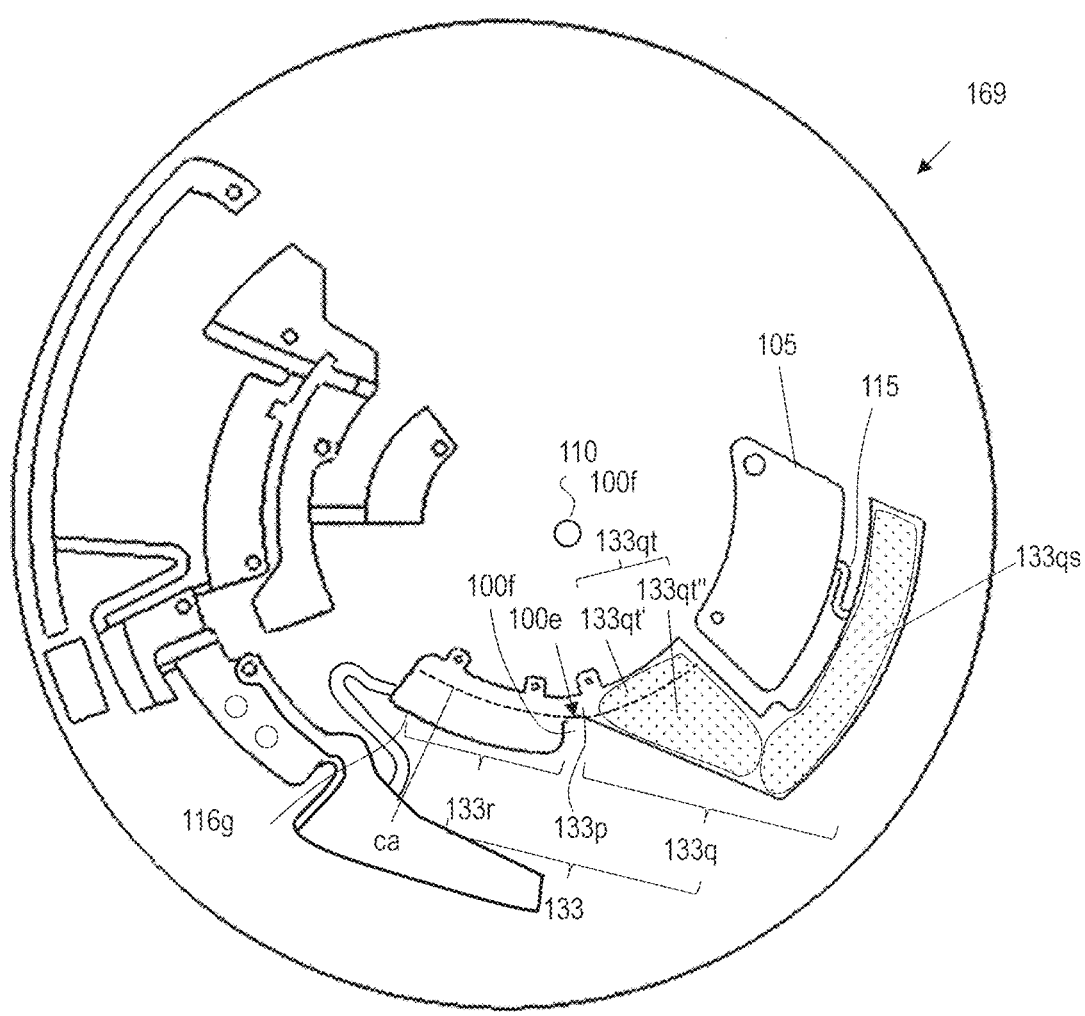
FIG. 26 is a plan view showing still another example of sample analysis substrate.

In the example shown in FIG. 26, the first portion 133$q$ includes a part of the side portion 133$qt$ and the bottom portion 133$qs$. It is sufficient that the first portion 133$q$ includes the portion outer to the arc that is centered around the rotation shaft 110 and has, as the radius, the line segment connecting the rotation shaft 110 and the point 100$e$ in the wall portion 100$f$ that is closest to the rotation shaft 110.

The certain amount of washing solution weighed out by use of the first holding chamber 133 fills the first flow path 111 by a capillary action. Then, the sample analysis substrate 169 is rotated at a rotation rate that provides a centrifugal force stronger than the capillary force applied to the liquid in the first flow path 111, and thus the washing liquid is transferred to the main chamber 107 via the first flow path 111 by a centrifugal force provided by the rotation.

The sample analysis substrate 169 shown in FIG. 26 includes the reaction chamber 106 shown in FIG. 3B or the like. Alternatively, the sample analysis substrate 169 may include the reaction chamber 106' or 106" shown in FIG. 23A or FIG. 23B.

[Another Example of the Chambers Holding the Washing Solution]

In the above-described embodiment, the first holding chamber 101 holds the washing solution needed for a plurality of cycles of washing. Alternatively, there may be a plurality of chambers each holding the washing solution needed for one cycle of washing.

Figure 27:
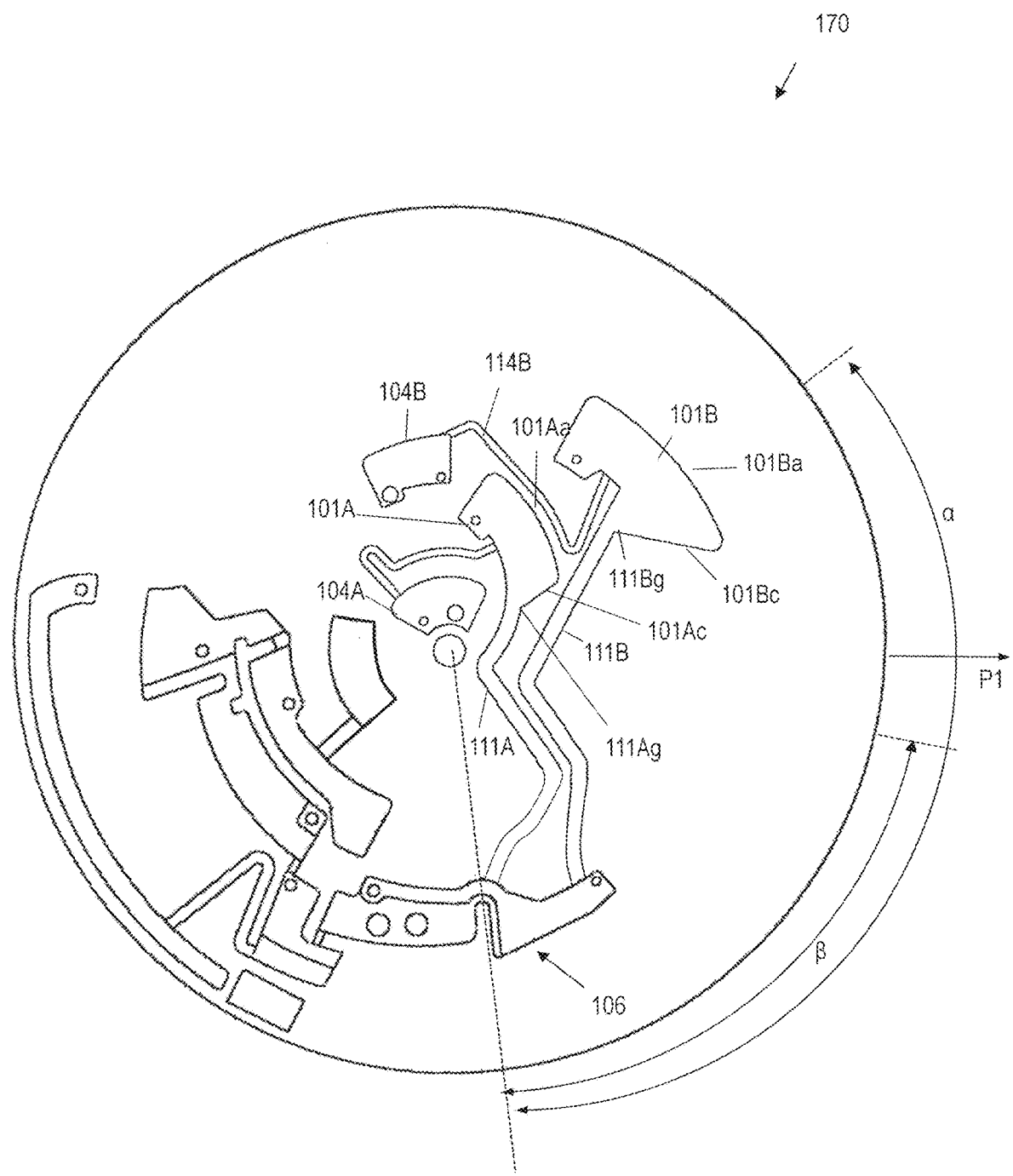
FIG. 27 is a plan view showing still another example of sample analysis substrate.

A sample analysis substrate 170 shown in FIG. 27 includes a first storage chamber 104A, a third storage chamber 104B, a fourth flow path 114A, an eighth flow path 114B, a first holding chamber 101A, a fourth holding chamber 101B, a first flow path 111A and a tenth flow path 111B.

The first storage chamber 104A, the fourth flow path 114A, the first holding chamber 101A and the first flow path 111A hold the washing solution needed for one cycle of washing and form a channel transferring the washing solution to the reaction chamber 106. The third storage chamber 104B, the eighth flow path 114B, the fourth holding chamber 101B and the tenth flow path 111B hold the washing solution needed for one cycle of washing and form a channel transferring the washing solution to the reaction chamber 106.

The fourth flow path 114A connects the first chamber 104A and the first holding chamber 101A to each other, and the eighth flow path 114B connects the third storage chamber 104B and the fourth storage chamber 101B to each other. The first flow path 111A connects the first holding chamber 101A and the reaction chamber 106 to each other. The tenth flow path 111B connects the fourth holding chamber 101B and the reaction chamber 106 to each other.

The fourth flow path 114A and the eighth flow path 114B are capillary channels, and each have a siphon structure. By contrast, the first flow path 111A and the tenth flow path 111B each have a structure in which a liquid is transferable by a gravitational force. The first holding chamber 101A and the first flow path 111A are respectively located farther from the rotation shaft 110 than the first storage chamber 104A and the third storage chamber 104B. The first flow path 111A and the tenth flow path 111B are flow paths in which a liquid is transferable by a gravitational force.

The first holding chamber 101A has an outermost side surface 101Aa and an adjacent side surface 101Ac adjacent to the outermost side surface 101Aa. A tapering surface, a curved surface or the like smoothing the angle (ridge) may be provided between the outermost side surface 101Aa and the adjacent side surface 101Ac. An opening 111Ag of the first flow path 111A is located at an one of two ends of the adjacent side surface 101Ac at which the outermost side surface 101Aa is not located. The outermost side surface 101Aa and the adjacent side surface 101Ac define a recessed portion opened toward the rotation shaft 110, and the recessed portion holds the washing liquid needed for one cycle of washing.

Similarly, the fourth holding chamber 101B includes an outermost side surface 101Ba and an adjacent side surface 101Bc adjacent to the outermost side surface 101Ba. A tapering surface, a curved surface or the like smoothing the angle (ridge) may be provided between the outermost side surface 101Ba and the adjacent side surface 101Bc. An opening 111Bg of the tenth flow path 111B is located at an one of two ends of the adjacent side surface 101Bc at which the outermost side surface 101Ba is not located. The outermost side surface 101Ba and the adjacent side surface 101Bc define a recessed portion opened toward the rotation shaft 110, and the recessed portion holds the washing liquid needed for one cycle of washing.

As shown in FIG. 27, two regions are separated from each other by a straight line connecting the center of the reaction chamber 106 and the rotation shaft 110. The first holding chamber 101A and the fourth holding chamber 101E are both located in the same region.

The sample analysis substrate 170 is supported such that the rotation shaft 110 is inclined with respect to the direction of gravity at an angle that is larger than 0 degrees and 90 degrees or smaller, such that the recessed portion of the first chamber 101A and the recessed portion of the fourth holding chamber 101B hold a liquid. The sample analysis substrate 170 is held at a predetermined rotation angle such that the reaction chamber 106 is located below the first holding chamber 101A and the fourth holding chamber 101B in the direction of gravity. In this case, the adjacent side surface 101Ac of the first holding chamber 101A and the adjacent side surface 101Bc of the fourth holding chamber 101E are unparallel to each other as seen from a direction parallel to the rotation shaft 110. With such an arrangement, even if all the washing solution held in either one of the chambers is transferred to the reaction chamber 106 by a gravitational force, the other chamber may hold at least a part of the washing solution. Therefore, in the case where the rotation angle of the sample analysis substrate 170 is appropriately selected, the washing solution may be transferred to the reaction chamber 106 from the first holding chamber 101A and the fourth holding chamber 101E selectively at different timings.

In the example shown in FIG. 27, as seen from a direction parallel to the rotation shaft 110, angle α of the adjacent side surface 101Ac with respect to a straight line connecting the center of the reaction chamber 106 and the rotation shaft 110 is larger than angle β of the adjacent side surface 101Bc with respect to the straight line. Therefore, in the case where the sample analysis substrate 170 is rotated counterclockwise from a rotation angle at which the first holding chamber 101A and the fourth holding chamber 101B are located below the reaction chamber 106 in the direction of gravity (rotation angle at which P1 in FIG. 27 matches the direction of 6 o'clock), the adjacent side surface 101Ac first becomes parallel to a direction perpendicular to the direction of gravity (becomes horizontal). As a result, all the washing solution in the first holding chamber 101A is selectively transferred to the reaction chamber 106. Then, the washing solution held in the fourth holding chamber 101B is selectively transferred to the main chamber 107.

[Other Examples of the Reaction Chamber]

In the reaction chamber 106 of the sample analysis substrate 100 described above with reference to FIG. 3C and the like, the first portion 106q and the second portion 106r respectively have a capillary space and a non-capillary space. The capillary space and the non-capillary space in the reaction chamber are not limited to having such a structure, and may be modified in various other forms.

Figure 28A:
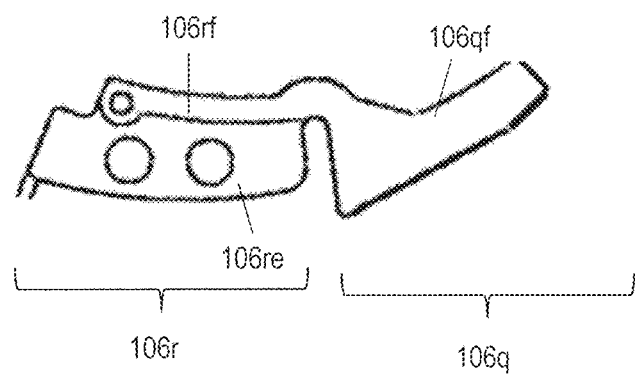
FIG. 28A is a plan view showing another example of reaction chamber.

For example, as shown in FIG. 28A, the reaction chamber may include a first portion 106q including only a first region 106qf and a second portion 106r including a first region 106rf and a second region 106re. Namely, in the reaction chamber 106 shown in FIG. 3C and the like, the second region 106qe of the first portion 106q may be omitted. In this case, in the second portion 106r, the first region 106rf is located closer to the rotation shaft 110 than the second region 106re, and the first region 106rf is connected with the first region 106qf of the first portion 106q. The first region 106qf and the first region 106rf are non-capillary spaces, whereas the second region 106re is a capillary space.

Figure 28B:
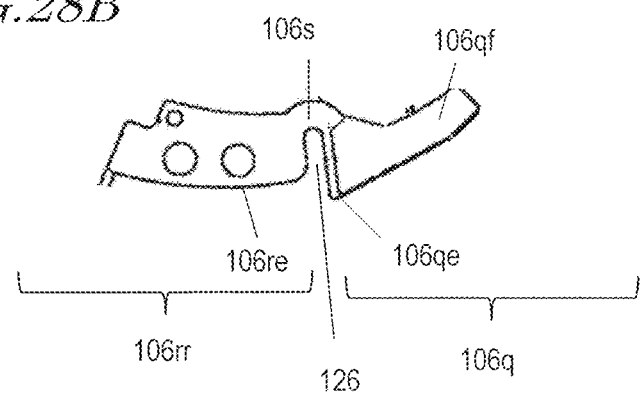
FIG. 28B is a plan view showing still another example of reaction chamber.
Figure 28C:
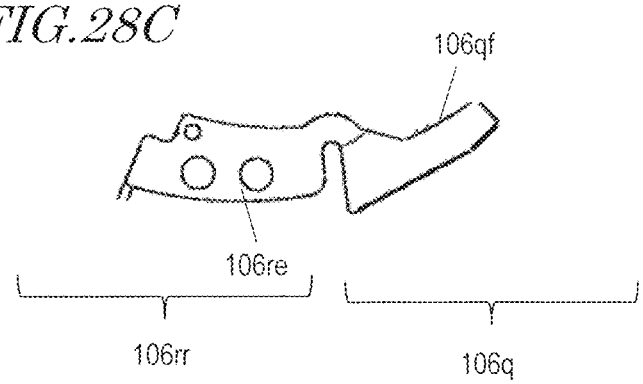
FIG. 28C is a plan view showing still another example of reaction chamber.

As shown in FIG. 28B, the second portion 106r does not need to include the first region 106rf. In this case, the second portion 106r includes only the second region 106re, which is a capillary space. The second region 106re is connected with the second region 106qe of the first portion 106q. The second region 106re of the first portion 106q may include a region around the wall portion 126 and also a portion 106s, which is located closer to the rotation shaft 110 than the wall portion 126 and is connected with the second portion 106r.

Figure 28D:
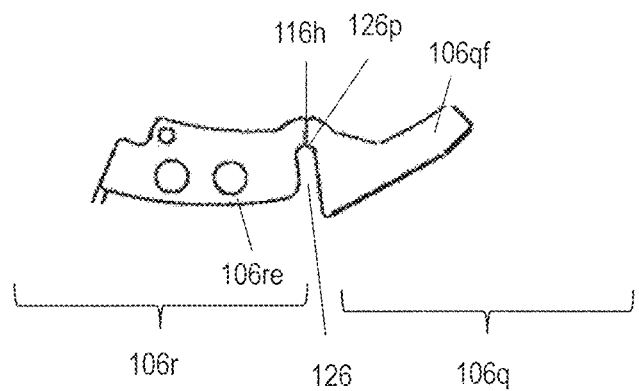
FIG. 28D is a plan view showing still another example of reaction chamber.

As shown in FIG. 28D, the first portion 106q may include only the first region 106qf, which is a non-capillary space, whereas the second portion 106r may include only the second region 106re, which is a capillary space. In this case, a border (connection portion) between the first portion 106q and the second portion 106r is located on a radius connecting the rotation shaft 110 and the point 126p, in the wall portion 126, that is closest to the rotation shaft 110.

Figure 28E:
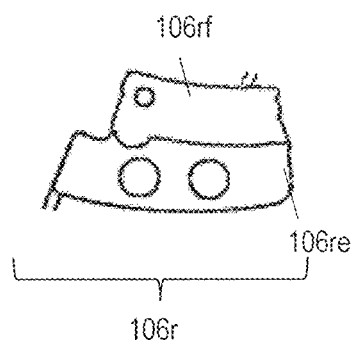
FIG. 28E is a plan view showing still another example of reaction chamber.

As shown in FIG. 28E, the reaction chamber does not need to include the first portion. In this case, the first portion 106q includes the first region 106qf and the second region 106qe, and the first region 106qf may be located closer to the rotation shaft 110 than the second region 106qe.

Other Modification Examples

In this embodiment, a measurement system using magnetic particles is assumed. The sample analysis substrate, the sample analysis device, the sample analysis system and the program for the sample analysis system in an embodiment according to the present application are not limited to the measurement system using the magnetic particles. For example, the target on which the primary antibody is immobilized may be a wall in the chamber instead of the magnetic particle. Namely, in the case where the chamber is formed of a material such as polystyrene, polycarbonate or the like, the primary antibody may be immobilized to the wall in the chamber by physical adsorption and a binding reaction with the antigen or the labeled antibody in a sandwich manner may be caused in the chamber. Alternatively, in the case where a functional group bindable with the primary antibody (e.g., amino group or carboxyl group) is provided on the wall in the chamber, the primary antibody may be immobilized by chemical bonding and a binding reaction with the antigen or the labeled antibody in the sandwich manner may be caused in the chamber. In the case where the wall in the chamber includes a metal substrate, the primary antibody may be bound and immobilized to the metal substrate by use of, for example, SAM and a binding reaction with the antigen or the labeled antibody in the sandwich manner may be caused in the chamber. Immobilization of the primary antibody to the wall in the chamber by physical adsorption or chemical bonding is mainly usable for a system detecting a signal such as colorant, chemical light emission or fluorescence. By contrast, immobilization of the primary antibody to the metal substrate is mainly used for a system detecting an electrochemical signal (e.g., electric current) or electrochemical light emission signal. In this case, the magnet 121 shown in FIG. 3B is not necessary. The reaction field in which the complex body 310 is formed is not the reaction chamber 106, but is the main chamber 107. Therefore, the primary antibody needs to be immobilized to the wall of the main chamber 107.

The sample analysis substrate, the sample analysis device, the sample analysis system and the program for the sample analysis system according to this disclosure are applicable to a competitive immunoassay and a gene detection method by use of hybridization as well as the sandwich immunoassay.

In the above-described embodiment, an example of washing for the B/F separation is described. The sample analysis substrate, the sample analysis device and the sample analysis system in this embodiment are applicable to any of various sample analysis methods in which a solution other than the washing solution is introduced into the chamber as being divided into a plurality of portions as described above. In the above-described embodiment, the liquid is continuously introduced into the chamber. Alternatively, the operation of rotating and stopping the sample analysis substrate, and the angle at which the sample analysis substrate is stopped, may be controlled appropriately, so that another step(s) may be performed during the introduction.

In the above-described embodiment, the washing is performed twice. The washing may be performed three or more times optionally.

INDUSTRIAL APPLICABILITY

The sample analysis substrate, the sample analysis device, the sample analysis system and the program for the sample analysis system disclosed in the present application are applicable to analysis of a specific component in a specimen using any of various reactions.

REFERENCE SIGNS LIST 100 sample analysis substrate
100' substrate
100a base plate
100b cover plate
100c, 100d main surface
100f wall portion
101, 101A first holding chamber
101B fourth holding chamber
101a, 102a outermost side surface
101c, 101d adjacent side surface
102 second holding chamber
103 third holding chamber
104 first storage chamber
105 second storage chamber
106 main chamber
106q first portion
106qa outermost side surface
106qe second region
106qf first region
106r second portion
106ra outermost side surface
106rb innermost side surface
106re second region
106rf first region
107 main chamber
108 recovery chamber
110 rotation shaft
111 first flow path
112 second flow path
113 third flow path
114 fourth flow path
115 fifth flow path
116 sixth flow path
117 seventh flow path
120 magnet accommodation chamber
121 magnet
122 air hole
123 opening
125 dried agent
126 wall
161-169 sample analysis substrate
200 sample analysis device
201 motor
201a turntable
203 origin detector
203a light source
203b light receiving element
203c origin detection circuit
204 rotation angle detection circuit
205 control circuit
206 driving circuit
207 optical measurement unit
210 marker
210a edge
210b edge
302 magnetic particle
304 primary antibody
305 magnetic particle-immobilized antibody
306 antigen
307 labeling substance
308 labeled antibody
310 complex body
311 magnetic particle
501 sample analysis system

The invention claimed is:

1. A sample analysis substrate rotatable to transfer a liquid, the sample analysis substrate comprising:
a substrate including a rotation shaft;
a first holding chamber located in the substrate, the first holding chamber having a first space usable to hold a first liquid;
a reaction chamber located in the substrate, the reaction chamber having a second space usable to hold a specimen-containing liquid sample;
a first flow path located in the substrate, the first flow path having a first opening and a second opening respectively connected with the first holding chamber and reaction chamber;
a main chamber located in the substrate, the main chamber having a space usable to hold the specimen-containing liquid sample and magnetic particles having a ligand immobilized to a surface thereof;
a second flow path located in the substrate, the second flow path having a third opening and a fourth opening respectively connected with the reaction chamber and the main chamber; and
a magnet accommodation chamber located in the substrate, the magnet accommodation chamber being capable of accommodating a magnet;
wherein:
the first opening is located closer to the rotation shaft than the second opening;
the second opening is located closer to the rotation shaft than the third opening;
the magnet accommodation chamber is located at a position at which, in the case where the magnet is accommodated in the magnet accommodation chamber, the magnet captures the magnetic particles in the main chamber;
the first flow path is a capillary channel; and
a part of the first flow path is located closer to the rotation shaft than a part of the first holding chamber with the first opening being located between the part of the first flow path and the part of the first holding chamber.

2. The sample analysis substrate of claim 1, further comprising a dried agent located in a space of the reaction chamber, wherein the dried agent contains the magnetic particles.

3. The sample analysis substrate of claim 1, wherein the reaction chamber has a non-capillary space.

4. The sample analysis substrate of claim 1, wherein the reaction chamber has a capillary space.

5. The sample analysis substrate of claim 1, wherein:
the reaction chamber has a non-capillary space and a capillary space;
the first opening is in contact with the non-capillary space; and
the third opening is in contact with the capillary space.

6. The sample analysis substrate of claim 5, wherein the non-capillary space includes a portion located closer to the rotation shaft than the capillary space.

7. The sample analysis substrate of claim 5, wherein:
the reaction chamber includes a first portion and a second portion;
the substrate includes a wall portion located between the first portion and the second portion of the reaction chamber;
the wall portion includes a protruding portion protruding toward the rotation shaft; and
the first portion and the second portion respectively include a part of the capillary space and a part of the non-capillary space located farther from the rotation shaft than an arc having, as a radius, a line segment connecting the rotation shaft and a point, in the wall portion, that is closest to the rotation shaft.

8. The sample analysis substrate of claim 7, wherein a part, of the capillary space, that connects the first portion and the second portion to each other is located in a part of, the wall portion, that is closer to the first portion or in the entirety of the wall portion.

9. The sample analysis substrate of claim 1, further comprising:
a recovery chamber located in the substrate, the recovery chamber having a space;
a third flow path located in the substrate, the third flow path having a fifth opening and a sixth opening respectively connected with the main chamber and the recovery chamber;
wherein the fifth opening is located closer to the rotation shaft than the sixth opening.

10. The sample analysis substrate of claim 1, wherein the first flow path is a non-capillary channel.

11. The sample analysis substrate of claim 10, wherein:
the first holding chamber has an outermost side surface farthest from the rotation shaft and an adjacent side surface adjacent to the outermost side surface;
the outermost side surface and the adjacent side define a recessed portion; and
in the case where the sample analysis substrate is held at a predetermined angle, the first liquid is held in the recessed portion.

12. The sample analysis substrate of claim 1, wherein the first flow path has a siphon structure.

13. The sample analysis substrate of claim 1, wherein:
the space of the first holding chamber includes a first portion, a second portion, and a coupling portion located between the first portion and the second portion, the coupling portion coupling the first portion and the second portion to each other;
the substrate includes a wall portion separating the first portion and the second portion of the space of the first holding chamber from each other;
the reaction chamber is located farther from the rotation shaft than the second portion of the first holding chamber;
the coupling portion of the space of the first holding chamber is located closer to the rotation shaft than the wall portion of the substrate; and
the first flow path is connected with the second portion of the space of the first holding chamber.

14. The sample analysis substrate of claim 1, further comprising:
a fourth holding chamber located in the substrate, the fourth holding chamber having a space usable to accommodate a second liquid; and
an another flow path connecting the fourth holding chamber and the reaction chamber to each other, the another flow path being usable to transfer the second liquid;
wherein:
the first holding chamber has an outermost side surface located farthest from the rotation shaft, an adjacent side surface adjacent to the outermost side surface, and a recessed portion defined by the outermost side surface and the adjacent side surface;
the fourth holding chamber has an outermost side surface located farthest from the rotation shaft, an adjacent side surface adjacent to the outermost side surface, and a recessed portion defined by the outermost side surface and the adjacent side surface; and
the adjacent side surface of the first holding chamber and the adjacent side surface of the fourth holding chamber are unparallel to each other as seen in a direction parallel to the rotation shaft.

15. A sample analysis system, comprising:
the sample analysis substrate of claim 1; and
a sample analysis device including:
a motor rotating the sample analysis substrate about the rotation shaft;
a rotation angle detection circuit detecting a rotation angle of a rotation shaft of the motor;
a driving circuit controlling the rotation of the motor and the rotation angle at which the motor stops, based on a result of the detection of the rotation angle detection circuit; and
a control circuit including an operator, a memory and a program stored on the memory so as to be executable by the operator, the control circuit controlling an operation of the motor, the rotation angle detection circuit and the driving circuit based on the program;
wherein in the case where the sample analysis substrate in which the first holding chamber and the reaction chamber have the first liquid and the liquid sample introduced thereto is mounted on the sample analysis device, the program:
(a) rotates the sample analysis substrate to transfer the liquid sample in the reaction chamber to the main chamber;
(b) rotates the sample analysis substrate to, after step (a), transfer the first liquid in the first holding chamber to the reaction chamber; and
(c) rotates the sample analysis substrate to transfer the first liquid in the reaction chamber to the main chamber.

16. A sample analysis device, comprising:
a motor rotating the sample analysis substrate of claim 1 about the rotation shaft;
a rotation angle detection circuit detecting a rotation angle of a rotation shaft of the motor;
a driving circuit controlling the rotation of the motor and the rotation angle at which the motor stops, based on a result of the detection of the rotation angle detection circuit; and
a control circuit including an operator, a memory and a program stored on the memory so as to be executable by the operator, the control circuit controlling an operation of the motor, the rotation angle detection circuit and the driving circuit based on the program;
wherein in the case where the sample analysis substrate in which the first holding chamber and the reaction chamber have the first liquid and the liquid sample introduced thereto is mounted on the sample analysis device, the program:

(a) rotates the sample analysis substrate to transfer the liquid sample in the reaction chamber to the main chamber;

(b) rotates the sample analysis substrate to, after step (a), transfer the first liquid in the first holding chamber to the reaction chamber; and (c) rotates the sample analysis substrate to transfer the first liquid in the reaction chamber to the main chamber.

17. A non-transitory computer-readable storage medium storing a program for a sample analysis system, the sample analysis system including:

the sample analysis substrate of claim 1; and a sample analysis device including:

a motor rotating the sample analysis substrate about the rotation shaft;

a rotation angle detection circuit detecting a rotation angle of a rotation shaft of the motor;

a driving circuit controlling the rotation of the motor and the rotation angle at which the motor stops, based on a result of the detection of the rotation angle detection circuit; and a control circuit including an operator, a memory and a program stored on the memory so as to be executable by the operator, the control circuit controlling an operation of the motor, the rotation angle detection circuit and the driving circuit based on the program;

wherein in the case where the sample analysis substrate in which the first holding chamber and the reaction chamber have the first liquid and the liquid sample introduced thereto is mounted on the sample analysis device, the program:

(a) rotates the sample analysis substrate to transfer the liquid sample in the reaction chamber to the main chamber;

(b) rotates the sample analysis substrate to, after step (a), transfer the first liquid in the first holding chamber to the reaction chamber; and (c) rotates the sample analysis substrate to transfer the first liquid in the reaction chamber to the main chamber.

* * * * *